(12) United States Patent
de Vetten et al.

(10) Patent No.: US 9,856,494 B2
(45) Date of Patent: Jan. 2, 2018

(54) CLONING AND EXPLOITATION OF A FUNCTIONAL R-GENE FROM SOLANUM X EDINENSE

(75) Inventors: Nicolaas Clemens Maria Henricus de Vetten, Groningen (NL); Estelle Celine Verzaux, Wageningen (NL); Jacobus Hubertus Vossen, Wageningen (NL); Hendrik Rietman, Wageningen (NL); Vivianne Gertruda Antonia Anna Vleeshouwers, Wageningen (NL); Evert Jacobsen, Wageningen (NL); Richard Gerardus Franciscus Visser, Bennekom (NL)

(73) Assignee: COOPERATIE AVEBE U.A., Veendam (NL)

( * ) Notice: Subject to any disclaimer, the term of this patent is extended or adjusted under 35 U.S.C. 154(b) by 653 days.

(21) Appl. No.: 13/699,334

(22) PCT Filed: May 31, 2011

(86) PCT No.: PCT/NL2011/050386
§ 371 (c)(1),
(2), (4) Date: Jan. 28, 2013

(87) PCT Pub. No.: WO2011/152722
PCT Pub. Date: Dec. 8, 2011

(65) Prior Publication Data
US 2014/0041072 A1    Feb. 6, 2014

(30) Foreign Application Priority Data
May 31, 2010   (EP) ..................... 10164531

(51) Int. Cl.
*A01H 1/04*    (2006.01)
*C12N 15/82*   (2006.01)
*C07K 14/415*  (2006.01)
*C12Q 1/68*    (2006.01)

(52) U.S. Cl.
CPC ........... *C12N 15/8286* (2013.01); *A01H 1/04* (2013.01); *C07K 14/415* (2013.01); *C12N 15/8279* (2013.01); *C12N 15/8282* (2013.01); *C12Q 1/6895* (2013.01); *C12Q 2600/13* (2013.01)

(58) Field of Classification Search
CPC .................................................. C12N 15/82
See application file for complete search history.

(56) References Cited

FOREIGN PATENT DOCUMENTS

| WO | WO/2009/013468 | * | 1/2009 | ............. C12N 15/82 |
| WO | WO 2009/013468 A2 | | 1/2009 | |
| WO | WO 2009/103960 A2 | | 8/2009 | |

OTHER PUBLICATIONS

ADB85624.1 _rpi-vnt1-like protein, partial [Solanum okadae]—Protein—NCBI, GenBank, Jan. 1, 2010.*
Reverberi, Roberto, and Lorenzo Reverberi. "Factors affecting the antigen-antibody reaction." Blood Transfusion 5.4 (2007): 227.*
Foster, Simon J., et al. "Rpi-vnt1. 1, a Tm-22 homolog from Solanum venturii, confers resistance to potato late blight." Molecular Plant-Microbe Interactions 22.5 (2009): 589-600.*
Ugent, Donald. "Morphological variation in Solanum x edinense, a hybrid of the common potato." Evolution (1967): 696-712.*
Fry, William E. and Niklaus J. Grünwald. 2010. Introduction to Oomycetes. The Plant Health Instructor. DOI:10.1094/PHI-I-2010-1207-01.*
Kamoun, Sophien. "Molecular genetics of pathogenic oomycetes." Eukaryotic cell 2.2 (2003): 191-199.*
van der Lee, Theo, et al. "Chromosomal deletion in isolates of Phytophthora infestans correlates with virulence on R3, R10, and R11 potato lines." Molecular plant-microbe interactions 14.12 (2001): 1444-1452.*
Ellis, Jeff, Peter Dodds, and Tony Pryor. "Structure, function and evolution of plant disease resistance genes." Current opinion in plant biology 3.4 (2000): 278-284.*
Database EMBL., "Solanum okadae isolate oka970-3 rip-vnt1-like protein gene, partial cds.", Jan. 28, 2010, XP002604522.
Collins, A, Et al., "QTL for field resistance to late blight in potato are strongly correlated with maturity and vigour", Molecular Breeding, vol. 5, No. 5, 1999, pp. 387-398, XP002604523.
Van Der Linden C Gerard, et al., "Efficient targeting of plant disease resistance loci using NBS profiling", Theoretical and Applied Genetics, vol. 109, No. 2, Jul. 2004, pp. 384-393.

* cited by examiner

*Primary Examiner* — Lee A Visone
*Assistant Examiner* — Weihua Fan
(74) *Attorney, Agent, or Firm* — Hoffman & Baron, LLP

(57) ABSTRACT

The invention relates to a new resistance gene, Rpi-edn2 and functional homologues or functional fragments thereof isolated from S. x edinense. Moreover, the invention relates to the use of said resistance gene, for example the use of said resistance gene in a method to increase or confer at least partial resistance in a plant to an oomycete infection. The invention provides an isolated or recombinant nucleic acid sequence comprising a nucleic acid sequence encoding one of the amino acid sequences of FIG. 4 or a functional fragment or a functional homologue thereof.

29 Claims, 16 Drawing Sheets

Fig. 2

Figure 3:
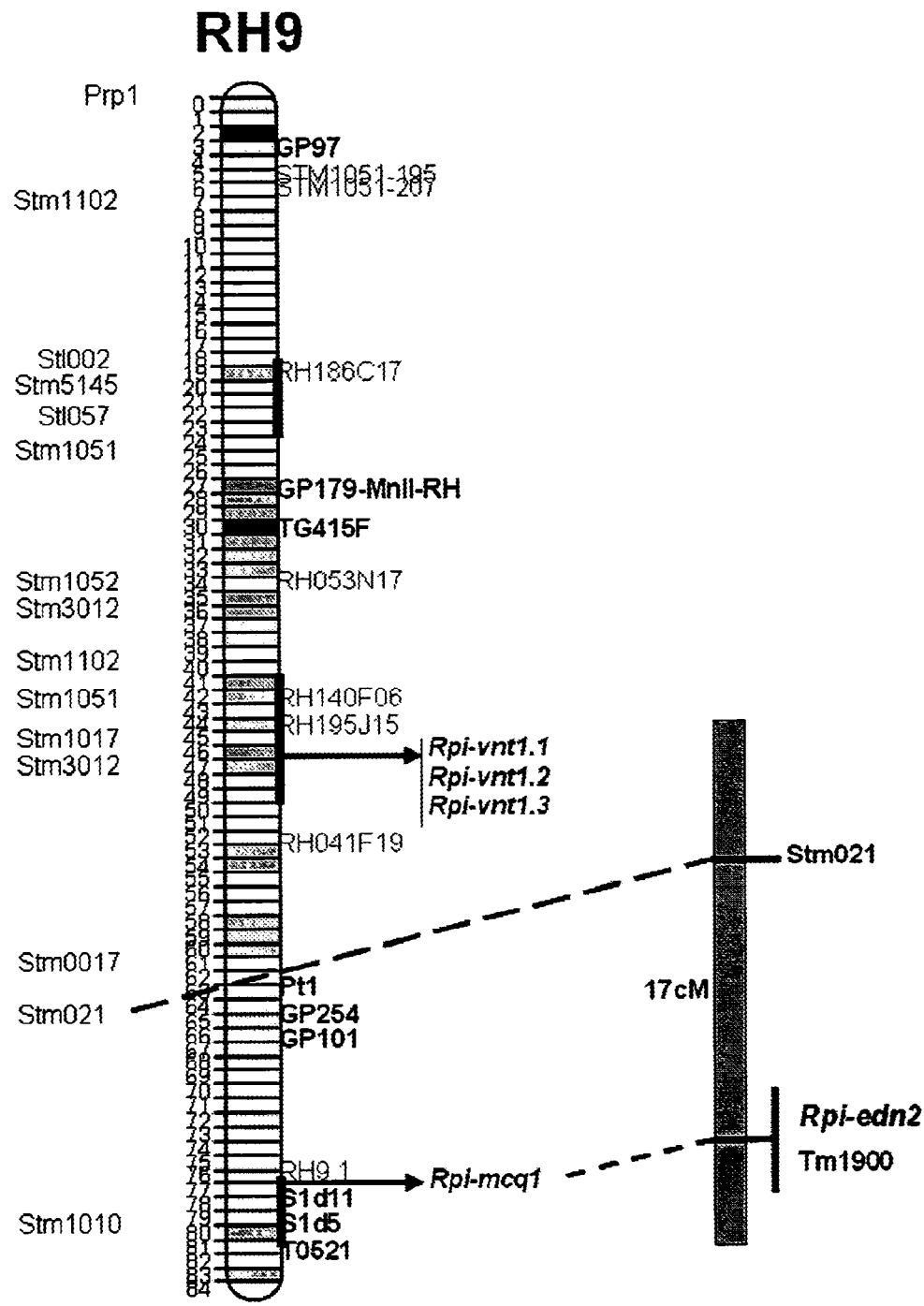

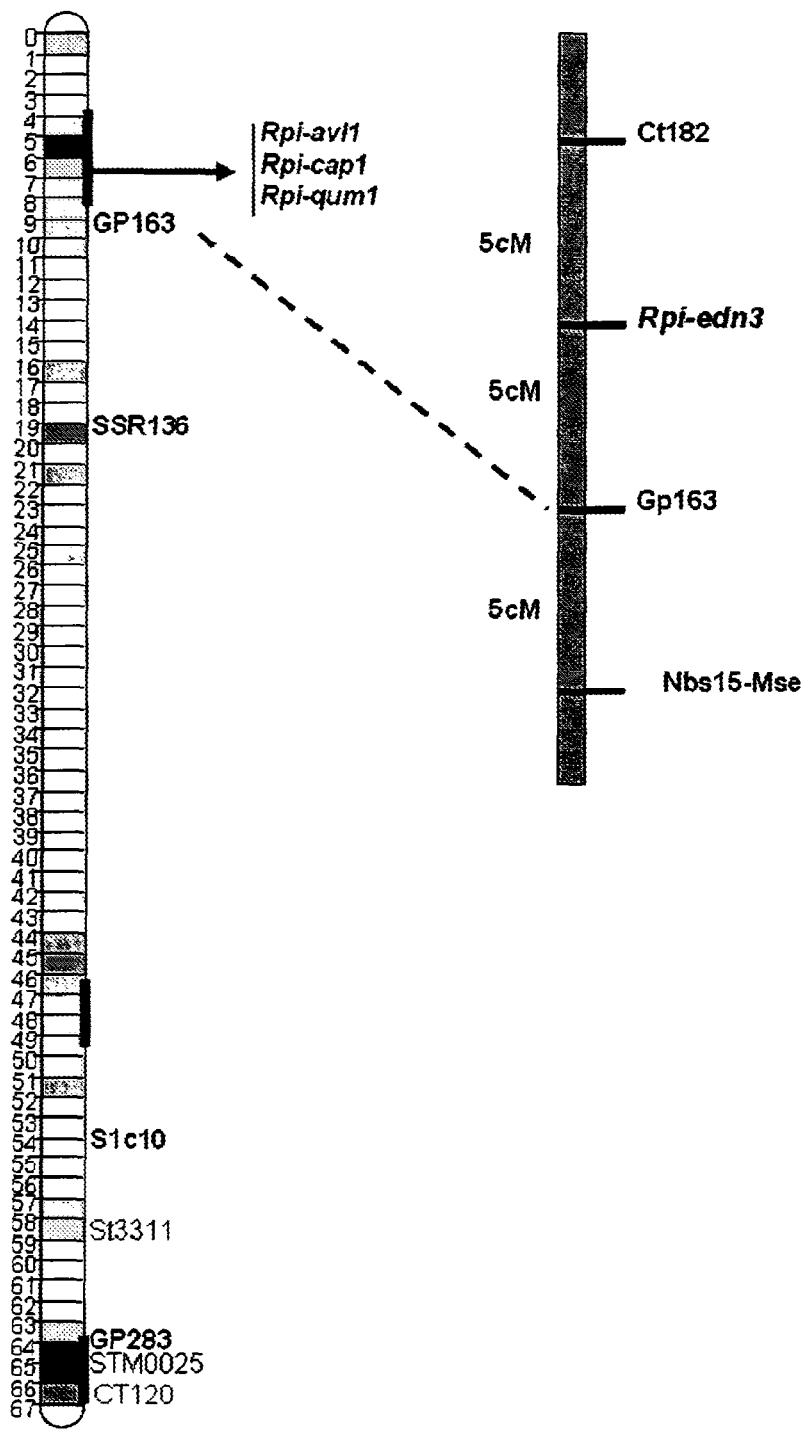
Fig. 3, cont'd

Fig. 4

NUCLEIC ACID SEQUENCE OF Rpi-edn2

```
   1 atggctgaaa ttcttcttac agcagtcatc aataaatctg tagaaatagc tgcaaatgta
  61 ctctttcaac aagggagccg cttgaatttt ttgaaagagg acatcgattg gctccagaga
 121 gtactgagac acattcgatc atatgtagac gatgcaaagg ccaaggaagt tggaggcgat
 181 tcaagggtca aaaacttatt aaaagatatt caagaattgg caggtgatgt ggaggatctc
 241 ttagatgagt ttcttccaaa aatccaacaa tccagtaagt tcaaaggcgc aatttgttgc
 301 cttaagacgg tttctttttgc cgatgagttt gctgtggaga ttgagaagat aagaagaagg
 361 gttgctgaca ttgatagttt aaggacaact ttcaacatca cagatacaag taacaacaat
 421 aatgattgca ttccaatgga acagagaaga aaattccttc atgctgatga acagaggtc
 481 atcggtttgg atgatgactt caacaagctc caagacaaat tgcttgttca agatttgtgt
 541 aatggagttg tttcaatagt tggcatgcct ggtctaggaa aaacaactct tgccaagaaa
 601 ctttataggc atgtccgtca tcaatttgag tgttctgcac tggtctacgt ttcacaacag
 661 ccaagagcag gagaaatctt acttgacata gccaagcaag ttggactgac ggacgaggga
 721 aggaagaac acttggagga caatctaaga tcacttttgg aaacaaaaag gtatgttatt
 781 ctcttagatg acatttggga tactaaaatc tgggatgctc tgaaccgtgt ccttcgtcct
 841 gaatgtgatt caaaaattgg cagtaggata attatcactt ctcgatatca tcatgtaggc
 901 agatacatag gagaggattt ctcgctccac gagttgcaac ccttagattc agagaaaagt
 961 tttgaactct ttaccaagaa aatctttatt tttgataata ataataattg ggctaatgct
1021 tcacctgtct tggtagatat tggtaaaagt atagttcgga gatgtggagg tattccatta
1081 gccattgtgg tgacggcagg catgttaagg gcaagagaaa gaacggaaca tgcatggaat
1141 agagtgcttg agcgtatagg tcataatatt caggatggat gtgctaaggc attggctctg
1201 agttacaatg atttgcccat tgcattaagg ccatgttttct tgtactttgg tctttacccc
1261 gaggaccatg aaattcgtgc ttttgatttg acaaatatgt ggattgctga gaagctgata
1321 gttgtaaata gtggcaatag gcgagaggct gaaagtttgg cggatgatgt cctaaatgat
1381 ttggtttcaa gaaacttgat tcaagttgcc aagaggacat atgatggagg aatttcaagt
1441 tgtcgcatac atgacttgtt acatagtttg tgtgttgact tggctaagga aagcaacttc
1501 tttcacaccg agcacaatgc atttggtgat cccggcaatg tttctaggct gcgaaggatt
1561 acattctact ctgataataa tgccatgaat gagttcttcc gttcaaatcc taagcttgag
1621 aagcttcgtg cacttttctg tttcacaaaa ggagactctt gcatatttc tcatttggct
1681 catcatgact tcaaattatt acaagtgttg gttgtagtcc agcctcgaaa aaattatgat
1741 ttcagcatta gccaaatcaa aattgggaac atgagttgct tacgctatct gcgattcgag
1801 ggggatattt atgggggaact gccaaattgt atggtgaagc tcaaacactt agagcccta
1861 gatattagta aaagcttcat tattaaactt cctactggtg tttggaagac tacacaattg
1921 agacatcttc gttctaatgg ttataatcta gcaccttaca gttactttg tataagccca
1981 tttttccaa acgtgcctcc taatatgta caaactttga tgtggatgga tggtgaattt
2041 tttgaaccga gatggttgca ccgatttatc aatttaagaa aactgggttt acaggaagta
2101 tccgattcta ccattaagaa attatcaaca ttgagccctg tgccaacgac actggaggtt
2161 ctaaagctca gctcattttt cagtgaattg agagagcaaa taaacttgtc gtcgtatcca
2221 aatattgtta agttgcattt gaacggaaga attcccttga acgtctctga atcattccct
2281 ccaaatcttg tcaagcttac tcttttgcaac ttgatggtag acggtcatgt agtggcagtg
2341 cttaagaaat tacccaaatt aaagatactt acattgcata ggtgcagaca tgatgcagaa
2401 aaaatggatc tctctggtga tggtgatagc tttccgcaac ttgaagtttt gcatattaaa
2461 gatccagtct gcttgtctga agtaacgtgc acggatgatg tcggtatgcc taaattgaaa
2521 aagttattac ttatagaaag aactgattcc aacgttaggc tctcggaaag acttgcaaaa
2581 ctgagagtat ga                                (SEQ ID NO 40)
```

AMINO ACID SEQUENCE OF Rpi-edn2

```
  1 maeilltavi nksveiaanv lfqqgsrlnf lkedidwlqr vlrhirsyvd dakakevggd
 61 srvknllkdi qelagdvedl ldeflpkiqq sskfkgaicc lktvsfadef aveiekirrr
121 vadidslrtt fnitdtsnnn ndcipmeqrr kflhadetev iglddfnkl qdkllvqdlc
181 ngvvsivgmp glgkttlakk lyrhvrhqfe csalvyvsqq prageilldi akqvgltdeg
241 rkehlednlr slletkryvi llddiwdtki wdalnrvlrp ecdskigsri iitsryhhvg
301 ryigedfslh elqpldseks felftkkifi fdnnnnwana spvlvdigks ivrrcggipl
361 aivvtagmlr arertehawn rvlerighni qdgcakalal syndlpialr pcflyfglyp
421 edheirafdl tnmwiaekli vvnsgnrrea esladdvlnd lvsrnliqva krtydggiss
481 crihdllhsl cvdlakesnf fhtehnafgd pgnvsrlrri tfysdnnamn effrsnpkle
541 klralfcftk gdscifshla hhdfkllqvl vvvqprknyd fsisqikign msclrylrfe
601 gdiygelpnc mvklkhletl disksfiikl ptgvwkttql rhlrsngynl apysyfcisp
661 ffpnvppnnv qtlmwmdgef feprwlhrfi nlrklglqev sdstikklst lspvpttlev
721 lkissffsel reqinlssyp nivklhlngr iplnvsesfp pnlvkitlcn lmvdghvvav
781 lkklpklkil tlhrcrhdae kmdlsgdgds fpqlevlhik dpvclsevtc tddvgmpklk
841 klllier tds nvrlserlak lrv
                                              (SEQ ID NO 41)
```

Fig. 5

```
Rpi-edn2    ---------------------------------MAEILLTAVINKSVEIAANVLFQQGSR
Rpi-vnt1    MNYCVYKTWAVDSYFPFLILTFRKKKFNEKLKEMAEILLTAVINKSIEIAGNVLFQEGTR
Rpi-mcq1    ---------------------------------MAEILLTAVINKSVEIAGNVLFQEGTR
Rpi-mcq2    ---------------------------------MAEILLTTVINKSVGIAANVLFQEGTR
Tm2-2       ---------------------------------MAEILLTSVINKSVEIAGNLLIQEGKR
                                             ******* ***** ** * * * * *

Rpi-edn2    LNFLKEDIDWLQRVLRHIRSYVDDAKAKEVGGDSRVKNLLKDIQELAGDVEDLLDEFLPK
Rpi-vnt1    LYWLKEDIDWLQREMRHIRSYVDNAKAKEVGGDSRVKNLLKDIQQLAGDVEDLLDEFLPK
Rpi-mcq1    LYWLKEDIDWLQREMRHIRSYVDNAKAKEVGGDSRVKNLLKDIQQLAGDVEDLLDEFLPK
Rpi-mcq2    LYWLKEDIDWLHREMRHIRSYVDDAKAKEVGGDSRVRNLLKDIQQLAGDVEDLLDEFLPK
Tm2-2       LYWLKEDIDWLQREMRHIRSYVDNAKAKEAGGDSRVKNLLKDIQELAGDVEDLLDDFLPK
            * ******** * ******* ***** ****** ********** **** **** ****

Rpi-edn2    IQQSSKFKGAICCLKTVSFADEFAVEIEKIRRRVADIDSLRTTFNITDTSNNNNDCIPME
Rpi-vnt1    IQQSNKF---ICCLKTVSFADEFAMEIEKIKRRVADIDRVRTTYSITDTSNNNDDCIPLD
Rpi-mcq1    IQQSSKFKGAICCLKTVSFADEFAMEIEKIKRRVVDIDRVRTTYNIMDT-NNNNDCIPLD
Rpi-mcq2    IQQSNKF---ICCLKTVSFADEFAMEIEKIKRRVADITRVRTTYNITDTSNNNDDCIPLD
Tm2-2       IQQSNKFN---YCLKRSSFADEFAMEIEKIKRRVVDIDRIRKTYNIIDTDNNNDDCVLLD
            **** **    *** ******* ***** *** **  *  *  ** *** ** **

Rpi-edn2    QRRKFLHADETEVIGLDDDFNKLQDKLLVQDLCNGVVSIVGMPGLGKTTLAKKLYRHVRH
Rpi-vnt1    RRRLFLHADETEVIGLEDDFNTLQAKLLDHDLPYGVVSIVGMPGLGKTTLAKKLYRHVCH
Rpi-mcq1    QRRLFLHVDETEVIGLDDDFNTLQAKLLDQDLPYGVVSIVGMPGLGKTTLAKKLYRHVRH
Rpi-mcq2    RRRLFLHADETEVIGLEDDFNTLKAKLLDQDLPYGVVSIVGMPGLGKTTLAKKLYRHVRD
Tm2-2       RRRLFLHADETEIIGLDDDFNMLQAKLLNQDLHYGVVSIVGMPGLGKTTLAKKLYRLIRD
             ** *** **** *** *** * *** *** ***  **********************

Rpi-edn2    QFECSALVYVSQQPRAGEILLDIAKQVGLTDEGRKEHLEDNLRSLLETKRYVILLDDIWD
Rpi-vnt1    QFECSGLVYVSQQPRAGEILHDIAKQVGLTEEERKENLENNLRSLLKIKRYVILLDDIWD
Rpi-mcq1    KFECSVLVYVSQQPRAGEILIDIAKQVGLTEDERKENLENNLRSLLKRKRYVILLDDIWD
Rpi-mcq2    QFESSGLVYVSQQPRAGEILRDIAKQVGLPKEERKENLEGNLRSLLKTKRYVILLDDIWD
Tm2-2       QFECSGLVYVSQQPRASEILLDIAKQIGLTEQKMKENLEDNLRSLLKIKRYVILLDDIWD
            ** * ********** *** *****  **    ** **  ***** *  **********

Rpi-edn2    TKIWDALNRVLRPECDSKIGSRIIITSRYHHVGRYIGEDFSLHELQPLDSEKSFELFTKK
Rpi-vnt1    VEIWDDLKLVL-PECDSKIGSRIIITSRNSNVGRYIGGDFSIHVLQPLDSEKSFELFTKK
Rpi-mcq1    VEIWDDLKLVL-PECDSKIGSRIIITSRNSNVGRYIGGDFSIHVLQPLNSENSFELFTKK
Rpi-mcq2    VEIWDDLKLVL-PECDSEIGSRIIITSRNSNVGRYIGGDFSIHMLQPLDSENSFELFTKK
Tm2-2       VEIWDDLKLVL-PECDSKVGSRMIITSRNSNVGRYIGGESSLHALQPLESEKSFELFTKK
             *** *  **  ***** **** ***** * ****** *   *  *** ** *******

Rpi-edn2    IFIFDNNNNWANASPVLVDIGKSIVRRCGGIPLAIVVTAGMLRARERTEHAWNRVLERIG
Rpi-vnt1    IFNF-VNDNWANASPDLVNIGRCIVERCGGIPLAIVVTAGMLRARGRTEHAWNRVLESMA
Rpi-mcq1    IFIFDNNNNWTNASPNLVDIGRSIVGRCGGIPLAIVVTAGMLRARERTERAWNRLLESMS
Rpi-mcq2    IFTFDNNNNWANASPDLVDIGRSIVGRCGGIPLAIVVTAGMLRARERTEHAWNRVLESMG
Tm2-2       IFNFDDNNSWANASPDLVNIGRNIVGRCGGIPLAIVVTAGMLRARERTEHAWNRVLESMG
            ** *  *  * **** ** **  ** ******************* *** **** **

Rpi-edn2    HNIQDGCAKALALSYNDLPIALRPCFLYFGLYPEDHEIRAFDLTNMWIAEKLIVVNSGNR
Rpi-vnt1    HKIQDGCGKVLALSYNDLPIALRPCFLYFGLYPEDHEIRAFDLTNMWIAEKLIVVNTGNG
Rpi-mcq1    HKVQDGCAKVLALSYNDLPIALRPCFLYFGLYPEDHEIRAFDLTNMWIAEKLIVVNSGNG
Rpi-mcq2    HKVQDGCAKVLALSYNDLPIALRPCFLYLGLFPEDHEIRAFDLTNMWIAEKLIVVNSGNG
Tm2-2       HKVQDGCAKVLALSYNDLPIASRPCFLYFGLYPEDHEIRAFDLINMWIAEKFIVVNSGNR
            * **** * * ********** ****** ** ********** ****** **** **
```

Fig. 5, cont'd

```
Rpi-edn2    REAESLADDVLNDLVSRNLIQVAKRTYDGGISSCRIHDLLHSLCVDLAKESNFFHTEHNA
Rpi-vnt1    REAESLADDVLNDLVSRNLIQVAKRTYDGRISSCRIHDLLHSLCVDLAKESNFFHTEHNA
Rpi-mcq1    REAESLADDVLNDLVSRNMIQVAKRTYDGRISSCRIHDLLHSLCVDLAKESNFFHTEHNA
Rpi-mcq2    REAESLAEDVLNDFVSRNLIQVSQRKCNGRISSYRIHDLLHSLCVELGKESNFFHTEHNA
Tm2-2       REAEDLAEDVLNDLVSRNLIQLAKRTYNGRISSCRIHDLLHSLCVDLAKESNFFHTAHDA
            ****  **  ***** ****  **     *   *** ************ ******** * *

Rpi-edn2    FGDPGNVSRLRRITFYSDNNAMNEFFRSNPKLEKLRALFCFTKGDSCIFSHLAHHDFKLL
Rpi-vnt1    FGDPSNVARVRRITFYSDDNAMNEFFHLNPKPMKLRSLFCFTK-DRCIFSQMAHLNFKLL
Rpi-mcq1    LGDPGNVARLRRITFYSDNNAMNEFFRSNPKLEKLRALFCFTE-DPCIFSQLAHLDFKLL
Rpi-mcq2    FGDPDNVARVRRITFYSDNNAMSKFFRSNPKKLRALFCFTNLDSCIFSHLAHHDFKLL
Tm2-2       FGDPGNVARLRRITFYSD-NVMIEFFRSNPKLEKLRVLFCFAK-DPSIFSHMAYFDFKLL
            ***  **  *  ******** *  **  ***  *** *** ****    *  *** *  *   ****

Rpi-edn2    QVLVVVQPRKNYDFSISQIKI----GNMSCLRYLRFEGDIYGELPNCMVKLKHLETLDIS
Rpi-vnt1    QVLVVVMSQKGYQHVTFPKKI----GNMSCLRYVRLEGAIRVKLPNSIVKLKCLETLDIF
Rpi-mcq1    QVLVVV----IFVDDICGVSIPNTFGNMRCLRYLRFQGHFYGKLPNCMVKLKRLETLDIG
Rpi-mcq2    QVLVVVISYNWLSVSISN-KF----GKMSCLRYLRLEGPIVGELSNSIVKLKRVETIDIA
Tm2-2       HTLVVVMSQSFQAYVTIPSKF----GNMTCLRYLRLEGNICGKLPNSIVKLTRLETIDID
            ****                      *  * ****  *  *        *  *  ***   ** **

Rpi-edn2    KSFIIKLPTGVWKTTQLRHLRSNGYNLAPYSYFCISPFFPNV---PPNNVQTLMWMDGEF
Rpi-vnt1    HS-SSKLPFGVWESKILRHLC---YTEECYCVSFASPPFCRIM---PPNNLQTLMWVDDKF
Rpi-mcq1    YS-LIKFPTGVWKSTQLKHLRYGGFNQASNSCFSISPFFPNLYSLPHNNVQTLMWLDDKF
Rpi-mcq2    GD-NIKIPCGVWESKQLRHLRNREER---RYFFSVSPFCLNMYPLPPNNLQTLVWMDDKF
Tm2-2       RRSLIQPPSGVWESKHLRHLCYRDYGQACNSCFSISSFYPNIYSLHPNNLQTLMWIPDKF
               *  ***    *  **          * *            ** ***  *        *

Rpi-edn2    FEPRWLHRFINLRKLGLQEVSDSTIKKLSTLSPVPTTLEVLKLSSFFSELREQINLSSYP
Rpi-vnt1    CEPRLLHRLINLRTLCIMDVSGSTIKILSALSPVPRALEVLKL-RFFKNTSEQINLSSHP
Rpi-mcq1    FEAGLLHRLINLRKLGIAGVSDSTVKILSALSPVPTALEVLKL-KIYRDMSEQINLSSYP
Rpi-mcq2    FEPRLLHRLINLRKLGIWGTSDSTIKILSALSPVPTALEVLKL-YFLRDLSEQINLSTYP
Tm2-2       FEPRLLHRLINLRKLGILGVSNSTVKMLSIFSPVLKALEVLKL-SFSSDPSEQIKLSSYP
            *   *** **** *    * **  *  **   ***  ******    *** ** *

Rpi-edn2    NIVKLHLN--G--RIPLNVSESFPPNLVKLTLCNLMVDGHVVAVLKKLPKLKILTLHRCR
Rpi-vnt1    NIVELGLV--GFSAMLLNI-EAFPPNLVKLNLVGLMVDGHLLAVLKKLPKLRILILLWCR
Rpi-mcq1    NIVKLRLNVCG--RMRLN-CEAFPPNLVKLTLVGDEVDGHVVAELKKLPKLRILKMFGCS
Rpi-mcq2    NIVKLNLQ--GFVRVRLN-SEAFPPNLVKLILDKIEVEGHVVAVLKKLPTLRILKMYGCK
Tm2-2       HIAKLHLNV-N--RTMALNSQSFPPNLIKLTLAYFSVDRYILAVLKTFPKLRKLKMFICK
             *  *              *****  **  *       *  **   * ** * * *    *

Rpi-edn2    HDAEKMDLSGD--GD--SFPQLEVLHIKDPVCLSEVTCTDDVGMPKLKKLLLIERTDSN-
Rpi-vnt1    HDAEKMDLS----GD--SFPQLEVLYIEDAQGLSEVTCMDDMSMPKLKKLFLVQGPNISP
Rpi-mcq1    HNEEKMDLSGD--GD--SFPQLEVLHIDEPDGLSEVTCRDDVSMPKLKKLLLVQRRPSP-
Rpi-mcq2    HNEEKMDLSGD--GDGDSFPQLEVLHIERPFFLFEITCTDDDSMPKLKKLLL---TTSN-
Tm2-2       YNEEKMDLSGEANGY--SFPQLEVLHIHSPNGLSEVTCTDDVSMPKLKKLLL-TGFHCR-
             *****   *        ********  *       * **  **  ********  *

Rpi-edn2    --VRLSERLAKLRV----  (SEQ ID NO 41)
Rpi-vnt1    ISLRVSERLAKLRISQVL  (SEQ ID NO 42)
Rpi-mcq1    --ISLSERLAKLRI----  (SEQ ID NO 43)
Rpi-mcq2    --VRLSERLAKLRV----  (SEQ ID NO 44)
Tm2-2       --ISLSERLKKLSK----  (SEQ ID NO 45)
               **** **
```

Fig. 8A

```
AAGGGGTTCGCGTTGGCCGATTCATTAATGCAGCTGGCACGACAGGTTTCCCGACTGGAAAGCGGGCAGTGAGCGCAACG
CAATTAATGTGAGTTAGCTCACTCATTAGGCACCCCAGGCTTTACACTTTATGCTTCCGGCTCGTATGTTGTGTGGAATT
GTGAGCGGATAACAATTTCACACAGGAAACAGCTATGACCATGATTACGCCAAGCTATTTAGGTGAGACTATAGAATACT
CAAGCTTGCATGCCTGCAGGTCGACTCTAGAGGATCTTAAAGAAGCTAAAAGAATTGTGAGTTTTTACTCTATTGTTAGA
AAGGTTGCACTTAAAGTTGAAAAAAGTGACTCTACAAGATTGAGATACTTGTGTGATATTGGTTGTCCATTTGAGTGTTT
GATATCTGAAGATAGGAAAAATCAGGGATTCAAAATTAAAACCTTGAACACCAAACACTCATGTGGTGAAAATGCTTTTA
AGAATAGAAGAGCCACTCAAGAAGCTTTAGCATACTACTTCAAGAAAAAaCTTCAGAATAATCCAAAGTACAGTGTAAAT
GATATGAGACAAGATTTGGATGATAATTTTAATTTGAACGTTAGTTATTCAAGATGAAGAGGGTTAAAAGGCTTGTGTT
AGAGAAATTGGAGGGTAGCTACATTGATGAATTCAATAAGTTGGAGGGCTATGCTCAAGAATTGAGGGACAGCAACCCTG
GTACTGATGTTATCATAAATATATCTAGAGATGCTTTGGAACAAGGTAAAaGAAAATTCTTAAGAATGTATGTGTGCATT
CAAGCTTTAAAAAATGGCTGGAAAGGAGGTTTGAGGCCTTTTATAGGGCTAGATGGGACTTTTTTAAAAGGAAAATGCAA
GGGAATCTTGTTGGTTGCAATGGGACAAGATTCAGTGAAACACTTCTATCCACTTGCTTGGGCAGTGGTGGACAGAGAGA
CATCTAGAACATGGAAATGGTTTATTGAGTTGCTGAGAAATTCTCTAGACCTGGCAAATGGTGAAGGAGTAACATTCATG
TCTGATATGCATAAGGTAGTTGTTTCTGATTTTAATAAGTTTCTGATTTTCAGTTAAATTCTTATACAAATAATACTTTA
ACTTGTTATGATTTTTATTGTTACAGGGGCTACTGGATGCTGTTAGTCAGGTGTTTCCTAAAGCACATCATAGATGGTGT
GCAAGGCACATAGAAGCTAATTGGAGCAAGGCTTGGAAAGGTGTACAGATGAGAAAGTTACTGTGGTGGTCTGCCTGGAG
CACCTATGAAGAAGAATTTCATGATCAATTGAAAGTCATGGGTGCTGTGTCTAAACAAGCTGCAAAGGATTTGGTATGGT
ACCCTGCACAAAACTGGTGCAGGGCTTATTTTGACACAGTCTGCAAAAATCACTCATGTGAGAATAATTTTACCGAGTCA
TTCAACAAATGGATTCTAGAAGCAAGGGCAAAACCTATAATCAAGATGTTAGAAATATTAGAATCAAGGTGAGTTGTTA
CTGTTTATATTATCATCTTTTATATTATCTTAATCTAACTATTAGGTTCTATGTAGGTTAGATTAATGTGGGATAATACT
GAAAATTAGAGTTTGGGTTGTTTACAGTTTGGTGATTTTGAGTTTTCGGCTCACAAAGTTGTAATTTTTCTTATTCTTTT
CAAATTCTGCTGCTTTTGTTGTGAACTATGGCCTTGTTTTTCTTTATTTGAATCTCTTGGGTATTTACAAAACGAATTTA
TCAGGAACTGAATTTTACATTTGAGATTAAGGCCTTAAAGAGCAGTGCTCAATTCTCTGTAAATTTATTTTCATTGATAG
ATATAGTGTTTTAATAGAAATAGCAGAATATAGTTTGATGTGACTGTTATATTGATAGGATATGTTGATCTTACTGTTGT
ATTGTTATATAGATTATGAATAGGTTGCAAAAACTTGAAGAAGAAGGTAAAAATTGGAAAGGAGATTTTAGTCCATATGC
CATGGAGTTGTATAATGATTTCAATATCATTGCAACATGTTGTCAAGTTCAATCTAATGGAGACCAAGGATATGAGGTAG
TTGAGGGTGAAGATAGGCATGTGGTGAATCTTAATAGGAAGAAGTGTACATGTAGGACATGGGACTTGACTGGTATACCA
TGTCCTCATGCCATTAAAGCATATCTTCATGACAAACAAGAACCACTGGATCAGTTGAGTTGGTGGTATTCCAGAGAAGC
TTACATGTTGGTATACATGCATAAAATACAACCTGTTAGAGGTGAGAAGTTCTGGAAAGTTGATCCTTCTCATGCTATGG
AGCCACCAGAAATACATAAATTGGTAGGCAGGCCAAAACTTAAGAGAAAGAGAGAAAAGGATGAGGCAAGGAAAAGGGAA
GGGGTGTGGTTAGCTTCAAGAAAAGGACTAAAAATGACATGTGGACATTGTAGTGCAACAGGTCACAACCAAAGAAGATG
TCCTATGGTATGTAATTTTCTTTACTTGGTCAATATTTACACTAGTTAATTCAACATCTAACTAATTTTGTCATTTTTAT
AGCTTCAAAGATCAAAACAACCAACCCAAGATGTGCCAATGTCAGCACCCCAAGCCAGTCAAGAAGAATCTGATATTGTC
TTCATGCCTACTCCTGGCTTTATTGCTTCTTCAAGTCAACAGAGTATCCAACCTGCTGGTCCTTCAAATTCAAAGAAAAT
TGAAAAGAAACCTACTGGACCTTCAAAGTCAAAGAGAAAAATAGTTGCTGATGAATCTGAGGATGAGCAACATGTTGCAC
CTTCAAGTGCAGTTGCTGATGAGGATAGAGGTGAGCATGAAAGTGAAGACGAGCAGACAATTCTAAGGCCGAAGGCAATT
TCTGAAGCTAGGACTAGGCTTCAAGCTAAAAAGATACAGATTCGACCAACTGGTACCAGGAGGATTGGCTTCAAAGGAGA
TGACAATGGTGTGAGCATTCCAACTAATCTGCCATACTCACCAAGAAAATTGGCATGGAAAGGAAAAGAAACTATGACTT
CAAATCAGTTGACAGCTGAAAAGGAGATCAGAATTGGCAATTTGAAGGCAAAGAAAGGAAAAAAATCTACGACTTCAGAT
CAGTTGACTGTTGAAAAGGAGAAAAAAATTGGCAAATTGAAGGCAAAAGGGGTGGGAAGAAGTAGTTGCATTATGAAGT
TGGTTTTTtGTTTTCCGGTGTTATGTAATGGCATGATGAAACTTAATATTTTGACTTTTTTGATATTACTCTGTCTTGAA
CAAGTGTCTGTAAGTTTTTGTGGGTTCAAAATATATGACAATGCCATTACTACTTATCTATGTAGTTGTTATTTTTtGTT
TTCCAGTTACATTATGTATGTTGCTTTATCTGGGAAGATGTCTTGATGGTAGGCTTAACAGATCTTGTGAGTTGTGAATC
CCCAGTGATATTTCTTTTGAACTTGAGTGAGTTGATAATTTCTAGTGTTGGGAGTGTTTCTTTAATTTTAGTTGTCTACT
AAGTTGTACAGATGACAAAATGGCTGAGATCATATTATATTGTTAACCTGCATTTGTGTAAAATTGAAAAGCAATCCATA
ATTTAGATGCTGTAAAAATTTGCAGATTGCTGTAAAAAATGCGCAGATTGCTGTAAAAATACTGTAAAAATTTGCAGATTG
CTGTAAAAATTTACAGATTGCTGTAAAAGTTTACAGATTGTAGATTGCTGCAAAAATTTGCAGATTACAGATTGCTGTAA
AAATTTACAGATTACAGATTGCTGTAAAAATTTACAGATTACAGATTGCTGTAAAAATTTACAGATTGCTGTAAAAATGC
AGATTTGTAAATGGTAAAAATGCAGATTGCTAACATTAACAAGATTGCTAACTTTTCCATTACAATCAAGAGATCAACA
AGATTGCTAACAACTTTCAACAAGCAAAACACAATGGCATTACATCAGTTGTAACCGGTATATTGCTAACATTACATCAA
AATACTAACGACTACACCACACTACTACAACAGAGCTACACCAAACTGCTAACGACTACACACTACTAGAACAGAGCTAC
ACCAAACTACTAACGACTACACACTACTAGAACAGAGCTACACCAAACTACTAACGACTACACACTACTAGAACAGAGCT
ACACCAAACTACTAACGACTACACACTACTAGAACAGAGCTACACCAAACTACTCACGACTACACATTACAAACGATCCA
AGAAAaGAAGTTCAAACATAACTACAATACACTACATCAACTTGGCAGCTACAAAACCAACAATAATATCCCAAAAGATC
AGAAGCAAGCTTATCAATTGAAACCCTTTCAACTTCCACTTCAGTTTATTATCATCCAAGTTCTTCAAATTTAGAACATTC
AATATGATGTTCCAACTCCAAGTTTGAAACTTTATCCTCCAAATTTGAATTTTCAAAAAAAGTCATATCATTCAAGTTAG
AATCAATGTTTGGTTTATGAATTTCAATGCCACCTATTTCCTTTAGGATCTTCTTCAATCGGTTTCTTCCCTTCCGAATT
GAATCTAATTCAATCTTTTGATTGTGAGTCATCAATGACGCATGACTTGGAAGTTTACTAACGATCCAATCCAATAACCA
CAAGAGAATGAGCAAGGACGACAACATTTGAAGAATCGACGTTCACCATTCTCACGGGTCATAGCAGTAAAATATTTTGC
```

Fig. 8B

```
TATCAATCCACACTTACATGTATGAGACTCAACTTGTTGAGGAGAAGAAACAGAAGAAGATGTCAACATTGAAACAACAC
AAAATTTAACAAATCTAATGAAGAAGATGATTTTCAAAAGAGCTTCAAGAACTAACAGATGAAATTTGGGGGAAATGTTT
AGGGTTTTGTTTAAAGAAATGGGTAATGGGTGTTTTATTTGGATGGGTTGGGTATTTTGAAGATGGGTCGGGTGGATCCG
GGTGGATAGGGTGGTTTGGGTCAAACAAATTAGGCTTTAATTAATTAAATTTCCAATCAATTACAACATGCCACGTAATA
AATGAAATAATTAAATATATTTTCTAAGTAGTCTGTTAGTCAAAAGGGCAAAATAGGTCCCTAAAGGTTAACCCCGAGGG
TATTTTGAGGCCAAAAGGTAAACGAGGGGTATTTTTGTACCAATTCTGATACTATAAGGGTATTTTAGACCCTTCTCCCT
TTTTTTTTTtAACTTTAATGCGACACTTTTTCATATTTTATATTTTCCTCAAATTATATCTTTTTTTTtCTTTTCCTTGT
TGTAAGTCCTGGTGAAATAACCTCGTGATACCACAAGGATTTGAAGATTACACTCACAACAAAATAAAATATTTTTTGA
TTCAAGCTCTAAAAATGAAAAAATACTGGTAGAAAGTATTTCTTTCTTAAACTAGCATTACGTGATATGAATTTGAATTA
GTCTAATCAATAAATTTAGAACAAAACATTCCTTACCAGGAAAGTGAAGAGATTTTGACCATTCCACTAGAGTCATTATG
GTGATGTCTCACCACCAAATCAAAGTTTAATAAAAATCGAACCGAATAACCGAACGTCCACTCGGACCAATTTTTTTTTT
TTTGAGAGGATCAAATCGCATAAAAGCCTAATTTTCATGTAACATACAAATTGAGTCTCATAATATCCCAAACTCACAGC
CATGAACCCAAATTGGGTAAAGTTTTGCAAGACATTTTAGGAAATTTAAAAATGGCGTCTGGATATTTAATTTTTAAAA
ATATCGTGTGATTGATTAATTATACTAAAGATATTTGCTTAGTTACGTGACTTTTCAAAAAAaGAAAAaGAAAAGTACAT
TATCAATCATCAGCCACAAAATATTAAGTCACAGTTTGTTTCTTAAATTCCATATCGAATTAAATTGAATGACACTTAAA
TTGGAACGAATGGTGCAATTTCCTTCGACTATTCAACTAGTATCTTATCCACAGCATGTGTTGATCCTTTTTCTTTCGT
TTTTCATTTACTTGACATTATTAGGAGACTTGGCAGTGGACTCCAACTATTCTAAGCTGACCTTTCTTTTCCTTTACCAA
TTATCTTCTTCTTTCTAATTACTCATTCTGATCAGTTTTTTGTAGCTACTGAAAAAGAAATGGCTGAAATTCTTCTTACA
GCAGTCATCAATAAATCTGTAGAAATAGCTGCAAATGTACTCTTTCAACAAGGGAGCCGCTTGAATTTTTTGAAAGAGGA
CATCGATTGGCTCCAGAGAGTACTGAGACACATTCGATCATATGTAGACGATGCAAAGGCCAAGGAAGTTGGAGGCGATT
CAAGGGTCAAAAACTTATTAAAAGATATTCAAGAATTGGCAGGTGATGTGGAGGATCTCTTAGATGAGTTTCTTCCAAAA
ATCCAACAATCCAATAAGTTCAAAGGCGCAATTTGTTGCCTTAAGACGGTTTCTTTTGCCGATGAGTTTGCTGTGGAGAT
TGAGAAGATAAGAAGAAGGGTTGCTGACATTGATAGTTTAAGGACAACTTTCAACATCACAGATACAAGTAACAACAATA
ATGATTGCATTCCAATGGAACAGAGAAGAAAATTCCTTCATGCTGATGAAACAGAGGTCATCGGTTTGGATGATGACTTC
AACAAGCTCCAAGACAAATTGCTTGTTCAAGATTTGTGTAATGGAGTTGTTTCAATAGTTGGCATGCCTGGTCTAGGAAA
AACAACTCTTGCCAAGAAACTTTATAGGCATGTCCGTCATCAATTTGAGTGTTCTGCACTGGTCTACGTTTCACAACAGC
CAAGAGCAGGAGAAATCTTACTTGACATAGCCAAGCAAGTTGGACTGACGGACGAGGGAAGGAAAGAACACTTGGAGGAC
AATCTAAGATCACTTTTGGAAACAAAAAGGTATGTTATTCTCTTAGATGACATTTGGGATACTAAAATCTGGGATGCTCT
GAACCGTGTCCTTCGTCCTGAATGTGATTCAAAAATTGGCAGTAGGATAATTATCACTTCTCGATATCATCATGTAGGCA
GATACATAGGAGAGGATTTCTCGCTCCACGAGTTGCAACCCTTAGATTCAGAGAAAAGTTTTGAACTCTTTACCAAGAAA
ATCTTTATTTTtGATAATAATAATAATTGGGCTAATGCTTCACCTGTCTTGGTAGATATTGGTAAAGTATAGTTCGGAG
ATGTGGAGGTATTCCATTAGCCATTGTGGTGACGGCAGGCATGTTAAGGGCAAGAGAAAGAACGGAACATGCATGGAATA
GAGTGCTTGAGCGTATAGGTCATAATATTCAGGATGGATGTGCTAAGGCATTGGCTCTGAGTTACAATGATTTGCCCATT
GCATTAAGGCCATGTTTCTTGTACTTTGGTCTTTACCCCGAGGACCATGAAATTCGTGCTTTTGATTTGACAAATATGTG
GATTGCTGAGAAGCTGATAGTTGTAAATAGTGGCAATGGGCGAGAGGCTGAAAGTTTGGCGGATGATGTCCTAAATGATT
TGGTTTCAAGAAACTTGATTCAAGTTGCCAAGAGGACATATGATGGAAGAATTTCAAGTTGTCGCATACATGACTTGTTA
CATAGTTTGTGTGTTGACTTGGCTAAGGAAAGCAACTTCTTTCACACCGAGCACAATGCATTTGGTGATCCCGGCAATGT
TTCTAGGCTGCGAAGGATTACATTCTACTCTGATAATAATGCCATGAATGAGTTCTTCCGTTCAAATCCTAAGCTTGAGA
AGCTTCGTGCACTTTTCTGTTTCACAAAAGGAGACTCTTGCATATTTTCTCATTTGGCTCATCATGACTTCAAATTATTA
CAAGTGTTGGTTGTAGTCCAGCCTCGAAAAAATTATGATTTCAGCATTAGCCAAATCAAAATTGGGAACATGAGTTGCTT
ACGCTATCTGCGATTCGAGGGGGATATTTATGGGAAACTGCCAAATTGTATGGTGAAGCTCAAACACTTAGAGACCCTAG
ATATTAGTAAAAGCTTCATTATTAAACTTCCTACTGGTGTTTGGAAGACTACACAATTGAGACATCTTCGTTCTAATGGT
TATAATCTAGCACCTTACAGTTACTTTTGTATAAGCCCATTTTTTCCAAACGTGCCTCCTAATAATGTACAAACTTTGAT
GTGGATGGATGGTGAATTTTTTGAACCGAGATGGTTGCACCGATTTATCAATTTAAGAAAACTGGGTTTACAGGAAGTAT
CCGATTCTACCATTAAGAAATTATCAACATTGAGCCCTGTGCCAACGACACTGGAGGTTCTAAAGCTCAGCTCATTTTTC
AGTGAATTGAGAGAGCAAATAAACTTGTCGTCGTATCCAAATATTGTTAAGTTGCATTTGAACGGAAGAATTCCCTTGAA
CGTCTCTGAATCATTCCCTCCAAATCTTGTCAAGCTTACTCTTTGCAACTTGATGGTAGACGGTCATGTAGTGGCAGTGC
TTAAGAAATTACCCAAATTAAAGATACTTACATTGCATAGGTGCAGACATGATGCAGAAAAAATGGATCTCTCTGGTGAT
GGTATAGCTTTCCGCAACTTGAAGTTTTGCATATTAAAGATCCAGTCTGCTTGTCTGAAGTAACGTGCACGGATGATGT
CGGTATGCCTAAATTGAAAAAGTTATTACTTATAGAAAGAACTGAATTCCAACGTTAGGCTCTCCGGAAAGACTTGCAAAGC
TGAGAGTATGAAAATCCCAATGTGTCAACAGGTTAGTTATTTACTTTTAATATCTCAAAATAAGCTCATTTTTTATTAAT
TAATTCATGAACTAAATATTTTATGTCTAATAAATTGCAGATGCTTTTCAGAATGATTATGTCTTTGCTGGAGAGCATCT
TTTGATGCCTGTTTGTATTTGTAATAAATAAATTAAATGTTTGATTGCTTCTTCAAGTTGATGTATTTGTGGCTTCTAAT
TTGTAAAATAAATATATTTATTCATCTATTTATGGTCTTATGTATATTTACCTTTGGAATTAGCAGTAGCTTAATTAGTT
TCTTTTCTTCTTCAAGAATCAATGCTCACAATTCTAGTTTTAAACACGTTACTAAACTTACATTCTAAGTATTCTAATTA
ACTTAGTCCTTCAATTCTAAACTTGAAACTTTTAGACTCTAGAGCTTCTTTCCAAAATTTTTAATCTATGATCATTAAAT
TCATCGCACGTCTTGTCAATCAATATTATGTCATCTAACATCCGAAAATAACATACACTGGCACTTCACTTTGGATATAT
CGTGTCGATTGGTCCATCATTAAGACAAAAAGGAACATGCTAAGGGTTGATTCCTATGCAATTCCATCCTAATCGAGAAG
TGTTCTGACTCACTCCCACAATTCTAATCCAAATTTTAATTCCATAGATAATGTGGTAAATCAAATTAAATTACAATTAA
TAGGCCTTTTTTTtCTTTTTAAGAAACGTCTCTCAATTTATACAAGAAATAGCTGTGTATAACATACTGACATTTTGGTT
ATACCAAAGTTCTCCTTACATTTTACTCCTTCCTTTCCGAAATATTCTGATGACTCGCTTTTTGAGAGTCAAATTATATG
GACTTTAATCAATATCTTAACATGTATTGTTTTAGGATCATATTATGTTATTAAATTTTAATTATATGAGGGGGGATTA
TCATATATAGTACTATTTTATAGTTTTTAAATATTTAATTTAACTAATCAAATTTAACTTCAAATATGAGTCAAATTATA
```

Fig. 8C

```
AACACAACAACACAATTATCAGGGATGCAATCTACCACTGAGCTAATAGCCCGTTGTGCGAGCCTCCCACTGGGGGCCGC
TAATATTGTTATATACCTCTACAAAAGGCAACTATTTGGGGGTGGTTGAAGTAAATATTGTAGTGGGATGACCTAAAAAA
aGTGCATATTACAGTTGTCTAGTTATATGGTACACTATATATAGTATTATATTATGTGCAATTCTGGTAAAATATTTAAT
ATTGCACCTCTAAAATTGGTACGTATATTTATTTACACTTTCATCTTTTGCAATGAAGGAGATGGCTTAAATATGGGTAA
TGGATAACATGCAACTGGGGTTTGCATATATCTGATAAGGTTGTAGTAGAATGGTAAATAACTAAATATCCATCTATTTT
TAATCAAAGATTTTGGATTTGAGTTCTCTTTTGTACGAAATTGTCTTCGTTAAAAAGCACTTCACCTCTCAATCTGGGAC
TCCTGACGCGAAATTGGATTTAGTCAGACTTCAATGAGGGTACTAGCCACCGGGTGAGAAaCAAAAAAAAATGCATTTAC
TTGTCATGTTTCGCAAAAGTTAATTTGATTAATTTTCGGAGTCAGGTTGAATTAAATTAATTCAATATTTTAAATTTGGA
TGTTCAAAAATTATACTATCAATCTTTCTCATATTAATATAATGAAAAATATATTTTAAAATGTAAATCAAAGTTTATGT
GGACAATAAAACGGAGTGTGTAATTTATTGCAAAATGAATCACTCAACTACCTCAATGTGGACAATAAAACGCCATAGAT
AACTTGCAATGAATTTCTCCAATTACCTAATTTAAAGTCTTGCCACCTATGTATATTTTTTTCTCCATTAATTATAAGA
CTTATTAGCTCTTTAATTACTTAGATAACGACTACTCTTTTATTCCATTTTATATATGGAAAAATTGAATTTCTATATAA
GATAAGTTTATAAAATATTTTTAGCTAGAGAACTACTCTTGCAGTTCAAATTAATGTTAGCGGTTTTAGAATCTAAAATT
GTTTTATAACAGAGATCTCGAGTTCAAATTTTAAGTGTAAATTTACGTTTAATTAATAGGAAGAGTTCTACTTCAAAATG
GAATTGTCTCGCATAAATCCAGATTATTCGAATTCTAAAATGAGTATGGTATATCACATGGAAAAATAATATATATCTTG
AAATATAGGATAATAGGAGTGGATAATTTCATGTAAACCTTCTTAATTTTTCCTAGTAGGGACTAGAAAATGAGCAAAAG
TGGCATCTCAATCATGCAAAAAGTTAATTAAAAAATAAAATAAATTAAGAGCCTTGTGCACTAAATTCTGACTAGAACAG
AATTATAAGATTTTATAGTACGTAATCTTATTTTATATTTCTATAAAAAAATATTTTCATAACTCGAATTTATATTGATC
TTCCGATAACACATAATCAATTAATTAGTACACAGTACTTCATTCCTTAAAGTTTTTGTCATGATGAAAGATTTTGAAA
GTTTTGAATTCTGTCCAAATCCTGAGGACAAAAACTTCTATATCACACAGCAGAAAAAAATAAAATTAAAGAAACAAAAA
TAAAATAAGAACAAGAGTGAGTATGTATATAGCTGTGCACTCGTTATAATGATATTTCATTATAGCAACCTGATTTTTTT
CATAATCAATTTTTCATGTTATATTTACTTATAACCACAGTGTCATTCATTATAGCAGTAGACTTTTTGTAAAATTACTC
CTCTATGACAATTATACTCAATATTTATATAATAATATTTTGTAAAAAAATATATTTATATATAAAATAAAATATTCAAATAT
TTATGATAATTATCATTAAACTAGGCAAATTTTATTAAATTTTTAGGTAATTATACAAATTATAAGTAAAACTCTCAAAC
TTAAGTAAAAATTTGGGCGAATTAAGTTATTATGACCCATGGTTTTAGCCTATATGATCCAACTTATATCAACCTAATAA
TATATGATTGGGCCATCATTTATTAACTCAGTCTATTTAGTTTTAATCAGCTCAAATATAATTCAACTCGCTCATTTAAC
ACCGCAGCTATCAATATATACACCTATTTAGTATACCATGAGCTACATAAATCATTGCTAGTTTATAATCTCACCTCAAA
AGCCTATATAAACATTTCATTGAGCCATCATTTATTAACTCAGTCTATTTAGTTTTAATCAGCTCAAATATAATTTAACT
CGCTCATTTCTCACCGCTGTCAGCTAACAATATATACATAATACACCTATTTAGTATACCATATACCATGAGCTATATAT
AAATCATTGCTAGTTTATTATCTCACCTCAAAATCCTATATAATCCATCCTCTACATAATCAAGAACATCCCAAATTGTC
TACAAGCTCCTCTACTCCCACTTAGGAAAAAAAAaTAATCCAAAAATGGTGTCTTCAAAATTAGAAGATGGTCTAATTTA
CAACATAAAATTATCCTCAGTTGGACCAGCTAGAGTAACAGGACAAGATGTTGTTTATGAGCCAAGTAACATGGATTTGG
CCGTGAAATTGCTTTATTTTTATAGTAATAATTCAGCTGACTTAGTAAATATTGGTAGAAGTATAGTTGAGAGATGCAG
AGGTATACCACTAGCCATTGCGGTGATAGCAGGCATGTTAAGGGCAAAAGAAAGAACAGAATATGCATGGAGCAGAGTGC
TTCAGAGTTTGGGTCATAAAATTCAGGATGTGCTAAGGTACTGGTTCTGAGTTGCAATGATTTTCCCATTGCACTA
AGGCAATGTTTCTTGTACTTTGGCCTTTACCCTGAGGTACTGGCTCTGAGTTACAATGAGAGTTCCCATTGCTAATGCTT
TTGATTTGACAAATATGTGGATTGCTGAGAAGTTGATAGTTGTAAATAGTGGTAATATGCGAGAGGCTGAAGATTTGGTG
GAGGGTGTCCTTAATGATTTGGTTTCTAGAAACTTGATTCAAGTTGCCAAATAGAAATATTCGCATACATGACTTGTTAC
ATAGTTTGTGTGTGGACTTGGCTGAGGAAAGTAACTTCTTTCACACTGAGCACAATGCATTTGGTAATCTCCGCAATGTT
TCTAGGGTGCGAAGGATTACATTCTACTCTGATAATAATGCCATGAATGAGTTCTTTCGTTCAAATCCTTATCCTAAGAA
GCTTCGTGGACTTCTCTGTTTCACAAAAGACCGTTGCATATTTTCTGAATTGGCTCATCTTAACTTCAAATTATTGCAAG
TGCTGGTTGTAGTCATGTCTCAAGATGGTTATGGGGTTTCACTATGGCAGTGCTTAAGAAAATTACCCAAATTACGAATACT
CTATCTGCGATTGGAGGGGGTAATTAGCGGAAAATTGCCAAATAATATTGTGAAGCTCAAATGTCTAGAGGCCATAGATA
TTGGAGTGGGCGACATTGAACTTCCTTGTAGTGTTTGGGATTTTAAACAATTGAGACATGTTCATTGTAGAGAAGAACTT
AAGGATTTCTTTTCTATAAGCCCAAACATGTGGCTCATGATAATCTACAAACTTTGATGTGGATGGATGATAAATTTTTT
GAGGCGAGATTGTTGCACCAATTGATAAATTTAAGAAAACTGGGTATAAGTTCAGCATCTGATTCTACCATTAAGATATT
ATCAGCATTGAGCCCTGTGCCAACAGCGTTGGAGGTTCTGAAGCTCAAATTTTGCAATGAATCGAGTGAGCAAATAAACT
TGTCGTCGTATCCAAATATTGTTAAGATGCATTTGAACGCAGCAATGCGCTTGAACTGTGAAGCATTCCCTCCACATCTG
GTCAAGCTTACTCTTGTCTACTTGACGGTAGACATCATGTAGTGGCAGTGCTTAAGAAAATTACCCAAATTACGAATACT
TAAAATGGTTGTCTGCGAACATAAAAAAGAaGAGATGGATCTCTCTGGTGATGGCTTTCCGCAACTTGAAGTTTTGCATA
TTCAAAATCCACTCTGGTTGCTTGAAATAATATGTACGGATGATGTCAATATGCCTAAACTGAACAAGCTATTACTTGTA
GATACCAAATGCGAGAGGTCAGTATGTCTCTCCGATCGTCTCGCAAAGCTGAGAATATGAAAATCCCAAGCTTATTTTCT
ATTTAATTAATTCATGAGCTAAATATTTTATGTCTAATAAATTGCAGATGCATTTCAGAATGATTTAACTCTTCTTCTGA
TGCATCTTTGTATTTGTAATTAAATAAATAAAATGTTTGATTGCTTTCTTGTGCCTTGTGATTTGTAAAAGATATATGAA
GTAGTAAGGGGTAGAGATAAACATTTGATATATATGTACGGCTGAAGTTAGTGAATTATTATTGGTTGACACAATAATCC
AATATTAAAAATAAAATTGAACCAATAACCCACTATTTTTTTTTtAATAAAATCATTTAAAAATCGTTGACCCTATAACC
CAAGAGGAATAAATCAATAGTATTTTTTTCGATTCAATTTACATACAAAGGGACTTAGTTTTAAACTAAACAATGAATTT
ATGTATGCTCCACTATGATTATATAAATTAACTTTTCTAATGTCAATTAGGAAATAAACTTGCAACGCACGTTCCTAGAA
CTAGTGTATATATATATATATATTCTAGTGGGATAATCATATACTGCTTCAATCTGCTGACGACTCTAAAAATTCTTT
GTTCTTGTTTGAAAATGAAATATATAATAAAGATTTAACAATTGTTTTAATGAACTGAAATATAATCGGACGAAGGAGAT
TCCAGAAGCTTCGGTGTGAACTCATCTTTGCCATTGAATTTTACGCGTAGTACTGCCTCAATTGTCTGACCTTCAACGTG
GATCCAAGATTGTTATTAACGGTATCAATGGTTGTAGTAAAAAAaTTAATTTGAGGTTAATAGCACAAAAACACACAAC
TTCAAGGAACTTTCGTAATACCTTAACCACTACACTAAACCTTTAACTTGTGTCCAGAGATGTTAATACTTGTATATATA
```

Fig. 8D

```
TTTATTTAAATCAAAATTTGACCTCTATATACAGTGTAATTTTCCGACAAAGGGGTATGGGTAAGGGCGGCGCCCCTGCA
TTCTTGAAAACGAAATACCAGCTAATATGATTAAGAAACGATGAATTATTGTATTTAATATGAACAGAGTAGTTGCTTCT
GTCCATTTGTTCTTTCATTTTCATCTACTTGACATTATTATTATTAGTAGTAATTACAAGACTTGGCCGTCGACTCCAAC
ACCTAAAGCAAATAGTGCATCTTTCTTATCCTTTTACCAAAAATTGATCATCTTTTTCTCTTACTTTCCCTTGCTAATCC
TCACATTTAGAAAACAGAAATTCAAGGAAAAAAGAGATGGCTGAAATTCTTCTCACAGCAGTCATCAATAAATCAATAGC
AATAGCTGGAAATGTACTCTTTCAAGAAGGAATGCGTTTATATTGGTTGAAAGAGGACATAGATTGGCTCCATAGAGAAA
TGAGACACATTCGATCATATGTAGACGATGCAAAGGCCAAGGAAGTTGGAGGTGATTCAAAGGTCAAAAACTTATTAAAA
GATATTCAACAACTGGCAGGTGATGTGGAGGATCTCTTAGATGAGTTCCTTCCAAAAATTCAACAATCCAATAAGTTCAA
AGGCGCAATTTGTTGCCTTAAGACAGCCTGCATCCCTTGTGCCAATGAGTTTGCTATGGAGATTGAGAGGATAAAAAGAA
GGGTTGCGGACATTGACCGTGTAAGGACAACTTACAACATCATGGATACAAATAACAACAATGATTGCATTCCATTGGAC
AAGAGAAGATTGTTCCTTCATGCTGATGAAACAGAGGTCATCGGTTTGGATGATGACTTCAATAAGCTACAAGCCAAATT
ACTTGATCATGATTTGCCTTATGGAGTTGTTTCAATAGTTGGCATGCCCGGTTTGGGAAAAACAACTCTTGCCAAGAAAC
TTTTTAGGCATGTCCGTCATCAATTTGAGTGTTCTGGACTGGTCTATGTTTCACAACAGCCAAGGGCGGGAGAAATCTTA
CATGACATAGCCAAACAAGTTGGACTGACAGAAGAGGAAAGGAAAGAAAACTTGGAGGGCAACCTACGATCACTCTTGAA
AACAAAAAGGTATGTTATCCTCCTAGATGACATTTGGGGTGTTGAAATTTGGGATGATCTGAAACGTGTCCTTCCTGAAT
GTGATTCAAAAGTTGGCAGTAGGATAATTATCACTTCTCGAAATAATAATGTAGGCAGATACATAGGAGAGGATTCCTCG
CTCCACGAGTTGCAACCCTTAGATTCAGAGAAGAGTTTTGAACTCTTTACCAAGAAAATCTTTACTTTTGATAACAATAA
TAATTGGGCCAATGCTTCACCTAACTTGGTAAATATTGGTAGAAGTATAGTTGAGAGATGTGGAGGTATACCGTTAGCCA
TTGTGGTGACCGCAGGCATGTTAAGGGCAAGAGAAAGAATAGAACGTGCATGGAACAGAGTACTTGAGAGTATGGGTCAT
AAAATTCAGGATGGATGTGCTAAGGTATTGACTCTGAGTTACAATGATTTGCCCATTGCATTAAGGCCGTGTTTCTTGTA
CTTTGGCCTTTTCCCTGAGGACCATGAAATTCGTGCTTTTGATTTGACAAATATGTGGATTGCTGAGAAGCTGATAGTTG
TAAATAGTGGCAATGGGCGAGAGGCTGAAAGTTTAGCGGAGGATATTCTAAATGATTTGGTTTCTAGAAACTTGATTCAA
GTTGCCAAAAGGACATATGATGGAAGAATTTCAAGTTGTCGCATACATGACTTGTTACATAGTTTGTGTGTTGACTTGTC
TAAGGAAAGTAATTTCTTTCACACTGAGCACAATGCATTTGGTGATCCCGGCAATGTTGCTAAGGTGCGAAGGATTACAT
TCTACTCTAATAATAATGCCATGAATGAGTTCTTCCGTTCAAATCCTAAGCCTAGGAAGCTTCGTGCACTTTTCTGTTTC
ATAAATGACAGTTGCCTATTTTCTCATATGGATCATCTTAATTTCAAATTATTGCAAGTGTTGGTAGTAGTCATATCTAA
TAATGATATACGGAGTGCCAGGAGAATCCCAAACACGTTTGGGAACATGAGTTGCTTACGCTATCTGCAATTCGAGGGGA
ATATTTATGGGAAACTGCCAAATTGTATGGTGAAGCTCAAACATCTAGAGACCCTAGATATTGGTAAAAGCTTCATTAAA
CTTCCTACTGGTGTTTGGAAGTTTACACAATTAAGACATCTTCTTTATAAAGATTATAGTCAGGCATCTAACAGTTGCTT
TTCTATAAGCCCATCTGTTCCAAACGTGTACTCATTGCCTCCTAATAATCTACAAACTTTGATGTGGATGAATGATAAAT
GTTTTGAAGCAAGATTGTTGCACCGATTGATCAATTTAAGAAAACTGGGTATAGAAGAAGTATCTGATTCTACGATTAAG
ATATTAGCAGCATCGAGCCCTGTGCAACCGGCGCTGGAGATTCTGAAGCTCGAATTTTCCAGGGACATGAGTGAGGATAT
AAACTTGTCGTCCTATCCAAATATTGTTAAGTTGCATTTGAACGGAAGAATGCCCTTTAACTTTGTAGCATCATTCCCTC
CAAATCTTGTCAAGCTTACTCTTGTCGACTTTGGCGTAGACAGTCAGGTAGTGGCAGTGCTTAAGAAATTGCCCAAATTG
AAGATACTTAAAATGGTTTGCTGCGTACATAGTGAAGAAAAGATGGATCTCTCTGGTGGTGATAGCTTTCCGCAACTTGA
ATTTCTGCATATTAAAGAATCATTATGCTTGTTTGAAATAACGTGCATGGATGATGTGAGTATGCCTAAATTGAAAAAGC
TATTACTTATGGATACCATTCCCAACGTTAGGCTCTCGGAAAGACTTGTAAAGCTGAGAGTATGAAAATCCCAATGTGTC
AACAGGTTAGTTATTTACTTTTAATATCTCAAAATAAGATCATTATTTATTTATTAATTAATTCACGAACTAAAAATTTT
ATGTCTAATAAATTGCAGATGCTTTTCAGAATGATTAAGTCTTTGGTGGAGACCATCTTCTGATGCCTGTTTGTAATAAA
TAAATTAAATGTTTGATTGTTTTTCAAGTTGATGTATTTGTGGCTTCTAATTTGTAAAATATATTTATTTATCTATTTAT
TGTCTTATGCATATTTACCTCGAATTAGCAGTAGCTTTAGTTTCTTTTCTTCTTCAAGAATCAATGCTCACAATTCTAGT
TTTGTAAAGTAATATATTTAGGAAAAATCCTTTTGGTTTGAATGGTATTTTACTTATGTACTTATTTTATCTTTTTGAAC
ATTTTTATCTTTTTAACTTTAATACCTTTTAATTAAAAAAAaTAGAAAAAAGATCAATTTATTTTAAAATAAAAAGGATA
TTATAATTTTTAAAAATTTCTAGCCAAATTGTGGCCAAATTTTCTAGTCATTTAGCATTACTCATATATTTATTGTCTTT
ATGTATATCTACCTTGACACATGCACATTTCTTTATGAGATCGACCCCAACCTTTGTTGAATTTATTATTGCTATGAGTC
TACTATTTACATTTTATTTTAAAGTGTAGAATTGGCCATGATCAGAGTATAACTCCAGCATTCAATAATTTGAAATATAA
AATACAAATATAGTTTAATCAATTTTTATCTATGTATTTTGGTTTTATTTATGTCAAATACAAGGTATGCATCCTTAAA
GATTAAAAATCTACACATTTCATCCCAAACTATAAAATATTTCAACATAAAAGTTTTAAAATTCATCTAACAAGGTAT
CATGAGGAGCTGGCCTTCCTAATAATGACTTTTGTTTGCTAAAGAATTTCACAAAATTAAAAaTCACTCACAATCTGTCA
CGCCCCGAGCCTACACCCTGGACGGGACCGGCACCCGAAGACCATTTCTAGCCCCAAGCGAACCCTTGGCCTGGCTTTCT
TAACTCAGTGGAAACCTAACCCAACAGAATAACTCAATGCTAATGCAAGGTTAGAAAACAACTTAACTTATAAAATATGG
CCATAAAGGCAACTCGAATCTCAAAATAGAATATTTACATATATATATAGATGAGAGACTCAAAACTAACGGACTGACTG
TCTGTCTATGAAGCCTCTAAAATACTGAGATGGATGTTGGGACAGACCCCGCAACATCCTAATAAAACAAAAAACTAAGA
ACACAAAATAATTGAGTCCTCCGGAATGCAAGGAGGCTCACCACTGACTCTGGAGTGCTCAGCTGGATCAACGACGTGCA
GGATGCTGATCCGGGGCACCTGAATCTGCATCATCAAACGATGCAGGCCAACTGGCATCAGTACATGGAAATTACGAGTA
TGCGAGCTGGAAAACTAAGCAACAAAGGCTAGAAGGAAATCTGGAAGAAACTGAATAGCTTACCTGGCTCAACTCAACTC
AACCTGACTGACTTCTTTCAATATAAGGCAATTTAAAACAAGTGCGATATAAAGAAAGACTGTTTAAAACATGCTATAAA
CTCTGTGTGTATACAAGGATACAATAAGCCTGAAATGTATATAGAAATACAATGAACTGATGTATATAAAAATACAATAA
TCTCTGTGTATGAAAATACAATAATTGCTGTGGGAGTTTCTCTAACCGACAACCATCACATAAGAGCTATAGTGATGATA
CAGCGATCGACCTCACGCTGCCAGAGCATCTTATACCTGGCCAAAGGTACAAGACCTGAACTGCCTAATGGATCCACTAG
TTTAATCTGAAAGGATTTATCTAAAAAGTATGATCCTTTTCTACCCATGGTGGCTAACATGGTTCTATGGGGCTGTGG
GTTCTTTGAACGCTCCCCCAATTCGGTGCTCGATACTACTCCCAAAAATGTACTGGCTCTTATGTTTTAAAACATATTT
CTTCCTGCTGATATGAGATAATTACTCAAAAACTAGCCCGAAGGCTCTTTTGGAAATCTCAGTTTCCAACCTTGTTTAAA
```

Fig. 8E

```
TGTAAAAACATTTCTTTAAAACTTCTTTGGGAATACATAGTTCCCTAATAACTTTGAGAAAAGAACTCAACTTTAAACTC
TTTACTTTACTTGAACTCTTAGCTTGATGTGAAACTCTTAACTTTTGACTTGACTTGAAACTCAATACTTAACTTGGAAC
TTGAGCCTTAGAATGAAGTTAAAACGTTCAATGAAGACTCTTAGAAAACCTTAAAGACTTGCTTTGACTTACTTACTTCT
AAGCTTGACTTCACTTGACTTGGAAACTAACTTCACTTGAATTGGAAACTAACTTCACTTGACTTGTAGTTTTACTTGAC
TTTTAGAAGTACCTTGGAGTGTTGGAAACAACTAGGAAATATAGGTATAATACCTAGGAACATGTATGAAAAAAATGGTG
AATGAAAGGGAAGGATTGGTGTCCTTGGCACTAGGAGAGGTGCGACAGCCCAGCCCCTTTTTCCCCAAAAAATCCGACTT
TTTCCCCTTGTTTCTTTCCAATTCTAAACCCTCTCAACCTCAAGGTTTCAGCAGCAACACATAGAATCATAAAGATCCTT
ATTATACAATAGATTCAACTCAAAAATCACAGCCAGAAATCTGTACTAAACCAGCAAGAACTTCAACACAACACCACTAC
AACTTCAACAACCAATAAATCTTTTCTTGGAATTAAAAATGAGTTGGTGTGTGGGGGTATGAACCAACCAATACTAAGGA
TCATCAATCTCTCAACATACAATAGATCACAACTCAAATACACAGCCCAATCCTGTCCCACAACCAACAATAACTTCAAC
AACACAACTAACAACATCAACAACAACTAACAACTTCAACAACAAATCCAATCTTTTCTCAAACCATAAACATGAGCTTG
GTGAGTGGGGGAAAGGATCAACCCACACAAAGAACTCACATACCTTGATAGGGATCACCCCCGACGAAAATCCACAATGA
TCTTGACGAATCTTGTTGATCTCCTCTTTCTTCTCTTCTTCTTCTCCTTCTTCTCTTCTTCTTCTCTTCTTCACCCTCAA
GAACCCTAACTCTTTCTCTTTCAAAATGGGACAAAATGATCCAAAGATCAGCCTAATACAACAATATAAGCTCAAAAGAA
ATGATTTGTGAAAAGACTAAAATGCCCTTAAATTTCCGGACGGACTCCTTGCCAACTGCCCCAACTTTCAAAGGGCATAA
CTCGCTCATACGAACTCGGAATCGAGTAAACTCGGTGGCGTTGGAAATATCATTCCACAAGCTTCGAAACCATAATTGGA
AATACTCCTAACTCATCCTGATCTAGGAGTTACGACTGCTCAAAGTTGGCCAAAAACTCACTGATTTCCACACTTAGCCA
AATTTCCAGATTTTTGAACTTAGCCAAATTTTCCAGATTCTGGACTGCCAAATTTCCAGATTTTAAATTTTtCCAAAAAT
GACTATTTCCAAATTTCAAGCTTCTTCAAAGCCACTTCAAATTGTCGGATGTTACACAATCAAAGTTAGAATTCTAGCTA
TGTATATGATAAAGTCTTATAATTTAGCTAAAATCATTGTTTATGTTAAAAATTCATTGAATATATATATTTAAATA
ATTAATTCAAAATCATAAATTATTTTTTTtATAAAAAAATTTAAAGCTCATGAACTCAAAATTTTAAATTTGGATCTGCT
CACTATTGACATCCAATTTTGGCCCTCCCCGATAATAATTAATTGCCGAGCTTCTTAACTTTCAAACGATTTAGAATAAT
TAGCTTTATAAAATTTAAAATAGTTTCGAGGTTTTTAAATAATTTCAATCGATTTTCATAAGCATTTGAATAAGCAATA
TATTTCATATAATCATATATGTAGTTAGTACATCTTATAAGTATTTAAAAATCATACAAAAAGATTTATACGTTGTTAAA
ATAAATATTTTATTAACTTAGTTTCATTCGGAACTATAGTTTTAAAATTTTGAATCAATTAGTGGGTTTTTAAATTAAT
TGGTTTATTAATTAAGTTAACTATTTTATTTCAATAAGAATAAGAAGCTCACTAATTAATCACACTAATTCGTTTTATTT
AAATTTTAATCAAATTTGTCAATCGAGCTCAATTTAGTTAAACTCCAATTCCAATCGGCCACAATTGAACTCAAAAGGCC
ATATCTTAATTTGGAATATAGCATTTTTATTTATGAAATTAGCCATTTGCCTTTCAACTTTTCAAATTTCCTTAAAAGACC
ATTTTTGGGCTTGCTTCAATTTCCAGCATAACCCAACAACTCTTCAGCCCACTCTCTCTATTCTAATTCCCTTTCCTCTT
ATTTCCAGCGACCCAATCCAACCCCCGAGCCGGCCCAACTCCTTTCCAATCCTAAAGAAACTTACACGGCGTCTTCATCA
GCAACCTCCAGATGTCAACAACACAGCAGTCCAAACGCCTCAACATCACAGCGAGCACACAGAGAAATTCACGGCGATAC
ACGGCCAGACCAAGAGTCAACATTGTGAGCAGTATGTTGTGTTCTTCTTGTCCTTATCCTCGACGTCCCTTTCAGCTTAT
ACGAATCGCAGCGGGCAGCACACACGCGTTTTCTCCCCTTTCCTCTTCCGGAATGGGGTGAAATTTCAGAAAAAATGTTA
GTCTCCCTAAAAGGGTGAAAGAATTGGAAGTTTTGAAATCGAAAATGGGCCTCGAATTGAGATTCGTCCGTTTTCCCTCC
CAATTCGTGAACCCTAATCTCCTTCTATTTATTCCTTTTTCTTTTCAGTATTTGGGGGGGATTTTTGTGAGAAAAGTGGG
GAGATTTTTAGTGGAAAAAAATTTAACTTAAGGCAGCAAAATTATCTAAAATACCATACAAAATATACTTCAAGGAAAAA
CAGAGGAGATACTCTTGTTTTAGTGCTTAGGTTTGACATTATTGCCCAGACTTCTCGGCTACTGTTTGTGCTCAAGTTTT
CGTGGTGAAGGTTGTCATTTCACTCGTTTGGTCTCTGTTTCGCTGCCTGAAAAAGGTGAGAATATCGCATTTATTTCGCT
TATAGCTTTTTCCTCTTCTCAACCTTTGTGTATCTACTTCGGTCTCTCTAGTAGTTGTTTTCATTAAGATGTCTTTGTGT
CATTTTCGAAGTGATCTAGTGCTTACTTGAATATGCTTTTCTCTGTTTGTAGTCTGCTTAAGTCCTTGGTTGTTGTTCTC
GTTTTAAGCTCAGCCTATTTATTTGTTGATCACTCTGACTTTGTTTTGTCTCCAGCGGTTTTGGATAATTTTTTCTTGTT
TTGTTTATATGCGCTGAAAATGTCGATGACACTATTCTGTCACTCCTTTGTATATTCTTAGGCCTAGATTCGAAATTCAT
GCTAATGTAGATAGGCGTATATTTATTCGCTTTTCACAATCGTTTTATGTTTTAGATGATTTTGCTATGAGGCCCATATA
TTGCTTCTTCTATAGTTCTTGTTCTATCAATGGTATTATGTTTTGCTTACTAGAATGCTATCTGAAAAGAATGCTAAAAC
GTGTTCCCCTCTCTTCCCCGTCTTAATGAAGTGTAAAGATGTTGAAGCTCCTTTCCCGTTCGTATTTGTGGGTTCTTATC
TTACTTTATTAATACTGTCTTTGGTGCATGTGAAGCTTGTAATTTAATTTTAGTACCGTATGAGCCATTTGCCATTTTGC
TTAATCTTATGAGAGCATAAGGTGTTTATCCTCATTTAATTATTAGGAGTTCACTGATTACTAAGGATGAGAAGATTGTT
TATGTGCATTTATGCTGTAATAATGAGCTAAATATTTGTTAACTGTGGGCTGTTCTAGCATTTTAGTAGTCCCTTAACTT
CACATGTTTCATTTTGGAGTTTAGTCATATTAATTTATTGTAATAAGAAGCATGCTTTGACCCTCTTTATTTTTTGTTACTT
GCTGTCACTAGTATGATAATATGCCATATTGATTAGTTTATGTTATGATTGAATGTGATATCTCTGTCAGTTGATGTAAC
TCGGCATGTGACTTTGATATGGCGCTACCATGTGACTTAGTTTTACTAAATAATATGTCGTGCGGATACTCATTCTCGGT
AAAAATGCAGTAAATCTTATTAATTAGTCAATGACACCATTTTGTTTTGTATCTTAGATTTTAACATTAGCTTACACCCA
ATTGATGCCTTATTTAATTATTGTTTATAATAATTCTAATTTCTTATCATTCTTTTTTGTTGCATGTGAAATCTGTCCGG
GACCTACGGACCCTATCCTTGCATTTTTCTTTGGGCCATGGAGGCATAATTCTATTTCTATCCGAGTCTAACGGCCATTA
AAGTCGACGAACAGGTCCCGAAGTTGAAAGGAGCAACCGATTGAAAAATTTGAAAAGATTGGGCCAAAGGCCCACTCTT
AATTCATAATAGTTGTATTTCGTTACTTCTGGGCCTAAGCCCTGTTGACACCTAATTTTGACCCTCTCCGATAATAATTA
GTTTTTGAGCTTCTTAATTTTTAAACGATTTAGAATAATTAGCTTTATAAAATGCAAATAGTTTTAAGGTTATCTTAAAG
TAATTTCAGTCGGTTTTTATAGTATTTCGAATGATAAATATATTTCGTATAATTATATGCATAATTAGTATATTTTATAA
ATGTTTGAAAACCATGTCAAAAGATTTTTACTTTGTTAAAAATAAATATTTTATTTATTTAGTTATAGTTTGAATTGTGG
TTTTAGTTTTGGATTAATAAGTTTATAGGTAAATCGATTAGTTTATGGTTAAATTAATTATTTTATTTTGTTAAGATTAA
AGAGCTCATAAGTTAATTATGTTAATTTGTCTTATTTAAATTGCTAGCCGAACTTATCCCAATTAATTCAATTTGGCTAC
ATCTCTAGTCCCCGATTGGCTATGATTTAAGTCATATGGCAAAAGCTTAAGTTAATTCTCACCAATTTAATTTCATCCTT
GACCCATCTTAAATGAACAAACTTTGGACTTGCATTTGCATTTTTAACAAACTTCCAGCCTATACTTTATTCCTATCACA
```

Fig. 8F

```
CCAAAGACCCAACCCCATACGTATAGCCAAATAAGGCCCAAAATCCATCAGCCTTGTTCATCACAAATATCAGAAATAAG
TTCAGCCCATTATTAGGTTTTCATCCTTATTCTATCATTAAGACTCACAACATCTCTTCCTTTTCCTTTCTTAGGCAAAG
TTCCAATTTGTTTTCATCCCAATTCAGATTGGTTTCACCATTTTCAGCTAAGTTTTTCCTCTCTCCCTTGCACATTTAAA
GCTCCTTATTGAAAAGCTGAATTTTtCTTTTTTTTtGTTGACCAAAATTCGCTGCAACTATGGAGAAAAAGGACGATTTT
GTTGATCTCTCTCTGTCACATTTTGGACTGATCTCAACGTGCTTTTTTTTTCAAAAACTCAAACAATTTTCCATTCTCC
AATTCCCGCTTAAAAAGGTTTTGGCTATAAAGGTTCAGAAAAAATCTTCAGTAGGGGGAAAGAAATTTTTTTTtGAGTTA
GAAAGAATATAGAGAATTAGCTAGTATTAGAAAGGAAGAAATACACTCAAATCATATAGTTCCTAAAATCACAGAAAGAC
TTCCTGTTCTTGCTTGCTTCCTCTTTGTTCGTTGGAGTTCTTGGATTCACATTCTAGTGGTAGTGAAGTCACTTCCTTGC
TCGCTCTGGCCTCAGTTTCGCTGCTCCAAAGAAGGTAATGCTCTCTCCTTTGTAATGTTTTCCTTATCGTTTTTTTTtGT
TTCCAGCGTGACATCTATAGATATGCTTTGTTTGGTTTGCTAGTACTTGTCGTTGAGTTCGGGATGGTTTGCTATAATAT
GACTTCTTTAAGCAATTTCAATATAAATGGATTCATATGTCCCGAGTTTATTTCTTTGTCTCTGTCGCGTATGTTGATTT
TGGACGTCCGAACCTATATTTCTTTATTTTCAATGGCTTAAGACGTTAGAATGGGCGCTCATTTTGTTAACGTTGATGGT
ATGAGCTATTTTTTCTTAAAATGAAAGATGATTTCTCAAACTGTCTAAAATGGAAATTGGATGTTATATTACGTACTGTT
TGAGATCCCCGGGTACCGAGCTCGAATTCGCCCTATAGTGAGTCGTATTACAATTCACTGGCCGTCGTTTTACAACGTCG
TGACTGGGAAAACCCTGGCGTTACCCAACTTAATCGCCTTGCAGCACATCCCCCTTTCGCCAGCTGGCGTAATAGCGAAG
AGGCCCGCACCGATCGCCCTTCCCAACAGTTGCGCAGCTGAATGGCGAATGGCGCCTGATGCGGTATTTTCTCCTTACGC
ATCTGTGTGGTATTTCACACCGCATATGGTGCACTCTCAGTACAATCTGCTCTGATGCCGCATAGTTAAGCCAGCCCCGA
CACCCGCCAACACCCGCTGACGCGAACCCCTT
```

CLONING AND EXPLOITATION OF A FUNCTIONAL R-GENE FROM SOLANUM X EDINENSE

This application is the U.S. National Phase of, and Applicants claim priority from, International Application Number PCT/NL2011/050386 filed May 31, 2011 and European Patent Application No. EP 10164531.5 filed May 31, 2010, each of which are incorporated herein by reference.

FIELD OF THE INVENTION

The invention relates to a resistance gene isolated from S. x edinense. Moreover, the invention relates to the use of said resistance gene, for example to clone functional homologues, and the use of said resistance gene(s) in a method to increase or confer at least partial resistance to an oomycete infection in a plant. More in specific the invention provides a resistance gene that is capable of increasing or conferring at least partial resistance to Phytophthora sp. (for example Phytophthora infestans) through genetic engineering techniques or through marker assisted breeding techniques.

BACKGROUND

Late blight, caused by the oomycete Phytophthora infestans, is one of the most serious diseases in worldwide potato production. It was responsible for the Irish potato famine of the mid-19th century, resulting in the death of one million people. Although a lot of effort has been invested in controlling the pathogen, chemical control of P. infestans is still the main crop management strategy, but environmental safety is becoming more important and the pathogen is sometimes able to evolve resistance to the fungicide treatment. Therefore, introduction of resistance into modern potato varieties is the most durable strategy to control the disease.

In the last century, Solanum demissum, which is a hexaploid Mexican species, was extensively used in breeding for late-blight resistance in potato. Initially, a series of 11 R genes derived from S. demissum was described. Of these, R1, R2, R3a/b, R6, and R7 have been localized on the genetic maps of potato (Solanum tuberosum). However, these R genes confer pathovar-specific resistance and those that were introgressed into potato varieties, mainly R1, R2, R3, R4, and R10, were quickly overcome by the pathogen. Hence, new sources for resistance are required, and currently, several other wild Solanum species have been reported as being potential sources of resistance, many of which have been genetically characterized (Table 8).

Recent efforts to identify late blight resistance have focused on major R genes conferring broad-spectrum resistance derived from diverse wild Solanum species. Beside S. demissum, other wild Solanum species such as S. acaule, S. chacoense, S. berthaultii, S. brevidens, S. bulbocastanum, S. microdontum, S. sparsipilum, S. spegazzinii, S., stoloniferum, S. sucrense, S. toralapanum, S. vernei and S. verrucosum have been reported as new sources for resistance to late blight (reviewed by (Jansky, 2000)).

S. x edinense P. Berthault, a pentaploid (2n=5x=60) potato species from Mexico, is a natural hybrid between the Mexican Solanum demissum and the South American S. tuberosum spp. andigena. The pentaploid S. x edinense had been identified as an interesting source of resistance to P. infestans already in 1908 by Salaman and was included in breeding programs by Brioli in 1914 (Pavek et al. 2001; Toxopeus 1964). It was named after the Edinburgh Botanic Garden (Glendinning 1983), where its hybrid characteristic was first described. It has been used in breeding programs and has revealed good field resistance to P. infestans (Van Soest et al. 1984). Two functional R genes have been cloned from one S. x edinense genotype (edn151-3): Rpi-edn1.1 and Rpi-edn1.2 also known as R2-like (Champouret 2010). They were identified by allele mining of the R2 family. Both are located in the R2 cluster on chromosome 4. Both R genes recognize AVR2 (Champouret 2010; Lokossou et al. 2009) and their resistance is not effective against all P. infestans isolates, including IPO-C (Lokossou et al. 2009).

To date, not only from this species, but also from other Solanum species late blight R-genes have been cloned, like the allelic genes RB and Rpi-blb1 on chromosome 8 and Rpi-blb2 on chromosome 6 (Table 6) of S. bulbocastanum. Recently, also an Rpi-blb3 resistance gene has been isolated (WO 2008/091153). Also a resistance gene of S. chacoense has been characterized (EP 09170769.5). Although the initial results obtained with RB and Rpi-blb1, -2 and -3 are promising, there is a further need for additional R-genes, especially because allele mining of these genes in S. bulbocastanum genotypes revealed that natural stacking of Rpi-blb1, and -3 in a single genotype occurs at relatively high frequency (Lokossou 2010). S. venturii is another example of the presence of several R genes with different specificities in a single genotype (Pel 2010). Stacking several R genes in a single genotype appears to be a feasible strategy to achieve high level and durable protection against potential pathogens. Pyramiding of R genes is still controversial and it is not known whether it is a durable approach (McDowell et al. 2003; Pink et al. 1999; Pink 2002). The pyramiding of Rpi-ber1 (Rauscher et al. 2006), an R gene with a strong effect, and Rpi-mcd1 (Tan et al. 2008), an R gene with a weak effect, revealed an additive effect on the resistance level (Tan et al. 2010). Observing natural pyramiding of R genes strengthens the idea that plants can benefit from combining individual R genes, even including some with weaker effect (Pink 2002).

SUMMARY OF THE INVENTION

The invention now relates to an isolated or recombinant nucleic acid sequence comprising a nucleic acid sequence encoding the amino acid sequence Rpi-edn2 of FIG. 4 or a functional fragment or a functional homologue thereof.

In another embodiment, the invention relates to a vector comprising a nucleic acid sequence according to the invention. Further comprised in the invention is a host cell comprising a nucleic acid according to the invention or a vector according to the invention, wherein said host cell preferably is an Agrobacterium cell or a plant cell.

In another embodiment, the invention comprises a plant cell comprising a nucleic acid or a vector according to the invention. Said plant cell preferably is a cell from a Solanaceae plant, more preferably Solanum tuberosum, more preferably a tetraploid Solanum tuberosum. Also the invention relates to a transgenic plant comprising such a cell and a part derived from such a plant, more preferably wherein said part is a tuber.

Also part of the invention is a protein encoded by an isolated or recombinant nucleic acid according to the invention or a functional fragment or a functional homologue thereof, preferably wherein said protein has the amino acid sequence of Rpi-edn2 as depicted in FIG. 4.

Further disclosed in the invention is an antibody that (specifically) binds to such a protein.

In yet another embodiment, the invention relates to a method for providing at least partial resistance or increasing resistance in a plant against an oomycete infection comprising providing a plant or a part thereof with a nucleic acid or a vector or a host cell or a protein according to the invention. In such a method said plant preferably is a plant from the Solanaceae family, more preferably Solanum tuberosum. Also preferred is such a method wherein said oomycete comprises Phytophthora, preferably Phytophthora infestans.

In still a further embodiment, the invention relates to a binding molecule capable of specifically binding to a nucleic acid according to the invention or its complementary nucleic acid, preferably wherein said binding molecule is a primer or a probe.

In yet a further embodiment the invention comprises a method for selecting a plant or plant material or progeny thereof for its susceptibility or resistance to an oomycete infection, said method comprising the steps of testing at least part of said plant or plant material or progeny thereof for the presence of absence of a nucleic acid according to the invention, preferably wherein said testing is performed with a primer or a probe that specifically binds to said nucleic acid, or where the testing involves detecting the presence of one or more of the markers of Table 5 and 7, or wherein the marker comprises part of the sequence of the Rpi-edn2 gene as depicted in FIG. 4

Further, the invention relates to a method for breeding a resistant tetraploid plant, comprising
a. using gametes of a polyploid plant that already contains a nucleic acid sequence according to the invention in a cross with gametes of a tetraploid plant; and
b. selecting the offspring of said cross for the presence of said nucleic acid sequence.

In another embodiment, the invention comprises a marker for marker assisted selection in plant breeding to obtain resistance against oomycetes, wherein said marker is chosen from the markers presented in Table 5 and 7, or wherein the marker comprises part of the sequence of the Rpi-edn2 gene as depicted in FIG. 4

LEGENDS TO THE FIGURES

Figure 1:
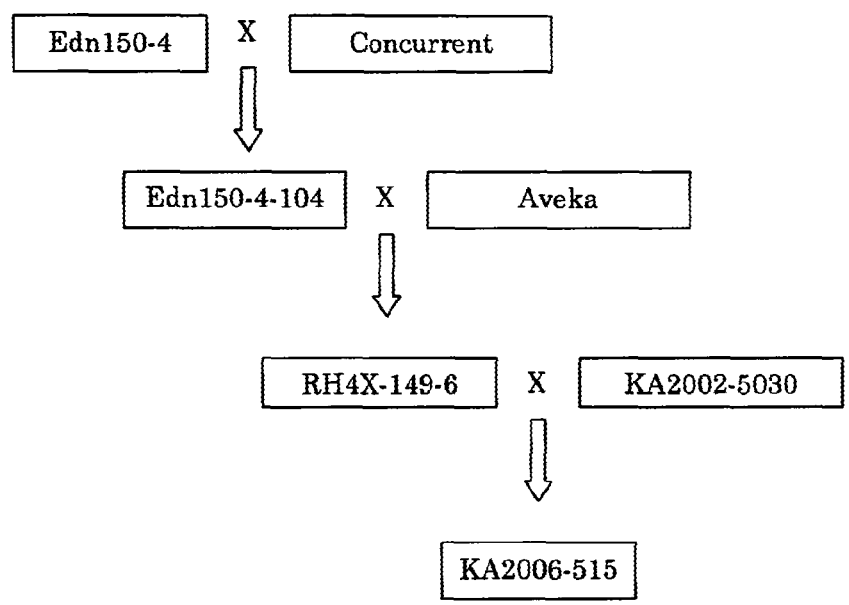

FIG. 1. Pedigrees of the genotypes used for mapping and cloning of Rpi-edn2.

Figure 2:
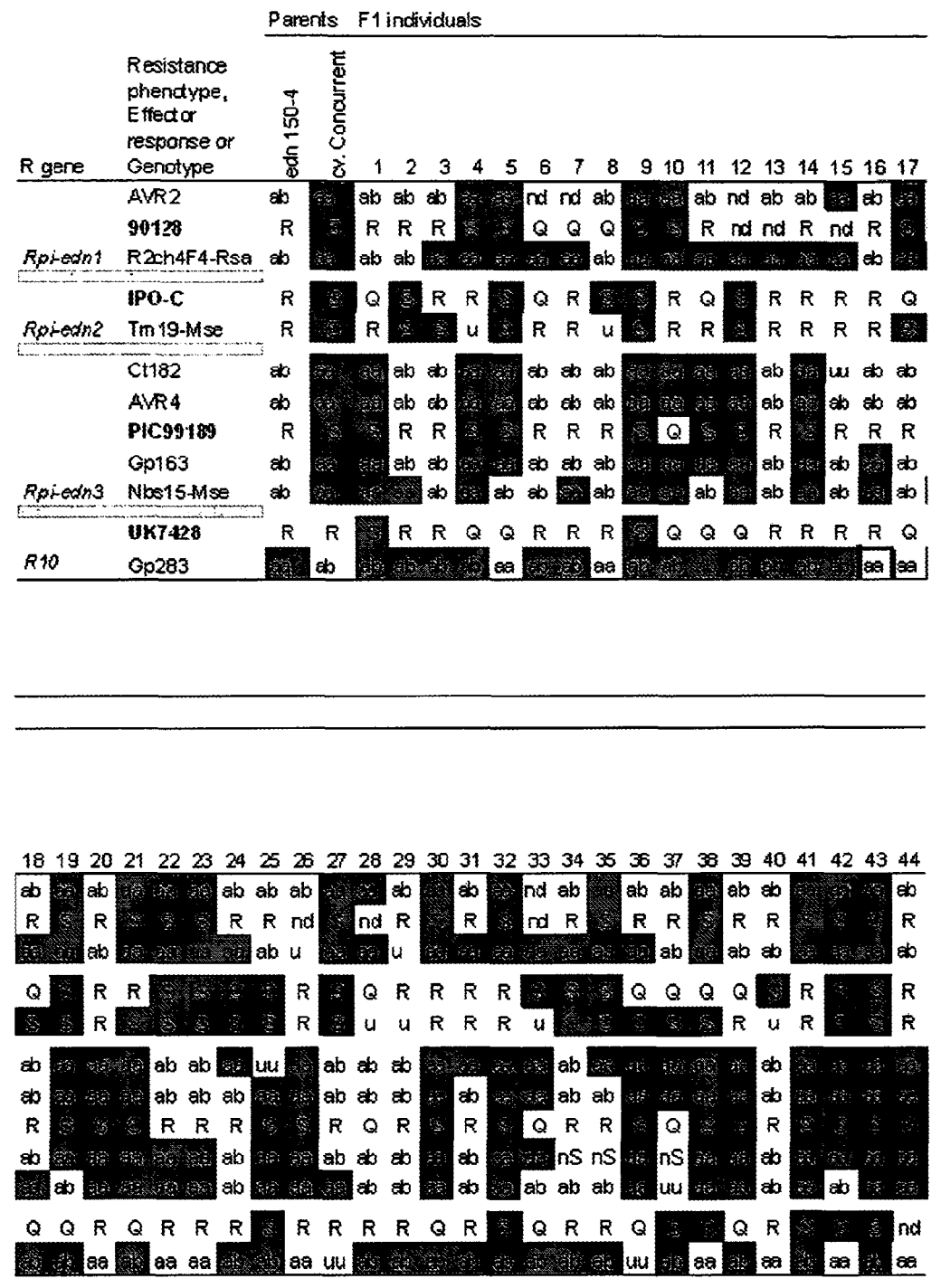

FIG. 2. Graphical genotyping of the edn150-4 x cv. Concurrent population. A subset of the F1 individuals is represented. Indicated are the response to the four Phytophthora infestans isolates (90128, IPO-C, PIC99189 and UK7824), the response to effectors AVR2 and AVR4 linked to the resistance to 90128 and PIC99189, respectively, and the genotype score for one or two markers linked to the individual R gene loci. R: resistant (green), S: susceptible (red), Q: unclear phenotype, ab: presence of fragment, aa: absence of fragment, nd: not determined. The grey horizontal lines separate the R gene loci. The F1 individual number 16 contains the three Rpi-edn genes and potentially R10 from cv. Concurrent.

FIG. 3. Genetic positions of the Rpi-edn2 and Rpi-edn3 genes segregating in edn150-4 x cv. Concurrent population; mapping on chromosome 9 and 11, respectively. The genetic maps are compared to the SH x RH UHD reference genetic map (van Os et al. 2006, Genetics 173:1075-1089) The vertical black bars are representing the known R gene clusters.

FIG. 4. Nucleotide sequence and corresponding amino acid sequence of Rpi-edn2.

FIG. 5. Amino acid sequences alignment of Rpi-edn2 and highly homologous proteins.

Figure 6:
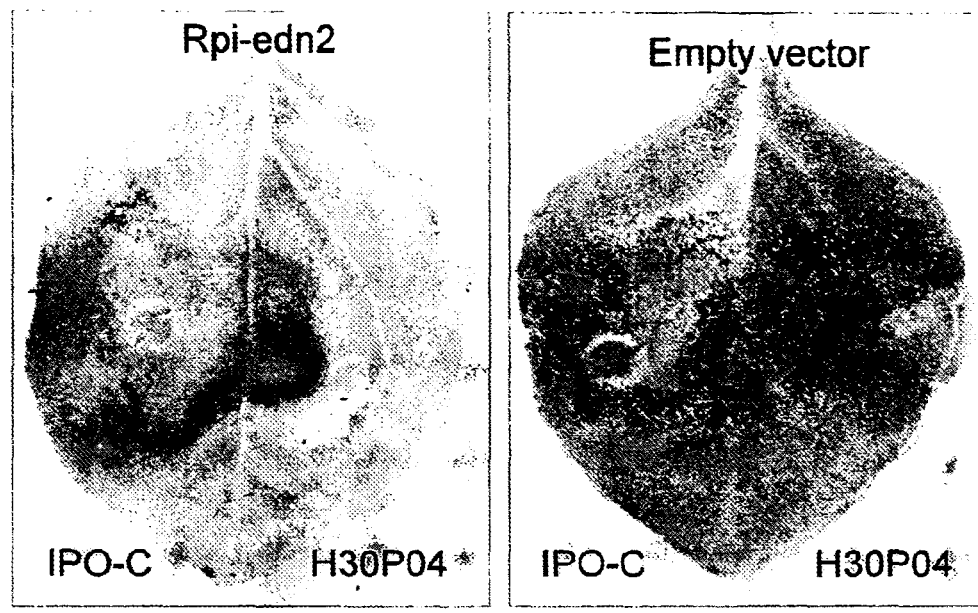

FIG. 6. Transient complementation of Phytophthora susceptibility in Nicotiana benthamiana leaves.

Two days after agro-infiltration with either pDEST32: edn2 or empty binary vector, the leaves were challenged by the inoculation with a zoospore suspension of P. infestans isolate IPO_C (left leaf half) and H30PO4 (right leaf half). Resistance to both isolates co-segregated with the chromosome 9 gene in the F1 population. Typical disease phenotypes developed 6 days after inoculation of control plants that had been agro-infiltrated with binary vector without. Resistance was visible as a HR or XR (eXtreme Resistance) in plants agro-infiltrated with Rpi-edn2.

Figure 7:
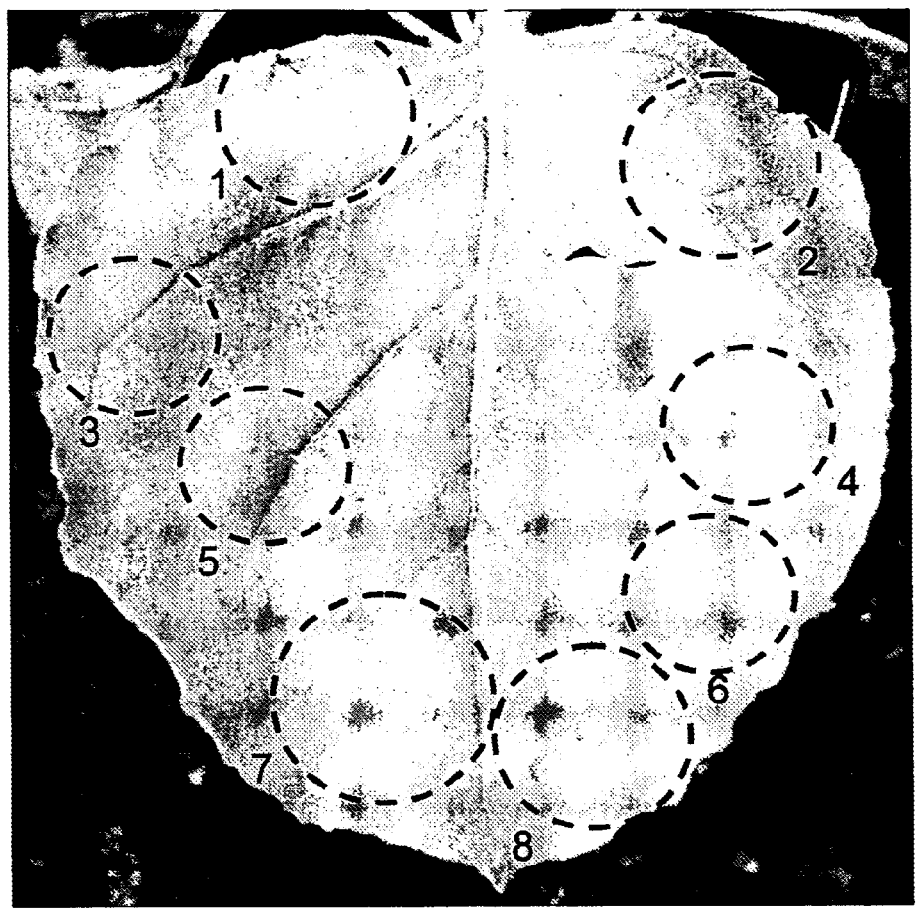

FIG. 7. Recognition of PITG_15039 by Rpi-edn2.

Effector candidates were agroinfiltrated into the right leaf half of N. benthamiana at $OD_{600}$=0.5 (spot2=Avr3a, 4=PITG_09616, 6=PITG_10540, and 8=PITG_15039). In the left leaf half the same effectors are co-infiltrated with R3a (spot1=Avr3a) or with Rpi-edn2 (spots 3=PITG_09616, 5=PITG_10540, and 7=PITG_15039). Pictures were taken six days after agro-infiltration.

FIGS. 8A-8F. Nucleotide sequence of the BAC clone containing the Rpi-edn2 gene. In italics is the mutator transposable element (pos. 195-3310). In highlights is the Rpi-edn2 gene (pos. 5618-8829). The coding sequence locates between position 6140-8731. In bold is a partial Rpi-edn2 homologous gene (pos. 11924-13956). Underlined is a complete Rpi-edn2 homologous gene (pos. 14406-17847). A potential open reading frame is located between positions 15157-17745.

Figure 9:
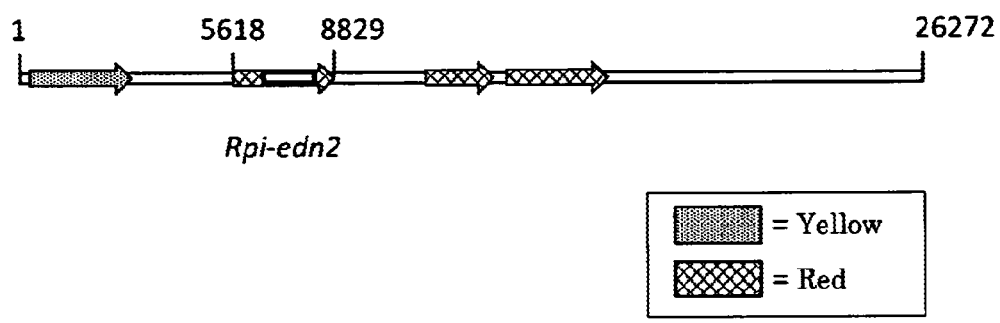

FIG. 9. Annotation of the Rpi-edn2 genomic region.

Genes were predicted using FGENESH algorithm. A yellow arrow shows the presence of a mutator transposable element (gene a). Red arrows show the presence of Rpi-edn2 and Rpi-edn2-like sequences (genes b and c). The box in the first red arrow shows the location of the single exon encoding Rpi-edn2 protein. Positions in the BAC insert as depicted in FIG. 8, relative to the beginning of the insert, are indicated by the numbers.

DETAILED DESCRIPTION

As used herein, the term "plant or part thereof" means any complete or partial plant, single cells and cell tissues such as plant cells that are intact in plants, cell clumps and tissue cultures from which potato plants can be regenerated. Examples of plant parts include, but are not limited to, single cells and tissues from pollen, ovules, leaves, embryos, roots, root tips, anthers, flowers, fruits, stems shoots, tubers, including potato tubers for consumption or 'seed tubers' for cultivation or clonal propagation, and seeds; as well as pollen, ovules, leaves, embryos, roots, root tips, anthers, flowers, fruits, stems, shoots, scions, rootstocks, seeds, protoplasts, calli, and the like.

As used herein, the term "population" means a genetically heterogeneous collection of plants sharing a common genetic derivation.

As used herein, the term "variety" is as defined in the UPOV treaty and refers to any plant grouping within a single botanical taxon of the lowest known rank, which grouping can be: (a) defined by the expression of the characteristics that results from a given genotype or combination of genotypes, (b) distinguished from any other plant grouping by the expression of at least one of the said characteristics, and (c) considered as a unit with regard to its suitability for being propagated unchanged.

The term "cultivar" (for cultivated variety) as used herein is defined as a variety that is not normally found in nature but that has been cultivated by humans, i.e. having a biological status other than a "wild" status, which "wild" status indicates the original non-cultivated, or natural state of a plant or accession. The term "cultivar" specifically relates to a potato plant having a ploidy level that is tetraploid. The term "cultivar" further includes, but is not limited to, semi-natural, semi-wild, weedy, traditional cultivar, landrace, breeding material, research material, breeder's line, synthetic population, hybrid, founder stock/base population, inbred line (parent of hybrid cultivar), segregating population, mutant/genetic stock, and advanced/improved cultivar.

As used herein, "crossing" means the fertilization of female plants (or gametes) by male plants (or gametes). The term "gamete" refers to the haploid or diploid reproductive cell (egg or sperm) produced in plants by meiosis, or by first or second restitution, or double reduction from a gametophyte and involved in sexual reproduction, during which two gametes of opposite sex fuse to form a diploid or polyploid zygote. The term generally includes reference to a pollen (including the sperm cell) and an ovule (including the ovum). "Crossing" therefore generally refers to the fertilization of ovules of one individual with pollen from another individual, whereas "selfing" refers to the fertilization of ovules of an individual with pollen from genetically the same individual.

The term "backcrossing" as used herein means the process wherein the plant resulting from a cross between two parental lines is crossed with one of its parental lines, wherein the parental line used in the backcross is referred to as the recurrent parent. Repeated backcrossing results in the genome becoming more and more similar to the recurrent parent, as far as this can be achieved given the level of homo- or heterozygosity of said parent.

As used herein, "selfing" is defined as refers to the process of self-fertilization wherein an individual is pollinated or fertilized with its own pollen.

The term "marker" as used herein means any indicator that is used in methods for inferring differences in characteristics of genomic sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location.

As used herein, "locus" is defined as the genetic or physical position that a given gene occupies on a chromosome of a plant.

The term "allele(s)" as used herein means any of one or more alternative forms of a gene, all of which alleles relate to the presence or absence of a particular phenotypic trait or characteristic in a plant. In a diploid cell or organism, the two alleles of a given gene occupy corresponding loci on a pair of homologous chromosomes. It is in some instance more accurate to refer to "haplotypes" (i.e. an allele of a chromosomal segment) in stead of "allele", however, in these instances, the term "allele" should be understood to comprise the term "haplotype".

The term "heterozygous" as used herein, and confined to diploids, means a genetic condition existing when different alleles reside at corresponding loci on homologous chromosomes.

As used herein, and confined to diploids, "homozygous" is defined as a genetic condition existing when identical alleles reside at corresponding loci on homologous chromosomes.

As used herein, and confined to tetraploids, the term "nulliplex", "simplex", "duplex", "triplex" and "quadruplex", is defined as a genetic condition existing when a specific allele at a corresponding locus on corresponding homologous chromosomes is present 0, 1, 2, 3 or 4 times, respectively. At the tetraploid level the phenotypic effect associated with a recessive allele is only observed when the allele is present in quadruplex condition, whereas the phenotypic effect associated with a dominant allele is already observed when the allele is present in a simplex or higher condition.

The terms "haploid", "diploid", "tetraploid" and "pentaploid" as used herein are defined as having respectively one, two, four and five pairs of each chromosome in each cell (excluding reproductive cells).

The term "haplotype" as used herein means a combination of alleles at multiple loci that are transmitted together on the same chromosome. This includes haplotypes referring to as few as two loci, and haplotypes referring to an entire chromosome depending on the number of recombination events that have occurred between a given set of loci.

As used herein, the term "infer" or "inferring", when used in reference to assessing the presence of the fungal resistance as related to the expression of the Rpi-edn2 gene, means drawing a conclusion about the presence of said gene in a plant or part thereof using a process of analyzing individually or in combination nucleotide occurrence(s) of said gene in a nucleic acid sample of the plant or part thereof. As disclosed herein, the nucleotide occurrence(s) can be identified directly by examining the qualitative differences or quantitative differences in expression levels of nucleic acid molecules, or indirectly by examining (the expression level of the Rpi-edn2 protein.

The term "primer" as used herein refers to an oligonucleotide which is capable of annealing to the amplification target allowing a DNA polymerase to attach thereby serving as a point of initiation of DNA synthesis when placed under conditions in which synthesis of primer extension product which is complementary to a nucleic acid strand is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and source of primer. A "pair of bi-directional primers" or "primer pair" as used herein refers to one forward and one reverse primer as commonly used in the art of DNA amplification such as in PCR amplification.

As used herein, the term "probe" means a single-stranded oligonucleotide sequence that will recognize and form a hydrogen-bonded duplex with a complementary sequence in a target nucleic acid sequence analyte or its cDNA derivative.

The terms "stringency" or "stringent hybridization conditions" refer to hybridization conditions that affect the stability of hybrids, e.g., temperature, salt concentration, pH, formamide concentration and the like. These conditions are empirically optimised to maximize specific binding and minimize non-specific binding of primer or probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridises to a perfectly matched probe or primer.

Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1 M NaCl, 1% SDS at 37° C., and a wash in 0.1×SSC at 60° C. Hybridization procedures are well known in the art and are described in e.g. Ausubel, F. M., Brent, R., Kingston, R. E., Moore, D. D., Seidman, J. G., Smith, J. A., Struhl, K. eds. (1998) Current protocols in molecular biology. V. B. Chanda, series ed. New York: John Wiley & Sons.

The present invention describes the cloning of the Rpi-edn2 gene. Rpi-edn2 was mapped to an R gene cluster on chromosome 9 of S. x edinense. The gene contains three domains that are common to other resistance genes, the CC, NBS and LRR domain.

To date, five principal classes of R-genes have been identified, based upon conserved protein domains (for review see Martin G B, Bogdanove A J, Sessa G, Annu Rev Plant Biol 2003, 54:23-61). The most abundant class are the cytoplasmic nucleotide-binding site-leucine-rich repeat (NBS-LRR) proteins (Rommens C M, Kishore G M, Curr Opin Biotechnol 2000, 11:120-125). The other classes comprise proteins with extracytoplasmic LRRs (eLRRs) anchored to a transmembrane (TM) domain (receptor-like proteins [RLPs]), cytoplasmic serine-threonine (Ser/Thr) receptor-like kinases (RLKs) with extracellular LRRs (such as disclosed in WO 2004/007712), cytoplasmic Ser/Thr kinases without LRRs, and proteins with a membrane anchor fused to a coiled coil (CC) domain. The common NBS-LRR-encoding proteins currently include over 20 functionally proven R-genes from diverse plant species (Van Der Biezen E A, Freddie C T, Kahn K, Parker J E, Jones J D, Plant J 2002, 29:439-451). Studies have focused on this family because its only known function to date is in disease resistance (Meyers B C, Kaushik S, Nandety R S, Curr Opin Plant Biol 2005, 8:129-134). Gene products are composed of a conserved central NBS and variable length C-terminal LRR domain of 10 to 40 short LRR motifs (Cannon S B, Zhu H, Baumgarten A M, Spangler R, May G, Cook D R, Young N D, J Mol Evol 2002, 54:548-562). The NBS domain is important for ATP binding and hydrolysis and is believed to be involved in signal transduction, triggered by the presence of the pathogen (van Der Biezen E A, Jones, Curr Biol 1998, 8:R226-R227; Tameling W I, Elzing a S D, Darmin P S, Vossen J H, Takken F L, Haring M A, Cornelissen B J, Plant Cell 2002, 14:2929-2939). The LRR domain is likely to be involved in protein-protein interactions, recognizing pathogen elicitor molecules (Young N D, Curr Opin Plant Biol 2000, 3:285-290. A high mutation rate in the LRR contributes to genetic variability, necessary for specific recognition of diverse pathogens (Michelmore R W, Meyers B C, Genome Res 1998, 8:1113-1. Two subfamilies exist in NBS-LRR R proteins based upon N-terminal motifs. The TIR NBS subfamily R proteins display homology between the N-terminal amino acid motif and the receptor domain in *Drosophila* Toll and basal mammalian Interleukin (IL) 1 immunity factors in animals (Parker J E, Coleman M J, Szabo V, Frost L N, Schmidt R, van Der Biezen E A, Moores T, Dean C, Daniels M J, Jones J D, Plant Cell 1997, 9:879-894. Non-TIR NBS subfamily R proteins can contain an N-terminal coiled-coil (CC) motif, a subset of which code for a leucine zipper sequence (LZ). TIR subfamily NBS-LRR proteins appear to be restricted to dicotyledons.

A coiled-coil (CC) domain is located in the N-terminal parts of the Rpi-edn2 protein between amino acids 1 and 153 (amino acid sequence depicted in FIG. 4). In the first 153 residues 3 pairs of putative heptad motifs composed of hydrophobic residues could be recognized in Rpi-edn2. A NB-ARC (nucleotide-binding site, apoptosis, R gene products, CED-4) domain could be recognized in the amino acid stretch between residues 153 and 444 (Ploop, Kinase-2, GLPL) (Van der Biezen and Jones 1998). The C terminal half of Rpi-edn2 comprises a series of 15 LRR motifs of irregular size that can be aligned according to the consensus sequence LxxLxxLxxLxLxxC/N/Sx(x)LxxLPxx (where x is any amino acid, and L is selected from the group of Leucine, Isoleucine or Valine (L, I or V) (SEQ ID NO:6 and SEQ ID NO:7) (McHale et al. 2006).

At the protein level, Rpi-edn2 shares 80% amino acid identity with Rpi-mcq1.1, 77% with Rpi-mcq1.2. Lower percentage homology was found with Rpi-vnt1 (73%) and Tm-2$^2$, a tomato resistance gene against Tomato Mosaic virus, sharing 73% and 72% identity, respectively.

In a first embodiment, the invention provides an isolated or recombinant nucleic acid sequence comprising a nucleic acid sequence encoding the amino acid sequence Rpi-edn2 as presented in FIG. 4 or a functional fragment or a functional homologue thereof, i.e. a functional fragment or a functional homologue of the amino sequence as shown in FIG. 4.

The term "nucleic acid" means a single or double stranded DNA or RNA molecule.

Also included are the complementary sequences of the herein described nucleotide sequences.

The term "functional fragment thereof" is typically used to refer to a fragment of the Rpi-edn2 protein or the nucleic acid sequence encoding therefore, that is capable of providing at least partial resistance or increasing resistance in a plant of the Solanaceae family against an oomycete infection, more specifically against *P. infestans*, more specifically against isolate IPO-C. Such a fragment is, for example, a truncated version of the Rpi-edn2 protein. A truncated version/fragment of the Rpi-edn2 protein is a fragment that is smaller than 863 amino acids and preferably comprises (part of) the NB-ARC and the LRR domains and/or the N-terminal CC domain of the Rpi-edn2 protein.

The term "functional homologue" is typically used to refer to a protein sequence or the nucleic acid sequence encoding for such a protein that is highly homologous to or has a high identity with the herein described Rpi-edn2 protein or nucleic acids, which (encoded) protein is capable of providing at least partial resistance or increasing resistance in a plant of the Solanaceae family against an oomycete infection, more specifically against *P. infestans*, more specifically against isolate IPO-C. Included are artificial changes or amino acid residue substitutions that at least partly maintain the effect of the Rpi-edn2 protein. For example, certain amino acid residues can conventionally be replaced by others of comparable nature, e.g. a basic residue by another basic residue, an acidic residue by another acidic residue, a hydrophobic residue by another hydrophobic residue, and so on. Examples of hydrophobic amino acids are valine, leucine and isoleucine. Phenylalanine, tyrosine and tryptophan are examples of amino acids with an aromatic side chain and cysteine as well as methionine are examples of amino acids with sulphur-containing side chains. Serine and threonine contain aliphatic hydroxyl groups and are considered to be hydrophilic. Aspartic acid and glutamic acid are examples of amino acids with an acidic side chain. In short, the term "functional homologue thereof" includes variants of the Rpi-edn2 protein in which amino acids have been inserted, replaced or deleted and which at least partly maintain the effect of the Rpi-edn2 protein (i.e. at least partly providing or increasing resistance in a plant of the Solanaceae family against an oomycete infection, more specifically against *P. infestans*, more specifically against isolate IPO-C). Preferred variants are variants which only contain conventional amino acid replacements as described above. Also included in the term "functional homologue thereof" are homologous sequences. Preferably, such a homologue has more than 80% identity on the amino acid level. More preferably, the amino acid has an identity of at least 85 or 90%. Even more preferred are amino acids that have an identity of 91, 92, 93, 94 or 95%. Most preferred are amino acids that have an identity of 96, 97, 98 or 99% with the amino acid sequence of Rpi-edn2. Homologous proteins according to the invention have a higher degree of identity with the Rpi-edn2 sequence as the sequences aligned with those proteins in FIG. 5.

A functional homologous nucleic acid sequence is a nucleic acid sequence that encodes a functional homologous protein as described above.

Homology and/or identity percentages can for example be determined by using computer programs such as BLAST, ClustalW or ClustalX.

Many nucleic acid sequences code for a protein that is 100% identical to the Rpi-edn2 protein as presented in FIG. 4. This is because nucleotides in a nucleotide triplet may vary without changing the corresponding amino acid (wobble in the nucleotide triplets). Thus, without having an effect on the amino acid sequence of a protein the nucleotide sequence coding for this protein can be varied. However, in a preferred embodiment, the invention provides an isolated or recombinant nucleic acid sequence as depicted in FIG. 4. In a preferred embodiment, the invention provides an isolated, synthetic, or recombinant nucleic acid that represents the coding sequence (CDS) of the Rpi-edn2 protein, i.e. nucleotides 1-2589 of FIG. 4 or a functional fragment or a functional homologue thereof.

Fragments as well as homologues of the herein described Rpi-edn2 gene and protein can for example be tested for their functionality by using an *Agrobacterium tumefaciens* transient transformation assays (agro-infiltration) and/or by using a detached leaf assay.

Agro-infiltration forms a functional screen for testing candidate genes, whereby 4 week old wild type *Nicotiana benthamiana* plants are infiltrated with *Agrobacterium* strains containing the candidate Rpi-edn2 homologues or nucleotide sequences coding therefore. The infiltrated leaves are subsequently challenged one or several (maximum 3) days after infiltration with a *P. infestans* strain that is virulent on *N. benthamiana*, for example IPO-C or 90128, in detached leaf assays. This system is equally suitable for testing candidate homologous fragments of Rpi-edn2.

Transient gene expression, as is achieved through agro-infiltration, is a fast, flexible and reproducible approach to high-level expression of useful proteins. In plants, recombinant strains of *Agrobacterium tumefaciens* can be used for transient expression of genes that have been inserted into the T-DNA region of the bacterial Ti plasmid. A bacterial culture is infiltrated into leaves, and upon T-DNA transfer, there is ectopic expression of the gene of interest in the plant cells. However, the utility of the system is limited because the ectopic RNA expression ceases after 2-3 days. It is shown that post-transcriptional gene silencing (PTGS) is a major cause for this lack of efficiency. A system based on co-expression of a viral-encoded suppressor of gene silencing, the p19 protein of tomato bushy stunt virus (TBSV), prevents the onset of PTGS in the infiltrated tissues and allows high level of transient expression. Expression of a range of proteins was enhanced 50-fold or more in the presence of p19 so that protein purification could be achieved from as little as 100 mg of infiltrated leaf material. Although it is clear that the use of p19 has advantages, an agro-infiltration without p19 can also be used to test the functionality of candidate fragments and functional homologues.

Alternatively, each candidate gene (for example being a fragment or homologue) construct is targeted for transformation to a susceptible potato cultivar, for example Desiree. Primary transformants are challenged in detached leaf assays using for example isolates H30P04, IPO-C, CA65, USA618 or 90128. Transformants that are resistant to these isolates, especially against IPO-C, harbour for example functional fragments or homologues of Rpi-edn2.

In yet another embodiment, the invention provides a vector comprising a nucleic acid as provided herein, i.e. a nucleic acid capable of providing at least partial resistance or increasing resistance in a plant of the Solanaceae family against an oomycete infection. More particularly, the invention provides a vector comprising an isolated, synthetic or recombinant nucleic acid sequence comprising a nucleic acid sequence encoding the amino acid sequence Rpi-edn2 of FIG. 4 or a functional fragment or a functional homologue thereof. The invention also provides a vector comprising such a nucleic acid sequence. Alternatively, such a vector comprises both nucleotide sequences encoding the Rpi-edn2 protein.

Examples of a suitable vector are pBeloBACII, pBINplus, pKGW-MG or any commercially available cloning vector.

As will be outlined below there are multiple ways in which a nucleic acid of the invention can be transferred to a plant. One suitable means of transfer is mediated by *Agrobacterium* in which the nucleic acid to be transferred is part of a binary vector and hence it is preferred that the above described vector is a binary vector. Another suitable means is by crossing a plant which contains the gene encoding Rpi-edn2 to a plant that does not contain the gene and to identify those progeny of the cross that have inherited the Rpi-edn2 gene.

The invention further provides a host cell comprising a nucleic acid as described herein or a vector as described herein. Examples of a preferred host cell are an *E. coli* cell suitable for BAC clones (e.g. DH10B) or an *Agrobacterium* (host) cell. In another embodiment, said host cell comprises a plant cell. A preferred plant cell is a cell derived from a member of the Solanaceae family and even more preferred said plant cell comprises a cell from *Solanum tuberosum, Solanum lycopersicum*, formerly known as *Lycopersicon esculentum*, pepper and eggplant. From such a cell, a transgenic or genetically modified plant (for example a potato or tomato plant) can be obtained by methods known by the skilled person (for example regeneration protocols).

The invention further provides a leaf, tuber, fruit or seed or part or progeny of a genetically modified plant as described herein.

In yet another embodiment, the invention provides a protein encoded by the herein described isolated or recombinant nucleic acid or a functional fragment or a functional homologue thereof. In a preferred embodiment, the invention provides a protein encoded by a nucleic acid sequence as depicted in FIG. 4. In yet another preferred embodiment, the invention provides a protein comprising the amino acid sequence of FIG. 4 or a functional fragment or a functional homologue thereof.

The herein described Rpi-edn2 protein comprises 863 amino acids. Rpi-edn2 shares the highest homology with Rpi-mcq1.1 (80%) and Rpi-mcq1.2 (77%), R genes from *S. mochiquense*. However, as is shown in Table 6, the Rpi-edn2 protein of the present invention differs from these highly homologous proteins by the fact that it provides resistance towards a different spectrum of *Phytophthora* isolates. Rpi-edn2, like Rpi-vnt1, Tm-$2^2$ and Rpi-mcq1.1, is a member of the large family of CC-NBS-LRR resistance genes. The reference genes Tm-$2^2$, Rpi-vnt1 and Rpi-mcq1.1 can be said to be grouped in a so-called Tm-$2^2$ family subgroup, of which Rpi-edn2 forms a member. However, on basis of the sequence homology, Rpi-edn2 can be considered to form a new subclass within this Tm-$2^2$ family.

As already described, a functional fragment or a functional homologue thereof of Rpi-edn2 is a fragment or homologue that is capable of providing at least partial resistance or increasing resistance in a plant of the Solanaceae family against an oomycete infection.

Means to test the functionality of a functional fragment or a functional homologue of Rpi-edn2 have been provided above.

Based on the herein described nucleic acid sequences, the invention also provides probes and primers (i.e. oligonucleotide sequences complementary to the (complementary) DNA strand as described in FIG. 4). Probes are for example useful in Southern or northern analysis and primers are for example useful in PCR analysis. Primers based on the herein described nucleic acid sequence are very useful to assist plant breeders active in the field of classical breeding and/or breeding by genetic modification of the nucleic acid content of a plant (preferably said plant is a *Solanum tuberosum, Solanum lycopersicum*, formerly known as *Lycopersicon esculentum*), pepper or eggplant in selecting a plant that is capable of expressing for example Rpi-edn2.

Hence, in a further embodiment, the invention provides a binding molecule capable of binding to a nucleic acid as described herein or its complementary nucleic acid. In a preferred embodiment, said binding molecule is a primer or a probe. As mentioned, such a binding molecule is very useful for plant breeders and hence the invention further provides a method for selecting a plant or plant material or progeny thereof for its susceptibility or resistance to an oomycete infection. Preferably, the nucleic acid of a plant to be tested is isolated from said plant and the obtained isolated nucleic acid is brought in contact with one or multiple (preferably different) binding molecule(s). One can for example use a PCR analysis to test plants for the presence of absence of Rpi-edn2 in the plant genome. Such a method would be especially preferable in marker-free transformation protocols, such as described in WO 03/010319.

The herein described Rpi-edn2 protein can also be used to elicit antibodies by means known to the skilled person. The invention thus also provides an antibody that (specifically) binds to the protein(s) encoded by the herein described isolated or recombinant nucleic acid (for example the nucleic acid sequence of FIG. 4 or an antibody that (specifically) binds to a protein as depicted in FIG. 4 or a functional fragment or a functional homologue thereof. Such an antibody is for example useful in protein analysis methods such as Western blotting or ELISA, and hence can be used in selecting plants that successfully express the Rpi-edn2 gene.

Based on the herein provided nucleic acid sequence, the invention also provides the means to introduce or increase resistance against an oomycete infection in a plant. The invention therefore also provides a method for providing at least partial resistance or increasing resistance in a plant against an oomycete infection comprising providing a plant or a part thereof with:
  an isolated or recombinant nucleic acid sequence comprising a nucleic acid sequence encoding the Rpi-edn2 amino acid sequence of FIG. 4 or a functional fragment or a functional homologue thereof, or
  a vector comprising the herein described nucleic acid sequences, or
  a host cell as described herein.

Such a method for providing at least partial resistance or increasing resistance in a plant against an oomycete infection may be based on classical breeding, departing from a parent plant that already contains the Rpi-edn2 gene, or it involves the transfer of DNA into a plant, i.e., involves a method for transforming a plant cell comprising providing said plant cell with one or more nucleic acid sequences as described herein or a vector as described herein or a host cell as described herein.

There are multiple ways in which a recombinant nucleic acid can be transferred to a plant cell, for example *Agrobacterium* mediated transformation. However, besides by *Agrobacterium* infection, there are other means to effectively deliver DNA to recipient plant cells when one wishes to practice the invention. Suitable methods for delivering DNA to plant cells are believed to include virtually any method by which DNA can be introduced into a cell, such as by direct delivery of DNA such as by PEG-mediated transformation of protoplasts, by desiccation/inhibition-mediated DNA uptake (Potrykus et al., Mol. Gen. Genet., 199:183-188, 1985), by electroporation (U.S. Pat. No. 5,384,253), by agitation with silicon carbide fibers (Kaeppler et al., 1990; U.S. Pat. No. 5,302,523; and U.S. Pat. No. 5,464,765), and by acceleration of DNA coated particles (U.S. Pat. No. 5,550,318; U.S. Pat. No. 5,538,877; and U.S. Pat. No. 5,538,880). Through the application of techniques such as these, cells from virtually any plant species may be stably transformed, and these cells may be developed into transgenic plants.

In case *Agrobacterium* mediated transfer is used, it is preferred to use a substantially virulent *Agrobacterium* such as *A. tumefaciens*, as exemplified by strain A281 or a strain derived thereof or another virulent strain available in the art. These *Agrobacterium* strains carry a DNA region originating from the virulence region of the Ti plasmid pTiBo542, which coordinates the processing of the T-DNA and its transfer into plant cells. *Agrobacterium*-based plant transformation is well known in the art (as e.g. described in, for example by Komari, T. et al.: Plant Transformation Technology: *Agrobacterium*-Mediated Transformation, in: Handbook of Plant Biotechnology, Eds. Christou, P. and Klee, H., John Wiley & Sons, Ltd, Chichester, UK 2004, pp. 233-262). Preferably a marker-free transformation protocol is used, such as described in WO 03/010319.

In a preferred embodiment, the target plant is transformed with additional resistance genes, a phenomenon known under the name of "gene stacking". As is explained and shown in the experimental part, the presence of multiple resistance genes can enhance the resistance of a plant against infection because firstly the genes can complement each other with respect to resistance to various isolates or pathotypes of the infectious agent, and secondly, triggering more than one resistance mechanism (that by itself would not lead to a full resistance) can lead to a substantial increase of the resistance reactions in the host plant, which could well be sufficient to reach full resistance.

Alternatively, the nucleic acid of the Rpi-edn2 gene, and optionally other resistance genes, like Rpi-mcq1.1, Rpi-mcq1.2, Rpi-vnt1, Rpi-chc1, Rpi-avl1.1, Rpi-avl1.2, Rpi-blb1, Rpi-blb2, Rpi-blb3, and many others, may be introduced into a plant by crossing. Such a crossing scheme starts off with the selection of a suitable parent plant. This may for instance be an original *Solanum* x edinense genotype (such as accession GLKS 25492, GLKS 25493 and GLKS 25494), or a plant that has obtained the desired nucleic acid by genetic engineering as described above.

Any suitable method known in the art for crossing selected plants may be applied in the method according to the invention. This includes both in vivo and in vitro methods. A person skilled in the art will appreciate that in vitro techniques such as protoplast fusion or embryo rescue may be applied when deemed suitable.

Selected plants that are used for crossing purposes in the methods according to the invention may have any type of ploidy. For example, selected plants may be haploid, diploid, triploid, tetraploid or pentaploid.

Methods for crossing a polyploid plant with a tetraploid plant are well known in the art and can be readily applied by a person skilled in the art. For example, S. x edinense has been used for a long time in breeding programs especially for its good field resistance to *P. infestans* (van Soest, 1984). Crosses of the pentaploid S. x edinense with a tetraploid variety (e.g. Concurrent) yield tetraploid progeny. For potatoes a resistant tetraploid plant is preferred, since tetraploid plants are known to have higher yields of tubers.

Since the resistance characteristic has appeared to be a dominant trait, it is sufficient if only one allele with the functional gene is present.

Preferably, selected plants are crossed with each other using classical in vivo crossing methods that comprise one or more crossing steps including selfing. By applying such classical crossing steps characteristics of both the parents can be combined in the progeny. For example, a plant that provides a high yield can be crossed with a plant that contains large amounts of a certain nutrient. Such a crossing would provide progeny comprising both characteristics, i.e. plants that not only comprise large amounts of the nutrient but also provide high yields.

When applying backcrossing, F1 progeny is crossed with one of its high-yielding parents P to ensure that the characteristics of the F2 progeny resemble those of the high-yielding parent. For example, a selected diploid potato with oomycete resistance is made tetraploid by using colchicine and then crossed with a selected high-yielding tetraploid potato cultivar, with the purpose of ultimately providing a high-yielding tetraploid progeny having oomycete resistance. Also selfing may be applied. Selected plants, either parent or progeny, are then crossed with themselves to produce inbred varieties for breeding. For example, selected specimens from the above mentioned F1 progeny are crossed with themselves to provide an F2 progeny from which specimens can be selected that have an increased level of resistance.

After transfer of a nucleic acid into a plant or plant cell, it must be determined which plants or plant cells have been provided with said nucleic acid. When selecting and crossing a parental genotype in a method according to the invention, a marker is used to assist selection in at least one selection step. It is known in the art that markers, indicative for a certain trait or condition, can be found in vivo and in vitro at different biological levels. For example, markers can be found at peptide level or at gene level. At gene level, a marker can be detected at RNA level or DNA level. Preferably, in the present invention the presence of such a marker is detected at DNA level. Alternatively, proper expression of the Rpi-edn2 protein can be assessed in plant parts by transforming an immunoassay with an antibody that specifically binds the protein. Next to the primers and probes according to the invention, use can also be made of specific markers that are to be found in the vicinity of the coding sequence. Such markers are indicated in the experimental part below and comprise the Tm2-like profiling markers as indicated in Table. 7. Highly preferred markers are Tm1900, Tm19F-Mse, Stm021, mcq-ATG1, mcq-c2-stop, EDN-F and EDN-R and primers that were used for the Tm2-like profiling as described in the experimental part and Table 5.

Even more highly preferred markers are derived from the nucleotide sequence presented in FIG. 4. It is submitted that parts of this sequence are unique for the gene and thus can serve as a very specific marker.

In case of transgenic approaches selecting a transformed plant may be accomplished by using a selectable marker or a reporter gene. Among the selective markers or selection genes that are most widely used in plant transformation are the bacterial neomycin phosphotransferase genes (nptI, nptII and nptIII genes) conferring resistance to the selective agent kanamycin, suggested in EP131623 and the bacterial aphIV gene suggested in EP186425 conferring resistance to hygromycin. EP 275957 discloses the use of an acetyl transferase gene from *Streptomyces viridochromogenes* that confers resistance to the herbicide phosphinotricin. Plant genes conferring relative resistance to the herbicide glyphosate are suggested in EP218571. Suitable examples of reporter genes are beta-glucuronidase (GUS), beta-galactosidase, luciferase and green fluorescent protein (GFP). However, preferably a marker-free approach, such as disclosed in WO 03/010319, is used, where the presence of the resistance gene(s) can be assayed with nucleotide sequence based assays.

In a preferred embodiment, the invention provides a method for providing at least partial resistance or increasing resistance in a plant against an oomycete infection comprising providing a plant or a part thereof with:
an isolated or recombinant nucleic acid sequence comprising a nucleic acid sequence encoding the Rpi-edn2 amino acid sequence (see FIG. 4) or a functional fragment or a functional homologue thereof, or
a vector comprising the herein described nucleic acid sequence, or
a host cell as described herein,
wherein said oomycete comprises *Phytophthora*, preferably *Phytophthora infestans* and/or wherein said plant comprises a plant from the Solanaceae family, preferably a potato or tomato plant, more preferably a tetraploid potato plant.

The invention also provides a plant that is obtainable by using a method for providing at least partial resistance or increasing resistance in a plant against an oomycete infection as described above. A preferred plant is a plant from the Solanaceae family and even more preferred said plant is a *Solanum tuberosum* or a *Solanum lycopersicum*, formerly known as *Lycopersicon esculentum, Solanum melononga, Capsicum* spp., such as *C. annuum, C. baccatum, C. chinense, C. frutescens* and *C. pubescens*. The invention thus also provides a plant that has been provided with a nucleic acid encoding a Rpi-edn2 protein or a functional fragment or a functional homologue thereof.

The invention further provides a transgenic plant part or progeny of a plant according to the invention comprising a nucleic acid encoding the Rpi-edn2 amino acid sequence(s) of FIG. 4 or a functional fragment or a functional homologue thereof.

In a preferred embodiment, the herein described nucleic acid is transferred to a *Solanum* variety other than *Solanum edinense*, i.e. the herein described nucleic acid is preferably provided to a non-edinense background, preferably *S. lycopersicon* or *S. tuberosum*. Of the latter most preferred is a tetraploid variety and more preferably to a commercial interesting variety such as Bintje, Desiree or Premiere, Spunta, Nicola, Favorit, Russet Burbank, Aveka or Lady Rosetta.

It is also possible to provide the resistance according to the invention to a plant that is already partially resistant to an oomycete infection, wherein said plant is provided with a nucleic acid encoding a further resistance gene, such as Rpi-blb1, -2, -3, Rpi-vnt1, Rpi-chc1, Rpi-avl1-1, Rpi-avl1-2, Rpi-R1, Rpi-R2, Rpi-R3a, Rpi-R3b, Rpi-mcd1 or Rpi-mcq1.

The invention further provides use of an isolated or recombinant nucleic acid sequence comprising a nucleic acid sequence encoding the Rpi-edn2 amino acid sequences of FIG. 4 or a functional fragment or a functional homologue thereof or use of a vector comprising any of said nucleic acid sequences or use of a host cell comprising any of said nucleic acid sequences or said vector for providing a plant with at least partial resistance against an oomycete infection. In a preferred embodiment, said oomycete comprises *Phytophthora* and even more preferably *Phytophthora infestans*. In yet another preferred embodiment said plant comprises *Solanum tuberosum* or *Solanum lycopersicum*, formerly known as *Lycopersicon esculentum*.

In yet another embodiment, the invention provides a method for producing an Rpi-edn2 protein or a functional fragment or a functional homologue thereof comprising functionally linking a nucleic acid as described herein to a regulatory sequence and allowing said nucleic acid to be expressed in a host cell. Examples of a regulatory sequence are a promoter and/or terminator sequence.

Further, the plants that harbour the resistance molecules of the present invention also show a specific pathogen profile, in the sense that said plants will show a hypersensitive reaction (ending in necrosis of the infected tissue) with a number of elicitor or effector molecules derived from different isolates of *Phytophthora infestans*. As can be seen in Table 9, several elicitors evoke this response in the av1478-2 plant (for more details see the experimental part), such as PITG_20336, PITG_14039, PITG_20301, PITG_20303, PITG_20300, PITG_22880, PITG_09616, PITG_10540, PITG_15039, PITG_04097, PITG_04169, PITG_16726, PITG_23131 and PITG_07550_9, while other elicitors, such as Avr3a, Avr-vnt1, Avr-blb1, PITG_00774 and PITG_10465, only show no or a minimal response. Thus, also parts of the invention are those nucleic acids that, when transformed and expressed in plants, show a responsiveness to pathogen effectors that resemble the profile as depicted in Table 7, more specifically that show a reaction to PITG_20336, PITG_14039, PITG_20301, PITG_20303, PITG_20300, PITG_22880, PITG_09616, PITG_10540, PITG_15039, PITG_04097, PITG_04169, PITG_16726, PITG_23131 and PITG_07550_9, which shows in the occurrence of a HR in more than 50% of the cases.

The invention will be explained in more detail in the following, non-limiting example.

EXPERIMENTAL PART

In the present study, we intended to identify the mapping position of the R gene responsible for the high level of resistance to *P. infestans* in S. x edinense, for further map based cloning. Two segregating populations were produced from different S. x edinense genotypes (edn151-1 and edn150-4) crossed with cv. Concurrent. They were tested with different isolates and effectors that could discriminate between the different R genes (Champouret 2010; Oh et al. 2009; Vleeshouwers et al. 2008). SSR markers, NBS profiling (van der Linden et al. 2004) and CAPS markers were used to link the segregation of the resistance to a chromosomal position. Gene family directed profiling (GDFP) was developed for different R genes and successfully applied to obtain markers that are closely linked to those R genes.

Materials and Methods

Plant Material and Mapping Population

S. x edinense P. Berthault accessions were provided by the Potato Collection Gross Lüsewitz, Germany (GLKS). The accessions were collected from an area near Toluca de Lerdo in Mexico (SolRgene database, www.plantbreeding.wur.nl/phytophthora/). Fifteen genotypes from three S. x edinense accessions (GLKS 25492, GLKS 25493 and GLSK 25494) were screened for resistance to *P. infestans*. Two resistant genotypes were selected and crossed with the susceptible cv. Concurrent to generate F1 mapping populations. The recombinant F1 genotypes of interest were transferred to in vitro culture to be maintained and multiplied. Resistant individual Edn150-4-104 was crossed with cv Aveka (FIG. 1). Resistant clone RH4x-149-006 was crossed with KA2002-5030 to generate segregating population KA2006-515. One hundred individuals were tested in the field for resistance to *P. infestans* IPO-C. Resistance segregated 1:1 in the resulting progeny indicating the presence of one major Rpi gene in the resistant parent.

*Phytophthora* Isolates and Disease Tests

*Phytophthora* isolates and their race specificities and origin are shown in Table 1. These isolates are obtainable from by Geert Kessel, Francine Govers (Wageningen University, The Netherlands) and Paul Birch (University of Dundee, Scotland, UK). Plants were tested for resistance by three different disease assays: an in vitro assay (Huang 2005), a detached leaf assay, (Vleeshouwers et al. 1999), and a field experiment. The in vitro assay was performed once on five plantlets with the *P. infestans* isolate 90128. In the detached leaf assay, one leaf between the third and the fifth fully developed leaves was collected from five weeks old plants, and inoculated with the two isolates 90128 and IPO-C. The leaves were scored after six days as resistant (R) due to a hypersensitive response (HR), susceptible (S) if a sporulating lesion appeared or as quantitative (Q) for a response not clearly resistant or susceptible. Two field trials, including S. x edinense genotypes, were performed in the summer of 2005 and 2007, in Wageningen, the Netherlands. Each field trial consisted of two randomized blocks, and within the blocks, genotypes were represented as four-plant subplots which were treated as single experimental unit as described by Colon and Budding (1988). For comparisons between years, standard cultivars Ostara, Bildtstar, Eersteling, Pimpernel, Robijn and Biogold were included. Spreader rows consisted of potato cultivar Bintje, the border rows consisted of potato cultivar Nicola. For the inoculum production, a large number of potato cultivar Bintje leaves were inoculated in detached leaf assay with isolate IPO-C. After 6 days, spores were washed off to prepare a spore suspension in large containers. Zoospore release was induced by incubating the containers at 10° C. At nightfall, the zoospore suspension was sprayed on the potato field using a tractor with two spraying arms. Disease assessments were made at weekly intervals. The percentage of leaf area covered with late blight lesions was estimated for each plot (Colon et al. 1988). From these readings the area under the disease progress curve (AUDPC) was calculated (Fry 1978) and subsequently, the AUDPC values were transformed to a 1 (susceptible)-9 (resistant) scale (SolRgene database).

Marker Development

Young leaf tissue was collected from plants grown in the greenhouse. Genomic DNA was isolated by following the CTAB protocol (Park et al. 2005) with the Retsch machine in a 96 well format. Several marker technologies were used in this study: CAPS markers, SSR markers, NBS profiling markers (van der Linden et al. 2004) and R gene family directed (GFDP) profiling markers that represent particular R gene families.

A set of approximately 80 SSR markers, covering the potato genome (Collins et al. 1999; Feingold et al. 2005; Ghislain et al. 2004), was applied to determine the chromosomal position of the segregating R gene. Parental genomic DNA and 11 resistant and 11 susceptible F1 individuals from the mapping populations were used for the SSR marker screen. PCR reactions for the SSR markers were performed using a single PCR program: an initial cycle at 95° C. for 2 min; then 30 cycles of 95° C. for 30 s sec, 56° C. for 30 sec, using a ramp of 1° C./min, and 72° C. for 45 sec, using a ramp of 1° C./min; and a final step at 72° C. for 3 min Subsequently the PCR products were run on acrylamide gels and visualized using the LI-COR technology (Lincoln, Nebr., USA).

To confirm the mapping position and obtain PCR markers linked to the R genes, known CAPS markers from the SGN database (solgenomics.net/), and the SH x RH genetic map (van Os et al. 2006), located close to the R gene clusters, on the identified chromosome arm were tested.

Gene family directed profiling was used to develop markers closely linked to the R gene. It was performed as NBS profiling previously described (van der Linden et al. 2004) by replacing the NBS primers by gene family specific primers. For three R gene families R2, Tm2 and N, sequences available from NCBI (www.ncbi.nlm.nih.gov/) and sequences from allele mining studies performed in our laboratory were collected and aligned. Primers were designed on conserved sequences for each family on the different domains of the gene: CC or TIR, NBS and LRR (Table 1). Some degenerate primers were designed especially for the N-like profiling. This analysis was combined with a bulk segregant analysis (BSA, Michelmore et al. 1991) on the F1 populations. Eight F1 individuals giving a resistant or susceptible phenotype were pooled and screened with the primer/enzyme combinations. The PCR products were visualized by electrophoresis on acrylamide gels. The fragments identified to be associated with the resistance were cut out of the gel and sequenced.

Effector Screening

A collection of approximately 250 RXLR encoding genes (also referred to as effectors) derived from the P. infestans genome (Haas et al. 2009) were cloned without their signal peptide into the binary vector pMDC32 under the control of a double 35S promoter. All the plasmids were introduced into A. tumefaciens strain AGL1 (Lazo et al. 1991) in combination with the helper plasmid pBBR1MCS-5.virGN54D (Van Der Fits et al. 2000). The agroinfiltrations were carried out on young edn150-4 plants three weeks after transplanting from in vitro multiplication. In total 24 replications per effector clone were made. R3a and Avr3a (Bos et al. 2006) were used as positive control, and empty pMDC32 as negative control. The agroinfiltration experiments of the recombinant A. tumefaciens were performed as described by van der Hoorn et al. (2000) with some adaptations.

Agrobacterium tumefaciens cultures were grown in 3 ml of LB medium supplemented with antibiotics to select for the A. tumefaciens strains (carbenicilin), the binary vector (kanamycin or spectinomycin) and the helper plasmid (chloramphenicol). The next day, the cultures were transferred to 15 ml of YEB medium supplemented with antibiotics to select for the vector and the helper plasmid. On the third day, the cells were harvested and re-suspended in MMA solution supplemented with acetosyringone to a final OD600 of 0.3. Responses were scored from 3 to 8 days post-infiltration, the number of replicates responding to infiltration by (hypersensitive) cell death was counted and the percentage of responsive infiltrations was calculated.

For Rpi-edn2 co-infiltration with effector clones, Agrobacterium suspensions in MMA are prepared at $OD_{600}$=0.5. Successively, a 1:1 mixture of the respective Agrobacterium suspensions is made and infiltrated into the leaves of Nicotiana benthamiana. One week after infiltration the occurrence of hypersensitive cell death is assessed.

Example 1

Screen for Resistance to P. Infestans in S. x Edinense Accessions

To identify a resistant genotype for R gene mapping and cloning, in total 15 genotypes from three S. x edinense accessions were tested for resistance to P. infestans. The 15 individuals were first tested by an in vitro assay with isolate 90128. Fourteen genotypes gave a high level of resistance and one genotype had a lower level of resistance (Table 2). From each accession two highly resistant genotypes per accession were selected. Their resistance to isolate 90128 was confirmed in a detached leaf assay, and inoculation with an additional isolate, IPO-C resulted also in resistant phenotypes. Two field experiments in 2005 and 2007 confirmed the strong resistance to IPO-C in all tested genotypes. Two resistant genotypes edn150-4 and edn151-1 were chosen to generate F1 populations.

Segregation of Resistance in the Mapping Populations

The genotypes edn150-4 and edn151-1 were crossed with cv. Concurrent to generate F1 mapping populations. The F1 individuals were phenotyped for their resistance to four different P. infestans isolates in a detached leaf assay. 159 individuals from the edn150-4 x cv. Concurrent population and 125 from the edn151-1 x cv. Concurrent population were tested. The resistance to each of the four isolates segregated in the two populations (Table 3).

The resistance to 90128 segregated in the two populations. The segregation pattern of the resistance to 90128 was different from the segregation pattern of the resistance to the other isolates. Champouret (2010) cloned two functional R2 homologues (Rpi-edn1.1 and R2-like) in S. x edinense genotype edn151-3. R2 confers resistance to 90128 and susceptibility to the other isolates tested on the population. Therefore, it was hypothesized that the R gene, Rpi-edn1, conferring resistance to 90128 is located in the R2 cluster.

The segregation of the resistance to IPO-C in both populations also followed a different pattern than the segregation of the resistance to isolates PIC99189 and UK7824 (Table 4). This suggested that at least three R-genes are responsible for the observed segregation patterns and that these three genes could be distinguished based on their isolate recognition spectrum.

In summary, the two F1 populations showed similar segregation ratios for resistance and susceptibility (Table 3) to three isolates (90128, 99189 and UK7824) that were independent between isolates (Table 4). The segregation of the resistance to IPO-C is slightly skewed in both populations. But the number of resistant F1 plants is higher for the population edn151-1 x cv. Concurrent whereas the number of susceptible F1 plants is higher for the population edn150-4 x cv. Concurrent. It can be speculated that the same set of three R genes is present in both S. x edinense parental genotypes. Therefore, the rest of the study focused only on one F1 population: edn150-4 x cv. Concurrent.

Marker Development

The population edn150-4 x cv. Concurrent was used to map the R genes segregating in the population. The mapping position of the two genes Rpi-edn1.1, which derived from edn150-4 and R10, which derived from parent Concurrent, are known. So we tested markers known to be present in the locus of interest. For Rpi-edn1.1, located in the R2 cluster on chromosome 4, R2 gene family profiling was performed. R10 maps on chromosome 11 in the R3 cluster (Bradshaw et al. 2006), so CAPS markers from the R3 cluster were tested. The mapping position of the other two genes was unknown, and a genome wide screen was performed. SSR screening and NBS profiling were carried out to determine the map position of the R gene giving resistance to IPO-C and the R gene giving resistance to PIC99189. A subset of F1 individuals resistant or susceptible to all isolates was selected for that purpose. The DNA of the F1 individuals was kept separate for the SSR screening and bulked for the NBS profiling.

Rpi-edn1 from the R2 Cluster is Present in edn150-4

The homologues R2-like and Rpi-edn1.1 have been cloned from the genotype edn151-3, which was derived from the same accession as edn151-1 (Champouret 2010). We investigated whether this gene would also occur in edn150-4. Seven R2 profiling primers (Table 1) were designed on several conserved regions of the R2 gene family. The primers were tested in combination with RsaI, which cuts frequently in the R2 sequence on the parental and F1 bulked DNA. Each primer revealed at least one fragment showing association with the resistance in the bulks. The primer (R2ch4F4) giving the largest number of polymorphic bands was tested on the individuals of the whole population. The resulting NBS marker R2ch4F4-Rsa (fragment of 400 bp) was linked to the resistance to 90128 with 10 recombinants out of 45 individuals (~20 cM). Agro-infiltration assay with PiAvr2 was performed on a subset of the population and it was confirmed that the PiAvr2 response co-segregated with the resistance to 90128 in 40 F1 individuals (FIG. 2).

The presence of Rpi-edn (R2-like or Rpi-edn1.1 or both) on chromosome 4 in the R2 cluster in edn150-4 is thus confirmed.

Rpi-edn2 Maps on Chromosome 9

The screen of the set of approximately 80 SSRs applied on the parents and 24 F1 individuals resulted in one linked marker associated with the resistance to IPO-C. This marker, Stm021, (Table 5) is located on chromosome 9 (Bakker et al., manuscript in preparation). The linkage with resistance to IPO-C was confirmed with 17 recombinants out of 116 individuals (~15 cM).

We propose to call this gene Rpi-edn2, the R gene conferring resistance to IPO-C, located on the long arm of chromosome 9 (FIG. 3). Marker Stm021 is located between two known R gene clusters on chromosome 9: the cluster containing the R genes from S. venturii, Tm-$2^2$ homologues (Foster et al. 2009; Pel et al. 2009) and the cluster containing Rpi-mcq1, also homologous to Tm-$2^2$ (Smilde et al. 2005; patent WO2009013468). Tm-$2^2$ is an R gene from tomato located on the long arm of chromosome 9, conferring resistance to Tobacco Mosaic Virus (Lanfermeijer et al. 2003). More markers were needed to determine whether Rpi-edn2 may be located in one of these clusters. The development of CAPS markers from that region of the genome was not successful as none of the 13 primer combinations tested revealed linkage. So, in order to develop a closely linked marker and determine the exact position of the R gene, a Tm-$2^2$ gene family profiling was performed. Twelve Tm-$2^2$ specific primers (Table 1) were designed and tested in combination with two enzymes RsaI and MseI on the parental and F1 bulked DNA. Two primer/enzyme combinations revealed association with the resistance to IPO-C in the bulks, but only one marker was confirmed. The marker Tm19F-Mse was linked to Rpi-edn2 with 6 recombinants out of 107 individuals (~6 cM). The fragment, of 70 bp, showing association with the phenotype, was cut out from the gel and sequenced. The comparison of this sequence with the Rpi-vnt1 and Rpi-mcq1 genes could not reveal the cluster from which the marker derived. PCR reaction with the start and stop codon primers used for the cloning of Rpi-vnt1 did not give any amplification product on either of the S. x edinense genotypes, suggesting that this cluster was not present in both edn genotypes.

Cloning of Rpi-edn2 Using a Candidate Gene/Allele Mining Approach.

To date, cloning of R genes is typically done through a positional cloning strategy. Once a functional gene is cloned from a specific R locus, one can try to clone functional homologs from the same or different species in order to determine sequence diversification at a given locus. Here we demonstrate that based on a map position combined with a candidate gene mining approach allele specific markers can be generated which can form a starting point for the cloning of the functional R gene.

The inventors adopted a homology based candidate gene mining strategy to clone Rpi-edn2. The first step was to design primers incorporating the putative—start and stop codons of candidate mcq1 gene homologs i.e. mcq-ATG-1 5'-atggctgaaattcttcttac-3', mcq-c1-stop 5'-tcatattctgagctttg-caag-3', mcq-c2-stop 5'-tcatactctcagttttgcaagtc-3' (table 5).

The primer mcq-ATG-1 combined with the primer reverse 2 amplifies the functional gene in mcq.

No amplicons of the expected size were generated with primer set mcq-ATG and mcq-c1-stop when tested on the parental genotypes of both mapping populations. However, when primers mcq-ATG-1 and mcq-c2-stop were combined, a single amplicon of approximately 2.4 kb was amplified in both the resistant as susceptible progeny. Subsequently, PCR products of both susceptible and resistant plant were subjected to restriction digestion using the restriction enzymes MseI, HaeIII, NlaIII, HpaII, DpnII, AluI, HhaI, HinfI, DdeI, HpychIV, RsaI or TaqI. After MseI-digestion a specific restriction fragment of approx. 600 bp was visible that was 100% linked in 60 genotypes segregating for *Phytophthora* resistance.

The undigested PCR products of a resistant plant were cloned into the pGEM$^R$-T Easy vector and 24 individual clones were subjected to enzyme digestion with MseI. A total of 9 different classes could be distinguished based on the MseI digestion pattern. Clones of all 9 classes were sequenced.

The obtained sequences shared 80-90% similarity to each other. Based on MseI digestion pattern clone EDN61 was predicted to cause the polymorphism that co-segregated with Rpi-edn2

A specific SCAR marker was designed for EDN61: EDN F 5'-gcatcatgtctgcacctatg-3' and EDN R 5'ctttgatgtggatg-gatggtg-3' (table 5) in the initial mapping populations. When tested, the marker co-segregated with resistance, confirming that EDN61 was genetically very close to Rpi-edn2 and could potentially be a candidate for Rpi-edn2.

Gene Structure of Rpi-edn2.

The open reading frames of Rpi-edn2 encode predicted peptide of 863 amino acids. The gene is intron-free.

The protein sequences of Rpi-edn2 harbours several conserved motifs of the CC-NBS-LRR class of R proteins (FIG. 8). A coiled-coil (CC) domain is located in the N-terminal part of the proteins between amino acids 1 and 153. In the first 153 residues 3 pairs of putative heptad motifs composed of hydrophobic residues could be recognized in Rpi-edn2. A NB-ARC (nucleotide-binding site, apoptosis, R gene products, CED-4) domain could be recognized in the amino acid stretch between residues 153 and 444 (Ploop, Kinase-2, GLPL) (Van der Biezen and Jones 1998). The C terminal half of Rpi-edn2 comprises a series of 15 LRR motifs of irregular size that can be aligned according to the consensus sequence LxxLxxLxxLxLxxC/N/Sx(x)LxxLPxx where x is any amino acid, and wherein L stands for I, L or V) (McHale et al. 2006).

At the protein level, Rpi-edn2 shares 80% amino acid identity with Rpi-mcq1.1, 77% with Rpi-mcq1.2. Lower percentage homology was found with Rpi-vnt1 (73%) and Tm-2-2 sharing 73% and 72% identity, respectively, showing that Rpi-edn2 defines a new subclass of the Tm2-2 gene family.

Calculated nucleotide identities were as follows:

|  | Rpi-edn2 | Rpi-vnt1 | Rpi-mcq1.1 | Tm2-2 |
|---|---|---|---|---|
| Rpi-edn2 | 100% | | | |
| Rpi-vnt1 | 82% | 100% | | |
| Rpi-mcq1.1 | 87% | 84% | 100% | |
| Tm2-2 | 80% | 80% | 85% | 100% |

Calculated amino acid identities were as follows:

|  | Rpi-edn2 | Rpi-vnt1 | Rpi-mcq1.1 | Tm2-2 |
|---|---|---|---|---|
| Rpi-edn2 | 100% | | | |
| Rpi-vnt1 | 73% | 100% | | |
| Rpi-mcq1.1 | 80% | 76% | 100% | |
| Tm2-2 | 72% | 72% | 77% | 100% |

The above multiple comparisons were performed, using AlignX (Vector NTI Suite Invitrogen) with an engine based on the CLUSTAL matix.

Example 2

Introduction of Rpi-Vnt1, Rpi-Mcq1.1 and Rpi-edn2 into Potato Genotypes Susceptible to *Phytophthora Infestans* and into *N. Benthamiana*

The 2.6 kb fragment of EDN61 was cloned in between the Rpi-blb3 promoter and blb3 terminator, in the binary vector pDEST32 using the protocol described (Lokossou et al 2010). The resulting plasmid was named pDEST:edn2. It was introduced into *Agrobacterium tumefaciens* strain AGL1.

Binary vectors carrying the full-length Rpi-mcq1.1 and Rpi-vnt1 genes (WO2009/013468) are introduced into *Agrobacterium tumefaciens* strains AGL1. To ensure no rearrangements of the plasmids have occurred, plasmid is isolated from resulting transformants, and transformed back into *E. coli* strain DH5-α, digested and compared with digests of the original plasmid stocks.

Potato Transformation

Internodal cuttings from in vitro grown plants cv Desiree were used for transformation by *Agrobacterium tumefaciens* co-cultivation, according to the protocol described by Visser RGF (1991) In: K Lindsey (Ed) Plant Tissue Culture Manual, Kluwer Academic Publishers, Dordrecht/Boston/London, pp. B5: 1-9. Transformants were selected on MS20 medium (Murashige and Skoog, 1962 Physiol Plant 15: 473-497) with 20 g/L sucrose, containing 100 mg/L kanamycin.

*Agrobacterium tumefaciens* culture(s) with the appropriate antibiotic selection regime are set up and grown for 24 hours with shaking at 28° C. Stem internode sections (without nodes) are harvested from 4-6 week old potato cv. Desiree plants grown in aseptic culture on MS medium (2% sucrose). Stem internodes are cut into 2 to 5 mm lengths and placed on two layers of filterpaper on solid R3B media for 1 day before co-cultivation. The R3B medium used contained the salts and vitamins of MS medium (4.71 g/l) plus 3% saccharose, 2 mg/l NAA, 1 mg/l BAP and 0.8% agar, pH 5.8. The layers of filter paper was covered with 2 ml of PACM liquid media consisting of MS (4.71 g/l), 2.0 g/l casein hydrolysate, 3% saccharose, 1 mg/L 2,4 D and 0.5 mg/L kinetine, pH 6.5. 100 ul of overnight. *Agrobacterium tumefaciens* culture is added to stem sections and incubated for 20 minutes at 40 rpm in the dark at 24° C. The stem sections are removed from the *Agrobacterium tumefaciens* suspension, blotted dry and incubated for two days at 21° C. in a 16 hours photoperiod.

After two days the explants were transferred to Zcvh media consisting of 4.71 g/l MS, 2.0% saccharose, 0.8% agar, 200 mg/l cefotaxime, 200 mg/l vancomycine and 1 mg/l zeatine. Stem explants are subcultured onto fresh Zcvh media every 2 weeks for around 3-6 weeks or until the appearance of the first small calli. Once the calli have sufficiently developed the stem sections are transferred onto Zcvh media with selection antibiotics. Stem sections are subcultured every 7-10 days until shoots start to develop. Shoots appear within 2 months from the start of transformation. Shoots are removed with a sharp scalpel and planted into MS20 solid media with selection antibiotics. Transgenic plants harbouring appropriate antibiotic or herbicide resistance genes start to root normally within 2 weeks and are subsequently being transplanted to the glasshouse.

Example 3

Transient Expression in *Nicotiana benthamiana* Transformation pDEST32:edn2 containing the Rpi-edn2 open reading frame under the control of the Rpi-blb3 regulatory sequences, was transformed into *Agrobacterium tumefaciens* strain COR308. This bacterial strain and a strain containing an empty binary vector was agroinfiltrated into *Nicotiana benthamiana* in order to achieve transient expression. Two days after agroinfiltration the leaves were picked and, successively, challenged with *P. infestans* isolates IPO-C and H30PO4 in a detached leaf assay. Five days later, disease symptoms were observed. Leaves that were agroinfiltrated with empty vector showed sporulating lesions (FIG. 6). Leaves infiltrated with constructs pDEST32:edn2, however, did show a hypersensitive response at the site of IPO-C inoculation. At the sites of H30PO4 inoculation an HR free (extreme resistance or XR) type of resistance was observed, showing that the Rpi-edn1 candidate was indeed the gene responsible for recognition of IPO-C, which was mapped to chromosome 9 (FIG. 3).

Effector Screening

In order to further support the unique recognition spectrum of Rpi-edn2 we set out to identify the component from *P. infestans* that is actively recognized by Rpi-edn2. Therefore the leaves of edn150-4 were infiltrated with the *P. infestans* effector collection of approximately 250 clones. As a positive control co-infiltration of R3a and Avr3a was performed and as a negative control the infiltration of pMDC32 alone was used (Table 9). No necrosis (0% of the infiltrated spots) was observed with the vast majority of the effector collection. We did observe recognition of Avr2 and Avr4 but this recognition was co-segregating in the F1 population with the Rpi-edn1 and Rpi-edn3 genes on chromosome 4 and 11 respectively (FIGS. 2 and 3). No responses were observed to effectors that are recognized by other previously cloned R-genes (i.e. Avr3a, Avr-blb1 and Avr-vnt1), showing that recognition of *Phytophthora* by the Rpi-edn2-gene from edn150-4 underlies a new molecular mechanism. Twenty other Pi effector genes present in the effector collection showed a hypersensitive response between 33-100% of the infiltrated spots (Table 9). This experiment again shows that the edn150-4 plant has a new and unique effector recognition spectrum. It remains to be determined which part of this spectrum is caused by Rpi-edn2.

Effector Recognition by Rpi-edn2.

In order to further define the recognition specificity of the cloned gene, Rpi-edn2 was expressed in leaves of *N. benthamiana* simultaneously with the Pi effector proteins listed in Table 9. These Pi effector proteins were found to induce hypersensitive cell death upon their expression in the leaves of edn150-4 from which Rpi-edn2 was cloned. By co-agroinfiltration it was shown that simultaneous expression of Rpi-edn2 and PITG_15039 resulted in a hypersensitive cell death. Infiltration of PITG_15039 alone did cause a slight cell death response but the co-expression with Rpi-edn2 clearly showed an enhanced cell death response, reminiscent of a HR (FIG. 4). This showed that Rpi-edn2 specifically recognised the product of PITG_15039. It must therefore be noted that the screened effector set does not represent the complete effector repertoire of *P. infestans*. Most likely, additional effectors can be identified that produce a HR upon co-infiltration with the Rpi-edn2 gene. These additional effectors might be homologous to PITG_15039 and might be a more preferred substrate for receptor ligand interactions as could be apparent by the induction of a stronger or faster HR upon co-infiltration. Rpi-edn2 is 80% or less homologous to both Mcq1.1 and Rpi-vnt1 (see above). By analysis of the Rpi-edn2 *Phytophthora* isolate resistance spectrum (which is clearly distinct from Rpi-mcq1.1) and by the analysis of the Rpi-edn2 effector recognition spectrum (which does not show Avr-vnt1 recognition), it can be inferred that Rpi-edn2 defines a new subfamily of R-genes which recognises *P. infestans* in a clearly distinct way from the genes described in WO2009/013468.

Complementation Analysis of Rpi-edn2.

A total of 26 *S. tuberosum* cv. Desiree plants capable of growth on kanamycin were selected as putative Rpi-edn2 transformants. Following transfer to the glasshouse, leaves were excised and used in a detached leaf assay with *P. infestans* isolates 90128 and IPO-C to determine whether the transgene conferred blight resistance. Of the 26 transformants, 21 were confirmed as being resistant and did not show any signs of blight infection. Some plants exhibited signs of a hypersensitive response localised to the inoculation site. The remaining 5 plants were susceptible to both isolates, as was the control (non-transformed Desiree). The Rpi-edn2 transgene also conferred resistance to *P. infestans* isolates IPO-0 and EC 1, as detailed in Table 4.

Detached leaves of transgenic potato cv. Desiree carrying Rpi-vnt1 were inoculated with a range of *P. infestans* isolates (Table 5) to determine the range of isolates against which Rpi-vnt1 confers resistance. Of the isolates tested, only isolate EC1 from Ecuador was able to overcome Rpi-vnt1 and cause disease on the inoculated plants.

*S. tuberosum* cv Desiree complemented with pSLJ21153 Rpi-mcq1 (WO2009/013468) were subjected to detached leaf assays using *P. infestans* isolates 90128, EC1, Hica and IPO-complex. For construct pSLJ21153, 12 transgenic lines were shown to be resistant to isolates 90128 and EC1, but susceptible to IPO-complex (Table 5).

These results demonstrate a broad spectrum resistance of Rpi-edn2 to *P. infestans* isolates, substantially different from its homologs Rpi-vnt1 and Rpi-mcq1.

Example 4

Stacking with Other R Genes

In the past, single R genes were quickly overcome after introgression in potato, necessitating for the future a strategy with multiple R genes that need to be combined simultaneously. Since extensive resistance screenings in our laboratory are providing a continuous inflow of novel R genes from a diversity of *Solanum* species, we have a collection of R genes to choose from. The challenge now is to prioritize which R gene should be cloned, and also, which combinations of R genes should be made for application. The main criteria are to achieve a broad spectrum of resistance (acting against many isolates), a high level of the resistance (combining two different weak R genes can still achieve satisfactory level in the field), and enhanced durability (combination of R genes interacting with different effectors may be less easy to break). To select the best R genes, available candidates should be classified. Up till now, R genes can only be classified based on the donor species and their genetic localization (at least before cloning). Here we disclose new ways for classification, mainly based on functionality. R genes can be categorized based on the effector they interact with. An elicitor is typically a pathogen molecule that triggers defense responses resulting in enhanced resistance to an invading pathogen. Examples of elicitors are ATR1, ATR13, Avr1b, AVR3a, IPI-O, Avr-chc1 and elicitors depicted in Table 9.

In yet another embodiment, the invention provides a method for determining whether an R-gene from *Solanum* provides resistance to a variety of *Phytophthora* isolates, comprising providing a plant with said R-gene and testing said plant for a reaction to a defined set of effectors, representing said variety of isolates. This method avoids the use of multiple *Phytophthora* isolates. Such a method provides a better resolution compared to use of a *Phytophthora* isolate. In a preferred embodiment, the invention provides a method for determining whether an R-gene from *Solanum* provides resistance to a variety of *Phytophthora* isolates, comprising providing a plant with said R-gene and testing said plant for a reaction to a defined set of effectors, representing said variety of isolates, wherein at least one said effectors is an elicitor.

Such a method is also very useful in respect of classical breeding in that it can be used to more easily select a suitable variety for crossings.

The invention further provides a method for determining whether a set of R-genes from *Solanum* provides resistance to a variety of *Phytophthora* pathotypes, comprising providing a plant with said set of R-genes and testing said plant for a reaction to a defined set of effectors, representing said variety of pathotypes. This method is very useful in testing the effect of stacked R-genes.

The invention further provides a plant obtainable by the method according to the methods as described above, i.e.

(i) a method for providing a potato plant with a combination of resistance genes which provides resistance against a variety of pathotypes (or strains or isolates) of *Phytophthora*, comprising providing said plant with at least two R-genes that together provide resistance against said variety of pathotypes, said R-genes being identified by a method as described in application, i.e. a method for determining whether an R-gene from *Solanum* provides resistance to a variety of *Phytophthora* pathotypes or (ii) a method for providing a potato plant having acquired resistance to a variety of *Phytophthora* pathotypes through the introduction of an R-gene with additional resistance against at least one additional pathotype of *Phytophthora*, comprising providing said plant with at least one further R-gene obtained by a method as described herein, i.e. a method for identifying a resistance gene (R-gene) in *Solanum* comprising providing a set of defined *Phytophthora* effectors, exposing a part of a *Solanum* plant to said set of defined effectors, identifying the presence or absence of a reaction of said plant to an effector from said set of defined effectors, transferring at least part of the nucleic acid sequence of said *Solanum* to another plant and testing the obtained plant or progeny thereof for an acquired reaction against at least one effector from said set of defined effector.

Preferably, said at least one gene of said combination of resistance genes is Rpi-edn2 or said further R-gene is provided with a nucleic acid encoding a further resistance gene, such as Rpi-blb1, -2, -3, Rpi-vnt1, Rpi-chc1, Rpi-avl1-1, Rpi-avl1-2, Rpi-R1, Rpi-R2, Rpi-R3a, Rpi-R3b, Rpi-mcd1 or Rpi-mcq1.

Discussion

Many R gene clusters in *Solanum* have already been identified. A fruitful approach to map novel R genes is to search for association with known R gene clusters. This simplifies R gene mapping, since they should lie in one of the R gene clusters listed in several reviews (Gebhardt et al. 2001; Grube et al. 2000; Pan et al. 2000). The identification of the mapping position of a new potato R gene is still not a routine task, especially in tetraploid (or in general, polyploid) plants. The first step is to identify a susceptible plant for the cross with the resistant genotype. The second step is to choose a *P. infestans* strain that will allow the characterization of the resistance in the F1 individuals. The next step is to confirm that the resistance phenotype is distinct in the population, that the resistance is segregating and that it follows a 1:1 ratio. Once all the conditions are met, the identification of the mapping position can begin. To be successful this step requires a sufficient level of heterozygosity from the resistant parent and an optimal level of polymorphism in the population. For most of these aspects, little can be done to increase the chance of mapping a new R gene. To improve the scoring of the phenotype or the development of linked markers, new approaches have shown to be successful in this study. The response to effectors can be used instead of the resistance phenotype to *P. infestans* to score the population. SSR markers and general or specific profiling approaches can also be useful for the development of diagnostic markers and the identification of the R genes chromosomal position.

A single *P. infestans* strain can contain several effectors and a single genotype can contain several R genes. A good example of this complexity is the isolate UK7824 that contains at least two known Avrs (Avr4 and Avr10), and the two S. x edinense genotypes that contain at least three R genes. This complexity can make R gene mapping a difficult task. For mapping, the gene of interest should be dominant and occur in simplex, or at least be scored as single trait. The use of effectors to score the segregation of the R genes in the F1 population allows the scoring of a single R gene recognizing a specific effector. The responses to Avr2 and Avr4 segregating in the F1 population were associated with resistance to 90128 and PIC99189, respectively. It shows that effector responses can be used to phenotype an F1 population and map an R gene, which can be very useful in the presence of multiple R genes in a single genotype. Having the avirulence gene to R10 (Avr10) would allow the scoring of the plants for the presence of R10 and simplify its mapping.

SSR marker screening and NBS profiling are the two approaches used in this study to identify R genes map position. NBS profiling identified the mapping position of Rpi-edn3 on chromosome 11 and SSR marker the one of Rpi-edn2 on chromosome 9. Both marker technologies are suitable for polyploids and are complementary to each other. SSR marker screening is an addition to the NBS profiling to identify R gene map position. A large set of SSR markers that cover the potato genome is now available (Collins et al. 1999; Feingold et al. 2005; Ghislain et al. 2004). Bakker et al., (manuscript in preparation) have developed the largest and most useful set of SSR markers for R gene mapping purposes because the primers were designed from BAC sequences selected with R gene analogue (RGA) probes and mapped in R gene clusters in the SH x RH UHD genetic map (van Os et al. 2006). These SSR markers allow the identification of a position of a gene for novel resistance on a chromosomal arm. For mapping purposes, the SSR marker screen approach has several technical advantages. The presence of polymorphism and its segregation in the population is determined directly with one PCR. One primer combination shows several alleles, which means that the probability to determine which allele is associated with the resistance, especially for polyploid populations, is higher than with other marker approaches. Another advantage of the SSR marker approach for R genes mapping is that the mapping position of each marker is already known. So the identification of a marker associated with a novel resistance will directly assign the R gene to a particular chromosome arm, and hence a probable R gene cluster.

NBS profiling was designed to specifically target R genes but it can easily be adapted to target other conserved gene families. It was adapted for peroxidase profiling in barley to map peroxidase clusters on the genome and correlate them with resistance QTL map position (González et al. 2010). In this study, we adapted the NBS profiling to specific R gene families and showed its success for three R gene families: R2, Tm2 and the N gene family. R genes from the same cluster usually have similarities in their sequences not shared with other R genes (McDowell et al. 2006; Meyers et al. 2005) so it is possible to design specific primers for a particular R gene cluster. Sequence information on R genes is largely available and more sequences will become available with potato genome sequencing. This approach could be developed for each R gene cluster and could be an addition to the standard NBS profiling or SSR marker screen for R gene mapping purposes.

S. x Edinense, a Lesson from Nature on R Gene Stacking

S. x edinense shows a high level of resistance in the different assays and the resistance seems well established in the natural population and effective to a wide range of *Phytophthora infestans* isolates. Breeders would very much like to introduce such a level of wide spectrum resistance in their varieties. This study revealed that the resistance observed in two S. x edinense genotypes is explained by the presence of at least three genes that each has been overcome by some *P. infestans* strains. Each Rpi-edn gene causes resistance to an isolate to which none of the other Rpi-edn genes confer resistance. This suggests a natural stacking of R genes that may be caused by selection pressure to keep all three R genes together in most genotypes of the species. The second aspect that could explain the level of resistance in S. x edinense is the provenance of the stacked R genes. S. x edinense is a natural hybrid between *S. demissum* and *S. tuberosum* ssp. *andigena* (Serquen et al. 2002). *S. demissum* originates from Mexico (Watanabe et al. 1991) and *S. tuberosum* ssp. andigena from Bolivia where it was domesticated (Van Soest et al. 1984). The centre of origin of *P. infestans* still has not been determined. Some studies brought evidence favoring a Mexican origin, and more recent studies suggest a South American origin (Gomez-Alpizar et al. 2007). Presently, Mexico and South America are both considered as centers of diversity of *P. infestans*. This implies a co-evolution between the pathogen and the plant host in both regions, so R genes have evolved in both places, and may have evolved differently. Wild *Solanum* species originating from a center of diversity should be a valuable source for resistance and for stacking (Goodwin 1994). As presented in FIG. 5, it can be postulated that the resistance in S. x edinense is the result of a combination of R genes from the two centers of diversity of *P. infestans*. Rpi-edn1 (R2 homologue) and Rpi-edn3 (R4 homologue) originate from the Mexican *S. demissum* species. Rpi-edn2 could come from South-American *S. tuberosum* spp. andigena, since the other *Solanum* R genes in the Tm2 cluster also occurred in *Solanum* species that originated so far only from South America: Rpi-vnt1 and Rpi-mcq1 (Foster et al. 2009; Pel et al. 2009).

In conclusion, the investigation of inheritance of stacked R genes in potato genotypes can be made easier by using Avr genes from the complementing R genes and R gene cluster specific markers. If that is not possible, more generations of backcrossing are needed to unravel the nature of the different R genes involved. The natural stacking of broken R genes located on different clusters and originating from geographically distinct centers of diversity of *P. infestans* confers a strong level of resistance in S. x edinense. This study shows that stacking of R genes does occur in nature and seems to be a successful strategy to fend off the pathogen. It may be taken as a natural proof of principle, and applied in an agricultural context as a strategy to achieve durable resistance.

Example 5

The coding sequence from Rpi-edn2 was isolated by a PCR approach. In order to isolate the Rpi-edn2 gene, including the promotor and terminator sequences, a bacterial artificial chromosome (BAC) library was constructed. Chromosome sized genomic DNA from edn140-5 was isolated and mechanically sheared. Fragments of around 80 kb were ligated into pCC1BAC. A library consisting of 200.000 clones, providing a 10× coverage of the genome, was divided into 600 pools of over 300 colonies each. The pools were screened using Rpi-edn2 specific PCR marker that was listed in the initial application. Eight colonies proved to be positive in this PCR screen and one pool was selected to identify the individual BAC clone containing the Rpi-edn2 gene. Individual colonies from the positive BAC pool were screened and identified a clone with an insert of around 26 kb. Sequence analysis of the entire BAC clone (FIG. 8) revealed that indeed the Rpi-edn2 gene was present. As shown in FIGS. 8 and 9, besides the Rpi-edn2 gene, also two additional putative genes were found that encode Rpi-edn2 homologs. Gene b was encoding only a partial NB-LRR sequence, that was distributed over four different exons. Gene c contained only a single exon and encoded a complete CC-NB-LRR protein. Interestingly at the beginning of the BAC insert (gene a) a mutator type of transposable element was found. Such mobile elements are associated with many known resistance gene clusters.

Methods:

Plant material. Clone edn150-4 was maintained in the laboratory of Plant Breeding by in vitro culture. BAC library construction was performed at RXbioscience (Rockville, USA).

PCR screening with the Rpi-edn2 specific marker was performed as described in the initial application.

Sequence analysis of the BAC clone was performed at Macrogen (Seoul, South Korea) using a 454 sequencer (Roche).

Gene prediction was performed using the FGENESH algorythm(linux1.softberry.com/berry.phtml?topic=fgenesh&group=programs&subgroup=gfind).

TABLE 1

*Phytophthora infestans* isolates used to phenotype the two segregating populations. The column effector indicates the avirulent effector present in the isolates recognized by the R gene to induce resistance.

| Isolate | Country of Origin | Race | Effector |
|---|---|---|---|
| 90128 | The Netherlands | 1, 3, 4, 7, 8, 10, 11 | PiAvr2 |
| IPO-C | Belgium | 1, 2, 3, 4, 5, 6, 7, 10, 11 | Unknown |

TABLE 1-continued

*Phytophthora infestans* isolates used to phenotype the two segregating populations. The column effector indicates the avirulent effector present in the isolates recognized by the R gene to induce resistance.

| Isolate | Country of Origin | Race | Effector |
|---|---|---|---|
| PIC99189 | Mexico | 1, 2, 5, 7, 10, 11 | Avr4 |
| IPO-0 | Unknown | 3b, 4, 7, 10, 11 | |
| 91011 | The Netherlands | 3, 4, 5, 10 | |
| VK98014 | The Netherlands | 1, 2, 4, 11 | |
| NL00228 | The Netherlands | 1, 2, 4, 7 | |
| IPO428-2 | The Netherlands | 1, 3, 4, 7, 8, 10, 11 | |
| H30P04 | The Netherlands | 3a, 7, 10, 11 | |
| N1050194 | The Netherlands | Nd | |
| USA618 | Mexico | 1, 2, 3, 6, 7, 10, 11 | |
| NL01096 | The Netherlands | 1, 3, 4, 7, 8, 10, 11 | |
| 3128-A | Unknown | Nd | |
| PIC99177 | Mexico | 1, 2, 3, 4, 7, 9, 11 | |
| UK7824 | United Kingdom | 1, 2, 3, 6, 7 | Avr4 and Avr10 |

TABLE 2

Resistance to two *Phytophthora infestans* isolates of 15 *S. x edinense* genotypes from three different accessions under three different assays: an in vitro assay, detached leaf assay (DLA) and field trial in two years. Resistance phenotype is characterized on the scale from 1 (susceptible) to 9 (resistant). Edn for *S. x edinense* and dms for *S. demissum*. In shadow grey, the genotypes used in DLA and field experiments, in bold the genotypes used in this study. (GLKS 25492: edn151; GLSK 25493: edn150; GLSK 25494: edn152).

| Genotypes | | In vitro 90128 | DLA 90128 | DLA IPO-C | Field 2005 IPO-C | Field 2007 IPO-C |
|---|---|---|---|---|---|---|
| edn | 150-1 | 7 | nd | nd | nd | nd |
| edn | 150-2 | 9 | 9 | 9 | 9 | nd |
| edn | 150-3 | 9 | nd | nd | nd | nd |
| edn | 150-4 | 9 | 9 | 9 | 9 | 9 |
| edn | 150-5 | 9 | nd | nd | nd | nd |
| edn | 151-1 | 9 | 9 | 9 | 9 | 9 |
| edn | 151-2 | 9 | nd | nd | nd | nd |
| edn | 151-3 | 9 | 9 | 9 | 9 | 9 |
| edn | 151-4 | 9 | nd | nd | nd | nd |
| edn | 151-5 | 9 | nd | nd | nd | nd |
| edn | 152-1 | 9 | 9 | 8 | 9 | nd |
| edn* | 152-2 | 9 | 9 | 7 | 9 | nd |
| edn | 152-3 | 9 | nd | nd | nd | nd |
| edn | 152-4 | 9 | nd | nd | nd | nd |
| edn | 152-5 | 5 | nd | nd | nd | nd |
| Bintje | | 2 | 2 | 2 | 2 | 2 |
| dms | 344-14 | 9 | 9 | 9 | nd | nd |
| dms | 344-18 | nd | 9 | 9 | 9 | 9 |

TABLE 3

Description of the F1 populations and their responses to the different *Phytophthora infestans* isolates in detached leaf assay.

| R parent | S parent | Pop. size | 90128* R | 90128* S | 90128* Q | IPO-C R | IPO-C S | IPO-C Q | PIC99189 R | PIC99189 S | PIC99189 Q | UK7824 R | UK7824 S | UK7824 Q |
|---|---|---|---|---|---|---|---|---|---|---|---|---|---|---|
| edn150-4 | cv. Concurrent | 125 | 37 | 24 | 10 | 37 | 52 | 36 | 40 | 64 | 21 | 54 | 27 | 44 |
| edn151-1 | cv. Concurrent | 159 | 27 | 17 | 13 | 70 | 50 | 39 | 51 | 76 | 32 | 66 | 34 | 59 |

*The number of F1 individuals phenotyped with isolate 90128 was smaller than for the other isolates (71 from the 159 plants were scored for edn150-4 x cv. Concurrent population and 57 from the 125 for edn151-1 x cv. Concurrent population).

TABLE 4

Segregation of the resistance in two F1 populations to three different isolates: IPO-C, PIC99189 and UK7824. Percentage of the number of plants showing a particular combination of resistance to each of the three isolates compared to total number of plants for which we have complete data. All possible resistant combinations are indicated here but not all are observed.

| Combinations | IPO-C | PIC99189 | UK7824 | edn150-4 x concurrent (%)[1] | edn151-1 x concurrent (%)[2] |
|---|---|---|---|---|---|
| 1 | R | R | R | 30 | 31 |
| 2 | S | R | R | 23 | 24 |
| 3 | S | S | S | 20 | 22 |
| 4 | R | S | S | 9 | 2 |
| 5 | S | S | R | 1 | 4 |
| 6 | R | S | R | 17 | 17 |
| 7 | R | R | S | 0 | 0 |
| 8 | S | R | S | 0 | 0 |

[1] 70 individuals in total.
[2] 54 individuals in total (Excluding the unclear phenotype Q).

TABLE 5

Markers used for mapping of Rpi-edn1, Rpi-edn2, Rpi-edn3 and R10 in the F1 population edn150-4 x cv. Concurrent. TM = 55° C. for all markers. (*Nbs15F is a degenerate primer)

| Type | Marker | Primer sequence or reference | Enzyme | Chr. (cluster) |
|---|---|---|---|---|
| NBS profiling | NBS5a | Van der Linden et al., 2004 | RsaI | 11(N) |
| NBS profiling | GLPL6 | Van der Linden et al., 2004 | MseI | 11 (N) |
| CAPS | Ct182 | Brigneti et al., 1997 | HpyF10VI | 11 (N) |
| CAPS | Gp163 | Brigneti et al., 1997 | MseI | 11 (N) |
| N profiling | Nbs15F-Mse* | atgcatgayttratwvaagab atggg | MseI | 11 (N) |
| SSR | Stm021 | Collins et al.,1999 | a.s. | 9 |
| Tm2 profiling | Tm19F-Mse | actgccaaattgtatggtg | MseI | 9 |
| mcq-ATG-1 | | atggctgaaattcttcttac | | 9 |
| mcq-c1-stop | | tcatattctgagctttgcaag | | 9 |
| mcq-c2-stop | | tcatactctcagttttgcaagtc | | 9 |
| EDN-F | | gcatcatgtctgcacctatg | | 9 |
| EDN-R | | ctttgatgtggatggatggtg | | 9 |
| R2 profiling | R2ch4F4-Rsa | tgtgcagtgataacagcttca | RsaI | 4 (R2) |
| CAPS | Gp283 | F tactcaaggagtctgcatgg R aacttcctgtccgaatgtcc | RsaI | 11 (R3) |

TABLE 6

Response of Rpi-vnt1, Rpi-mcq1 and Rpi-edn2 transgenic potato plants against a range of P. infestans isolates.

| Isolate | Country of Origin | Race | Rpi-vnt1 | Rpi-mcq1 | Rpi-edn2 |
|---|---|---|---|---|---|
| 90128 | The Netherlands | 1, 3, 4, 7, 8, 10, 11 | R | R | R |
| IPO-C | Belgium | 1, 2, 3, 4, 5, 6, 7, 10, 11 | R | S | R |
| IPO-0 | | | R | R | R |
| EC1 | Ecuador | 3.4.7.11 | S | R | R |

TABLE 7

R2, Tm2 and N-like profiling primers.

| Profiling | Primer name | Sequence |
|---|---|---|
| R2 | R2ch4-F1 | TGTTTGAGATCAACTCTATTGCTAATG (SEQ ID NO: 13) |
| R2 | R2ch4-F2 | CAATTGTTGTATTGAGCGGACT (SEQ ID NO: 14) |
| R2 | R2ch4-F3 | GGAAAGATGTTGACCCTGTTG (SEQ ID NO: 15) |
| R2 | R2ch4-F4 | TGTGCAGTGATAACAGCTTCA (SEQ ID NO: 16) |
| R2 | R2ch4-R2 | GCTGCTAATGTTGTTTAGGGAGT (SEQ ID NO: 17) |
| R2 | R2ch4-R3 | TGGATCGAAGAACATAATTGACC (SEQ ID NO: 18) |
| R2 | R2ch4-R4 | AATGACTCTGCTTCCATTCTTG (SEQ ID NO: 19) |
| Tm2 | Tm1-R | CATTTCTCTCTGGAGCCAATC (SEQ ID NO: 20) |
| Tm2 | Tm1-F | GAGAGAAATGAGACACATTCG (SEQ ID NO: 21) |
| Tm2 | Tm3-F | GCGGATGAGTTTGCTATGGAG (SEQ ID NO: 22) |
| Tm2 | Tm3-R | CTCCATAGCAAACTCATCCGC (SEQ ID NO: 23) |
| Tm2 | Tm6-F | TGTTTCMATAGTTGGCATGCC (SEQ ID NO: 24) |
| Tm2 | Tm15-F | AGTTTGTGTGTGGACTTGGC (SEQ ID NO: 25) |
| Tm2 | Tm15-R | GTAACAAGTCATGTATGCGAC (SEQ ID NO: 26) |

TABLE 7-continued

R2, Tm2 and N-like profiling primers.

| Profiling | Primer name | Sequence |
|---|---|---|
| Tm2 | Tm19-F | GCCAAATAGTATTGTCAAGCTC (SEQ ID NO: 27) |
| Tm2 | Tm19-R | GAGCTTGACAATACTATTTGGC (SEQ ID NO: 28) |
| Tm2 | Mcq19-F | ACTGCCAAATTGTATGGTG (SEQ ID NO: 29) |
| Tm2 | Mcq21-R | ATTGGTGCAACAATCTCGCC (SEQ ID NO: 30) |
| Tm2 | Mcq23-F | GAATGTTTGCGGAAGAATGCG (SEQ ID NO: 31) |
| N | Nbs13-R | AAGAARCATGCDATATCTARAAATAT (SEQ ID NO: 32) |
| N | Nbs12-R | YTTSARSGCTAAAGGRAGRCC (SEQ ID NO: 33) |
| N | Nbs12-F | CTTTAGCBYTSAARKTGTKKGG (SEQ ID NO: 34) |
| N | Nbs15-F | ATGCATGAYTTRATWVAAGABATGGG (SEQ ID NO: 35) |
| N | Tir270-F | TATGCTACRTCDAGNTGGTGC (SEQ ID NO: 36) |
| N | Tir300-F | NTAGTRAAGAYATGGAATGC (SEQ ID NO: 37) |
| N | Lrr3050-R | YGATGGTGGAACCAHCTTGGG (SEQ ID NO: 38) |
| N | Lrr3150-R | CAGAGTAACATACARCAAATCCC (SEQ ID NO: 39) |

TABLE 8

R-genes and quantitative trait loci for late blight resistance reported for wild Solanum species

| Wild species | Locus type or name | Also known as | Chromosome | cloned | Reference |
|---|---|---|---|---|---|
| S. berthaultii | QTLs (4) | | I, III, VII and XI | | |
| | Rpi-ber | | X | | (Rauscher et al., 2006) |
| | Rpi-ber1 | | X | | (Park et al.) |
| | Rpi-ber2 | | X | | (Park et al.) |
| S. bulbocastanum | RB/Rpi-blb1 | RB | VIII | yes | (Song et al., 2003; van der Vossen et al., 2003) |
| | Rpi-blb2 | | VI | yes | Van der Vossen et al. 2005 |
| | Rpi-blb3 | | IV | yes | (Park et al., 2005a) |
| S. caripense | QTL (2) | | unassigned | | |
| S. demissum | R1 | | V | yes | (Ballvora et al., 2002) |
| | R2 | | IV | yes | (Park et al., 2005b) |
| | R3, R6, R7 | | XI | | |
| | R3a | | XI | yes | (Huang et al., 2005) |
| | R3b | | XI | | |
| | R5-R11 | | XI | | |
| | R10, R11 | | XI | | (Bradshaw et al., 2006) |
| S. microdontum | QTLs (3) | | IV, V and X | | (Tan et al., 2008) |
| | QTL | | Unassigned | | |
| S. mochiquense | Rpi-mcq1 | (Rpi-moc1) | IX | yes | |
| S. papita | Rpi-pta1 | | VIII | yes | (Vleeshouwers et al., 2008) |
| S. paucissectum | QTLs (3) | | X, XI and XII | | |
| S. phureja | Rpi-phu1 | | IX | | |
| S. pinnatisectum | Rpi-pnt1 | (Rpi1) | VII | | (Kuhl et al., 2001) |
| S. stoloniferum | Rpi-sto1 | | VIII | yes | (Wang et al., 2008) |
| S. venturii | Rpi-vnt1.1 | Rpi-phu1 | IX | yes | Foster et al. 2009 |
| | Rpi-vnt1.3 | | IX | yes | Pel et al. 2009 |
| S. vernei | QTLs (several) | | VI, VIII, IX | | |
| Hybrids with S. tuberosum | Rpi-abpt | | IV | yes | Lokosou et al. 2009 |
| | R2-like | | IV | yes | (Park et al., 2005b) |

TABLE 9

Pi-effector recognition spectrum of the edn150-4 plant.

| T30-4 gene # | percentage of infiltration sites in edn150-4 producing hypersensitive cell death |
|---|---|
| PITG_00774 | 33 |
| PITG_20336 | 83 |
| PITG_09716 | 39 |
| PITG_10465 | 20 |
| PITG_14093 | 64 |
| PITG_14360 | 36 |
| PITG_15110 | 35 |
| PITG_20301 | 100 |
| PITG_20303 | 100 |
| PITG_20300 | 78 |
| PITG_22880 | 100 |
| PITG_09616 | 64 |
| PITG_10540 | 100 |
| PITG_15039 | 83 |
| PITG_04097 | 100 |
| PITG_04169 | 86 |
| PITG_16726 | 83 |
| PITG_23131 | 83 |
| PITG_07550_9 | 100 |
| R3a | 0 |
| Avr3a | 0 |
| Avr2 | 90 |
| Avr-vnt1 | 0 |
| Avr4 | 80 |
| Avr-blb1 | 0 |
| R3a-Avr3a | 50 |
| pM DC32 | 0 |

REFERENCES

Armstrong M R, Whisson S C, Pritchard L, Bos J I B, Venter E, Avrova A O, Rehmany A P, Böhme U, Brooks K, Cherevach I, Hamlin N, White B, Fraser A, Lord A, Quail M A, Churcher C, Hall N, Berriman M, Huang S, Kamoun S, Beynon J L, Birch P R J (2005) An ancestral oomycete locus contains late blight avirulence gene Avr3a, encoding a protein that is recognized in the host cytoplasm. Proceedings of the National Academy of Sciences of the United States of America 102: 7766-7771

Bos J I B, Kanneganti T D, Young C, Cakir C, Huitema E, Win J, Armstrong M R, Birch P R J, Kamoun S (2006) The C-terminal half of *Phytophthora infestans* RXLR effector AVR3a is sufficient to trigger R3a-mediated hypersensitivity and suppress INF1-induced cell death in *Nicotiana benthamiana*. Plant Journal 48: 165-176

Bradshaw J E, Bryan G J, Lees A K, McLean K, Solomon-Blackburn R M (2006) Mapping the R10 and R11 genes for resistance to late blight (*Phytophthora infestans*) present in the potato (*Solanum tuberosum*) R-gene differentials of Black. Theoretical and Applied Genetics 112: 744-751

Champouret N (2010) Functional Genomics of *Phytophthora infestans* Effectors and *Solanum* Resistance Genes. PhD thesis Wageningen University, Wageningen Champouret N, Bouwmeester K, Rietman H, van der Lee T, Maliepaard C, Heupink A, van de Vondervoort P J I, Jacobsen E, Visser R G F, van der Vossen E A G, Govers F, Vleeshouwers V (2009) *Phytophthora infestans* isolates lacking class I ipiO variants are virulent on Rpi-blb1 potato. Molecular Plant-Microbe Interactions 22: 1535-1545

Collins A, Milbourne D, Ramsay L, Meyer R, Chatot-Balandras C, Oberhagemann P, De Jong W, Gebhardt C, Bonnel E, Waugh R (1999) QTL for field resistance to late blight in potato are strongly correlated with maturity and vigour. Molecular Breeding 5: 387-398

Colon L T, Budding D J (1988) Resistance to late blight (*Phytophthora-infestans*) in 10 wild *Solanum* species. Euphytica: 77-86

Dangl J L, Jones J D G (2001) Plant pathogens and integrated defence responses to infection. Nature 411: 826-833

ElKharbotly A, Jacobs J M E, Hekkert B T L, Jacobsen E, Ramanna M S, Stiekema W J, Pereira A (1996) Localization of Ds-transposon containing T-DNA inserts in the diploid transgenic potato: Linkage to the R1 resistance gene against *Phytophthora infestans* (Mont) de Bary. Genome 39: 249-257

Feingold S, Lloyd J, Norero N, Bonierbale M, Lorenzen J (2005) Mapping and characterization of new EST-derived microsatellites for potato (*Solanum tuberosum* L.). Theoretical and Applied Genetics 111: 456-466

Foster S J, Park T H, Pel M, Brigneti G, Sliwka J, Jagger L, van der Vossen E, Jones J D G (2009) Rpi-vnt1.1, a Tm-$2^2$ Homolog from *Solanum venturii*, Confers Resistance to Potato Late Blight. Molecular Plant-Microbe Interactions 22: 589-600

Fry W E (1978) Quantification of general resistance of potato cultivars and fungicide effects for integrated control of potato late blight. Phytopathology 68: 1650-1655

Gebhardt C, Valkonen J P T (2001) Organization of genes controlling disease resistance in the potato genome. Annual Review of Phytopathology 39: 79-102

Ghislain M, Spooner D M, Rodriguez F, Villamon F, Nunez J, Vasquez C, Waugh R, Bonierbale M (2004) Selection of highly informative and user-friendly microsatellites (SSRs) for genotyping of cultivated potato. Theoretical and Applied Genetics 108: 881-890

Glendinning D R (1983) Potato introductions and breeding up to the early 20th-century. New Phytologist 94: 479-505

Gomez-Alpizar L, Carbone I, Ristaino J B (2007) An Andean origin of *Phytophthora infestans* inferred from mitochondrial and nuclear gene genealogies. Proceedings of the National Academy of Sciences of the United States of America 104: 3306-3311

González A M, Marcel T C, Kohutova Z, Stam P, van der Linden C G, Niks R E (2010) Peroxidase profiling reveals genetic linkage between peroxidase gene clusters and basal host and non-host resistance to rusts and mildew in barley. PLoS-ONE submitted Goodwin S B, Cohen, B. A., and Fry, W. E. (1994) Plan-global distribution of a single clonal lineage of the Irish potato famine fungus. Proc. Natl. Acad. Sci. USA 91: 11591-11595.

Grube R C, Radwanski E R, Jahn M (2000) Comparative genetics of disease resistance within the solanaceae. Genetics 155: 873-887

Huang S (2005) Discovery and characterization of the major late blight resistance complex in potato. PhD thesis Wageningen University, Wageningen Huang S W, van der Vossen E A G, Kuang H, Vleeshouwers V, Zhang N R, Borm T J A, van Eck H J, Baker B, Jacobsen E, Visser R G F (2005) Comparative genomics enabled the isolation of the R1a late blight resistance gene in potato. Plant Journal 42: 251-261

Huang S W, Vleeshouwers V, Werij J S, Hutten R C B, van Eck H J, Visser R G F, Jacobsen E (2004) The R3 Resistance to *Phytophthora infestans* in Potato is Conferred by Two Closely Linked R Genes with Distinct Specificities. Molecular Plant-Microbe Interactions 17: 428-435

Karimi M, Inze D, Depicker A (2002) GATEWAY(TM) vectors for *Agrobacterium*-mediated plant transformation. Trends in Plant Science 7: 193-195

Lanfermeijer F C, Dijkhuis J, Sturre M J G, De Haan P, Hille J (2003) Cloning and characterization of the durable tomato mosaic virus resistance gene Tm-$2^2$ from *Lycopersicon esculentum*. Plant Molecular Biology 52: 1037-1049

Lazo G R, Stein P A, Ludwig R A (1991) A DNA transformation-competent *Arabidopsis* genomic library in *Agrobacterium*. Bio-Technology 9: 963-967

Lokossou A (2010) Dissection of the major late blight resistance cluster on potato linkage group IV. PhD thesis Wageningen University, Wageningen Lokossou A, Park T H, van Arkel G, Arens M, Ruyter-Spira C, Morales J, Whisson S C, Birch P R J, Visser R G F, Jacobsen E, van der Vossen E A G (2009) Exploiting Knowledge of R/Avr Genes to Rapidly Clone a New LZ-NBS-LRR Family of Late Blight Resistance Genes from Potato Linkage Group IV. Molecular Plant-Microbe Interactions 22: 630-641

Malcolmson J F, Black W (1966) New R genes in *Solanum demissum* lindl. and their complementary races of *Phytophthora infestans* (Mont.) de bary. Euphytica 15: 199-203

Mastenbroek C (1953) Experiments on the inheritance of blight immunity in potatoes derived from *Solanum demissum* Lindl. Euphytica 2: 197-206

McDowell J M, Simon S A (2006) Recent insights into R gene evolution. Molecular Plant Pathology 7: 437-448

McDowell J M, Woffenden B J (2003) Plant disease resistance genes: recent insights and potential applications. Trends in Biotechnology 21: 178-183

Meyers B C, Kaushik S, Nandety R S (2005) Evolving disease resistance genes. Current Opinion in Plant Biology 8: 129-134

Meyers B C, Kozik A, Griego A, Kuang H, Michelmore R W (2003) Genome-wide analysis of NBS-LRR-encoding genes in *Arabidopsis*. Plant Cell 15: 809-834

Michelmore R W, Paran I, Kesseli R V (1991) Identification of markers linked to disease-resistance genes by bulked segregant analysis—a rapid method to detect markers in specific genomic regions by using segregating populations. Proceedings of the National Academy of Sciences of the United States of America 88: 9828-9832

Mohan M, Nair S, Bhagwat A, Krishna T G, Yano M, Bhatia C R, Sasaki T (1997) Genome mapping, molecular markers and marker-assisted selection in crop plants. Molecular Breeding 3: 87-103

Oh S K, Young C, Lee M, Oliva R, Bozkurt T O, Cano L M, Win J, Bos J I B, Liu H Y, Van Damme M, Morgan W, Choi D, Van Der Vossen E A G, Vleeshouwers V G A, Kamoun S (2009) In Planta Expression Screens of *Phytophthora infestans* RXLR Effectors Reveal Diverse Phenotypes, Including Activation of the *Solanum bulbocastanum* Disease Resistance Protein Rpi-blb2[W]. Plant Cell 21: 2928-2947

Pan Q, Liu Y S, Budai-Hadrian O, Sela M, Carmel-Goren L, Zamir D, Fluhr R (2000) Comparative genetics of nucleotide binding site-leucine rich repeat resistance gene homologues in the genomes of two dicotyledons: Tomato and *Arabidopsis*. Genetics 155: 309-322

Park, T. H., Vleeshouwers, V. G. A. A., Huigen, D. J., van der Vossen, E. A. G., van Eck, H. J. and Visser, R. G. F. (2005) Characterization and high-resolution mapping of a late blight resistance locus similar to R2 in potato. TAG. Theoretical and applied genetics, 111, 591-597.

Pavek J, Corsini D L (2001) Utilization of potato genetic resources in variety development. American Journal of Potato Research 78: 433-441

Pel M (2010) Mapping, Isolation and Characterization of Genes Responsible for Late Blight Resistance. PhD thesis Wageningen University, Wageningen Pel M A, Foster S J, Park T H, Rietman H, van Arkel G, Jones J D G, van Eck H J, Jacobsen E, Visser R G F, van der Vossen E A G (2009) Mapping and Cloning of Late Blight Resistance Genes from *Solanum venturii* Using an Interspecific Candidate Gene Approach. Molecular Plant-Microbe Interactions 22: 601-615

Pink D, Puddephat I (1999) Deployment of disease resistance genes by plant transformation—a 'mix and match' approach. Trends in Plant Science 4: 71-75

Pink D A C (2002) Strategies using genes for non-durable disease resistance. Euphytica 124: 227-236

Rauscher G M, Smart C D, Simko I, Bonierbale M, Mayton H, Greenland A, Fry W E (2006) Characterization and mapping of RPi-ber, a novel potato late blight resistance gene from *Solanum berthaultii*. Theoretical and Applied Genetics 112: 674-687

Serquen F C, Hanneman R E (2002) An analysis of the hybrid nature of *Solanum* x edinense Berth. using molecular, cytological and crossability studies. Potato Research 45: 85-97

Smilde W D, Brigneti G, Jagger L, Perkins S, Jones J D G (2005) *Solanum* mochiquense chromosome IX carries a novel late blight resistance gene Rpi-moc1. Theoretical and Applied Genetics 110: 252-258

Tan M Y A, Hutten R C B, Celis C, Park T H, Niks R E, Visser R G F, van Eck H J (2008) The $R_{Pi\text{-}med1}$ Locus from *Solanum* microdontum Involved in Resistance to *Phytophthora infestans*, Causing a Delay in Infection, Maps on Potato Chromosome 4 in a Cluster of NBS-LRR Genes. Molecular Plant-Microbe Interactions 21: 909-918

Tan M Y A, Hutten R C B H, Visser R G F, van Eck H J (2010) The effect of pyramiding *Phytophthora infestans* resistance genes RPi-mcd1 and RPi-ber in potato. Theor Appl Genet in press Torto T A, Li S A, Styer A, Huitema E, Testa A, Gow N A R, van West P, Kamoun S (2003) EST mining and functional expression assays identify extracellular effector proteins from the plant pathogen *Phytophthora*. Genome Research 13: 1675-1685

Toxopeus H J (1964) Treasure-digging for blight resistance in potatoes. Euphytica 13: 206-&

Van Der Fits L, Deakin E A, Hoge J H C, Memelink J (2000) The ternary transformation system: Constitutive VirG on a compatible plasmid dramatically increases *Agrobacterium*-mediated plant transformation. Plant Molecular Biology 43: 495-502

Van der Hoorn R A L, Laurent F, Roth R, De Wit P (2000) Agroinfiltration Is a Versatile Tool That Facilitates Comparative Analyses of Avr9/Cf-9-Induced and Avr4/Cf-4-Induced Necrosis. Molecular Plant-Microbe Interactions 13: 439-446 van der Linden C G, Wouters D, Mihalka V, Kochieva E Z, Smulders M J M, Vosman B (2004) Efficient targeting of plant disease resistance loci using NBS profiling. Theoretical and Applied Genetics 109: 384-393 van der Vossen E, Sikkema A, Hekkert B T L, Gros J, Stevens P, Muskens M, Wouters D, Pereira A, Stiekema W, Allefs S (2003) An ancient R gene from the wild potato species *Solanum bulbocastanum* confers broad-spectrum resistance to *Phytophthora infestans* in cultivated potato and tomato. Plant Journal 36: 867-882 van der Vossen E A G, Gros J, Sikkema A, Muskens M, Wouters D, Wolters P, Pereira A, Allefs S (2005) The Rpi-blb2 gene from *Solanum bulbocastanum* is an Mi-1 gene homolog conferring broad-spectrum late blight resistance in potato. The Plant Journal 44: 208-222 van Os H, Andrzejewski S, Bakker E, Barrena I, Bryan G J, Caromel B, Ghareeb B, Isidore E, de Jong W, van Koert P, Lefebvre V, Milbourne D, Ritter E, van der Voort J, Rousselle-Bourgeois F, van Vliet J, Waugh R, Visser R G F, Bakker J, van Eck H J (2006) Construction of a 10,000-marker ultradense genetic recombination map of potato: Providing a framework for accelerated gene isolation and a genomewide physical map. Genetics 173: 1075-1087 van Poppel P M J A (2009) The *Phytophthora infestans* avirulence gene PiAvr4 and its potato counterpart R4. PhD thesis Wageningen University, Wageningen van Poppel P M J A, Guo J, de Vondervoort P, Jung M W M, Birch P R J, Whisson S C, Govers F (2008) The *Phytophthora infestans* Avirulence Gene Avr4 Encodes an RXLR-dEER Effector. Molecular Plant-Microbe Interactions 21: 1460-1470 van Poppel P M J A, Huigen D J, Govers F (2009) Differential recognition of *Phytophthora infestans* races in potato R4 breeding lines. Phytopathology 99: 1150-1155

Van Soest L J M, Schol̈ber B, Tazelaar M F (1984) Resistance to *Phytophthora infestans* in tuber-bearing species of *Solanum* and its geographical distribution. Potato Research 27: 393-411

Vleeshouwers V, Driesprong J D, Kamphuis L G, Torto-Alalibo T, Van't Slot K A E, Govers F, Visser R G F, Jacobsen E, Kamoun S (2006) Agroinfection-based high-throughput screening reveals specific recognition of INF elicitins in *Solanum*. Molecular Plant Pathology 7: 499-510

Vleeshouwers V, Rietman H, Krenek P, Champouret N, Young C, Oh S K, Wang M Q, Bouwmeester K, Vosman B, Visser R G F, Jacobsen E, Govers F, Kamoun S, Van der Vossen E A G (2008) Effector Genomics Accelerates Discovery and Functional Profiling of Potato Disease Resistance and *Phytophthora Infestans* Avirulence Genes. Plos One 3

Vleeshouwers V, van Dooijeweert W, Keizer L C P, Sijpkes L, Govers F, Colon L T (1999) A laboratory assay for *Phytophthora infestans* resistance in various *Solanum* species reflects the field situation. European Journal of Plant Pathology 105: 241-250

Vleeshouwers V G A, Rietman H (2009) In planta expression systems. Oomycete genetics and Genomics: Diversity, Interactions, and Research Tools. K. Lamour and S. Kamoun, eds. Wiley-Blackwell.: 455-475

Watanabe K, Peloquin S J (1991) The occurrence and frequency of 2n pollen in 2x, 4x, and 6x wild, tuber-bearing *Solanum* species from Mexico, and Central and South America. Theoretical and Applied Genetics 82: 621-626

Whitham S, Dinesh-Kumar S P, Choi D, Hehl R, Corr C, Baker B (1994) The product of the tobacco mosaic virus resistance gene N: Similarity to toll and the interleukin-1 receptor. Cell 78: 1101-1115

Zhu S-x, Zhu J, Li Y, Nijenhuis M, Bergervoet M, Rietman H, Jacobsen E (2010) Broad Spectrum Resistance from Rpi-blb1 Homologous R-genes Has Been Broken by *Phytophthora infestans* Isolates Collected from *Solanum stoloniferum*. Acta Horticulturae Sinica 37: 241-246

INCORPORATION OF SEQUENCE LISTING

Incorporated herein by reference in its entirety is the Sequence Listing for the application. The Sequence Listing is disclosed on a computer-readable ASCII text file entitled "Sequence_listing_294-417PCTUS.txt," created Jan. 25, 2013. The sequence.txt file is 125 kilobyte size.

The invention claimed is:

1. A recombinant vector comprising a nucleic acid sequence encoding SEQ ID NO. 41 or a nucleic acid sequence encoding a polypeptide having at least 95% identity with SEQ ID NO. 41; wherein the nucleic acid sequence is operably linked to a heterologous regulatory sequence and the polypeptide increases resistance to a *Phytophthora* infection when expressed in a plant.

2. The recombinant vector according to claim 1 wherein the recombinant vector comprises SEQ ID NO. 40.

3. A host cell comprising the recombinant vector according to claim 1.

4. A plant cell comprising the recombinant vector according to claim 1.

5. A transgenic plant comprising the plant cell according to claim 4.

6. A part derived from the transgenic plant according to claim 5.

7. An antibody that specifically binds to the protein of SEQ ID NO. 41 or a polypeptide having at least 95% identity with SEQ ID NO. 41; wherein SEQ ID NO. 41 and the polypeptide having at least 95% identity with SEQ ID NO. 41 increases resistance to a *phytophthora* infection when expressed in a plant.

8. A method for increasing resistance in a plant against a *phytophthora* infection comprising providing a plant or a part thereof through transformation with the recombinant vector according to claim 1.

9. The method according to claim 8, wherein said *Phytophthora* comprises *Phytophthora infestans*.

10. The method according to claim 8, wherein said plant is also provided with a nucleic acid encoding a resistance protein selected from the group of Rpi-blb1, Rpi-blb2, Rpi-blb3, Rpi-vnt1, Rpi-chc1, Rpi-edn1, Rpi-edn3, Rpi-mcq1 and combinations thereof.

11. A host cell comprising the recombinant vector according to claim 1, wherein said host cell is selected from the group consisting of an *Agrobacterium* cell and a plant cell.

12. A host cell as in claim 3, wherein said host cell is an *Agrobacterium* cell.

13. A host cell as in claim 3, wherein said host cell is a plant cell.

14. A host cell as in claim 11, wherein said host cell is an *Agrobacterium* cell.

15. A host cell as in claim 11, wherein said host cell is a plant cell.

16. A plant cell comprising the recombinant vector according to claim 1, wherein said plant cell is a cell from a *Solanaceae.*

17. the plant cell as in claim 16, wherein said plant cell is from *Solanum tuberosum.*

18. the plant cell as in claim 16, wherein said plant cell is a tetraploid *Solanum tuberosum.*

19. A method for increasing resistance in a plant against a *Phvtophthora* infection comprising providing a plant or a part thereof through transformation with the recombinant vector according to claim 1, wherein said plant is of a plant from the *Solanaceae* family.

20. the method as in claim 19, wherein said plant is *Solanum tuberosum.*

21. A method for increasing resistance in a plant against a *Phvtophthora* infection comprising providing a plant or a part thereof through transformation with the host cell according to claim 3, preferably wherein said plant is a plant from the *Solanaceae* family.

22. the method as in claim 21, wherein said plant is *Solanum tuberosum.*

23. A method for increasing resistance in a plant against a *Phvtophthora* infection comprising introducing into said plant a nucleic acid sequence encoding a protein comprising SEQ ID NO. 41 or a polypeptide having at least 95% identity with SEQ ID NO. 41; wherein SEQ ID NO. 41 or polypeptide having at least 95% identity with SEQ ID NO. 41 increases resistance to a *Phvtophthora* infection when expressed in said plant, wherein said plant is from the *Solanaceae* family; and selecting said plant the presence of said nucleic acid sequence.

24. the method as in claim 23, wherein said plant is *Solanum tuberosum*.

25. The part according to claim 6, wherein said part is a tuber.

26. The method according to claim 8, wherein said plant is also provided with a nucleic acid encoding a resistance protein comprising SEQ ID NO. 42.

27. The method according to claim 8, wherein said plant is also provided with a nucleic acid encoding a resistance protein comprising SEQ ID NO. 43.

28. The method according to claim 23, wherein said protein is expressed under the control of a heterologous regulatory sequence.

29. The method according to claim 23, wherein the introducing comprises one or more of the following: one or more crossing steps including selfing; backcrossing; and transgenic approaches.

* * * * *

SEQUENCE LISTING

```
<160> NUMBER OF SEQ ID NOS: 48

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
atggctgaaa ttcttcttac                                              20

<210> SEQ ID NO 2
<211> LENGTH: 21
<212> TYPE: DNA
<213> ORGANISM: Artificial
<220> FEATURE:
<223> OTHER INFORMATION: primer

<400> SEQUENCE: 2
tcatattctg agctttgcaa g                                            21

<210> SEQ ID NO 3
<211> LENGTH: 23
<212> TYPE: DNA
<213> ORGANISM: Artificial
```

```
<220> FEATURE:
<223> OTHER INFORMATION: primer

<400> SEQUENCE: 3
tcatactctc agttttgcaa gtc                                              23

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
gcatcatgtc tgcacctatg                                                  20

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
ctttgatgtg gatggatggt g                                                21

<210> SEQ ID NO 6
<211> LENGTH: 23
<212> TYPE: PRT
<213> ORGANISM: Artificial
<220> FEATURE:
<223> OTHER INFORMATION: LRR motif consensus sequence (short)
<220> FEATURE:
<221> NAME/KEY: VARIANT
<222> LOCATION: (1)..(1)
<223> OTHER INFORMATION: Xaa can be L, I, or V
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: Xaa can be L, I, or V
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: VARIANT
<222> LOCATION: (7)..(7)
<223> OTHER INFORMATION: Xaa can be L, I, or V
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: Xaa can be L, I, or V
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: Xaa can be L, I, or V
<220> FEATURE:
<221> NAME/KEY: misc_feature
<222> LOCATION: (13)..(14)
<223> OTHER INFORMATION: Xaa can be any naturally occurring amino acid
```

```
<220> FEATURE:
<221> NAME/KEY: VARIANT
<222> LOCATION: (15)..(15)
<223> OTHER INFORMATION: Xaa can be  C, N, or S
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: VARIANT
<222> LOCATION: (17)..(17)
<223> OTHER INFORMATION: Xaa can be L, I, or V
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: VARIANT
<222> LOCATION: (20)..(20)
<223> OTHER INFORMATION: Xaa can be L, I, or V
<220> FEATURE:
<221> NAME/KEY: misc_feature
<222> LOCATION: (22)..(23)
<223> OTHER INFORMATION: Xaa can be any naturally occurring amino acid

<400> SEQUENCE: 6

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Pro Xaa Xaa
            20

<210> SEQ ID NO 7
<211> LENGTH: 24
<212> TYPE: PRT
<213> ORGANISM: Artificial
<220> FEATURE:
<223> OTHER INFORMATION: LRR motif consensus sequence (long)
<220> FEATURE:
<221> NAME/KEY: VARIANT
<222> LOCATION: (1)..(1)
<223> OTHER INFORMATION: Xaa can be L, I or V
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: Xaa can be L, I or V
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: VARIANT
<222> LOCATION: (7)..(7)
<223> OTHER INFORMATION: Xaa can be L, I or V
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: Xaa can be L, I or V
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: Xaa can be L, I or V
```

```
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: VARIANT
<222> LOCATION: (15)..(15)
<223> OTHER INFORMATION: Xaa can be C, N or S
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: VARIANT
<222> LOCATION: (18)..(18)
<223> OTHER INFORMATION: Xaa can be L, I or V
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: VARIANT
<222> LOCATION: (21)..(21)
<223> OTHER INFORMATION: Xaa can be L, I or V
<220> FEATURE:
<221> NAME/KEY: misc_feature
<222> LOCATION: (23)..(24)
<223> OTHER INFORMATION: Xaa can be any naturally occurring amino acid

<400> SEQUENCE: 7

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Pro Xaa Xaa
            20

<210> SEQ ID NO 8
<211> LENGTH: 26
<212> TYPE: DNA
<213> ORGANISM: Artificial
<220> FEATURE:
<223> OTHER INFORMATION: primer

<400> SEQUENCE: 8
atgcatgayt tratwvaaga batggg                                          26

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
tcatattctg agctttgcaa g                                               21

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
tgtgcagtga taacagcttc a                                               21

<210> SEQ ID NO 11
<211> LENGTH: 20
<212> TYPE: DNA
<213> ORGANISM: Artificial
```

```
<220> FEATURE:
<223> OTHER INFORMATION: primer

<400> SEQUENCE: 11
tactcaagga gtctgcatgg                                               20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
aacttcctgt ccgaatgtcc                                               20

<210> SEQ ID NO 13
<211> LENGTH: 27
<212> TYPE: DNA
<213> ORGANISM: Artificial
<220> FEATURE:
<223> OTHER INFORMATION: profiling primer

<400> SEQUENCE: 13
tgtttgagat caactctatt gctaatg                                       27

<210> SEQ ID NO 14
<211> LENGTH: 22
<212> TYPE: DNA
<213> ORGANISM: Artificial
<220> FEATURE:
<223> OTHER INFORMATION: profiling primer

<400> SEQUENCE: 14
caattgttgt attgagcgga ct                                            22

<210> SEQ ID NO 15
<211> LENGTH: 21
<212> TYPE: DNA
<213> ORGANISM: Artificial
<220> FEATURE:
<223> OTHER INFORMATION: profiling primer

<400> SEQUENCE: 15
ggaaagatgt tgaccctgtt g                                             21

<210> SEQ ID NO 16
<211> LENGTH: 21
<212> TYPE: DNA
<213> ORGANISM: Artificial
<220> FEATURE:
<223> OTHER INFORMATION: profiling primer

<400> SEQUENCE: 16
tgtgcagtga taacagcttc a                                             21

<210> SEQ ID NO 17
<211> LENGTH: 23
<212> TYPE: DNA
<213> ORGANISM: Artificial
<220> FEATURE:
<223> OTHER INFORMATION: profiling primer

<400> SEQUENCE: 17
gctgctaatg ttgtttaggg agt                                           23
```

<210> SEQ ID NO 18
<211> LENGTH: 23
<212> TYPE: DNA
<213> ORGANISM: Artificial
<220> FEATURE:
<223> OTHER INFORMATION: profiling primer

<400> SEQUENCE: 18
tggatcgaag aacataattg acc           23

<210> SEQ ID NO 19
<211> LENGTH: 22
<212> TYPE: DNA
<213> ORGANISM: Artificial
<220> FEATURE:
<223> OTHER INFORMATION: profiling primer

<400> SEQUENCE: 19
aatgactctg cttccattct tg            22

<210> SEQ ID NO 20
<211> LENGTH: 21
<212> TYPE: DNA
<213> ORGANISM: Artificial
<220> FEATURE:
<223> OTHER INFORMATION: profiling primer

<400> SEQUENCE: 20
catttctctc tggagccaat c             21

<210> SEQ ID NO 21
<211> LENGTH: 21
<212> TYPE: DNA
<213> ORGANISM: Artificial
<220> FEATURE:
<223> OTHER INFORMATION: profiling primer

<400> SEQUENCE: 21
gagagaaatg agacacattc g             21

<210> SEQ ID NO 22
<211> LENGTH: 21
<212> TYPE: DNA
<213> ORGANISM: Artificial
<220> FEATURE:
<223> OTHER INFORMATION: profiling primer

<400> SEQUENCE: 22
gcggatgagt ttgctatgga g             21

<210> SEQ ID NO 23
<211> LENGTH: 21
<212> TYPE: DNA
<213> ORGANISM: Artificial
<220> FEATURE:
<223> OTHER INFORMATION: profiling primer

<400> SEQUENCE: 23
ctccatagca aactcatccg c             21

<210> SEQ ID NO 24
<211> LENGTH: 21
<212> TYPE: DNA
<213> ORGANISM: Artificial
<220> FEATURE:
<223> OTHER INFORMATION: profiling primer

```
<400> SEQUENCE: 24
tgtttcmata gttggcatgc c                                           21

<210> SEQ ID NO 25
<211> LENGTH: 20
<212> TYPE: DNA
<213> ORGANISM: Artificial
<220> FEATURE:
<223> OTHER INFORMATION: profiling primer

<400> SEQUENCE: 25
agtttgtgtg tggacttggc                                             20

<210> SEQ ID NO 26
<211> LENGTH: 21
<212> TYPE: DNA
<213> ORGANISM: Artificial
<220> FEATURE:
<223> OTHER INFORMATION: profiling primer

<400> SEQUENCE: 26
gtaacaagtc atgtatgcga c                                           21

<210> SEQ ID NO 27
<211> LENGTH: 22
<212> TYPE: DNA
<213> ORGANISM: Artificial
<220> FEATURE:
<223> OTHER INFORMATION: profiling primer

<400> SEQUENCE: 27
gccaaatagt attgtcaagc tc                                          22

<210> SEQ ID NO 28
<211> LENGTH: 22
<212> TYPE: DNA
<213> ORGANISM: Artificial
<220> FEATURE:
<223> OTHER INFORMATION: profiling primer

<400> SEQUENCE: 28
gagcttgaca atactatttg gc                                          22

<210> SEQ ID NO 29
<211> LENGTH: 19
<212> TYPE: DNA
<213> ORGANISM: Artificial
<220> FEATURE:
<223> OTHER INFORMATION: profiling primer

<400> SEQUENCE: 29
actgccaaat tgtatggtg                                              19

<210> SEQ ID NO 30
<211> LENGTH: 20
<212> TYPE: DNA
<213> ORGANISM: Artificial
<220> FEATURE:
<223> OTHER INFORMATION: profiling primer

<400> SEQUENCE: 30
attggtgcaa caatctcgcc                                             20
```

```
<210> SEQ ID NO 31
<211> LENGTH: 21
<212> TYPE: DNA
<213> ORGANISM: Artificial
<220> FEATURE:
<223> OTHER INFORMATION: profiling primer

<400> SEQUENCE: 31
gaatgtttgc ggaagaatgc g                                              21

<210> SEQ ID NO 32
<211> LENGTH: 26
<212> TYPE: DNA
<213> ORGANISM: Artificial
<220> FEATURE:
<223> OTHER INFORMATION: profiling primer

<400> SEQUENCE: 32
aagaarcatg cdatatctar aaatat                                         26

<210> SEQ ID NO 33
<211> LENGTH: 21
<212> TYPE: DNA
<213> ORGANISM: Artificial
<220> FEATURE:
<223> OTHER INFORMATION: profiling primer

<400> SEQUENCE: 33
yttsarsgct aaaggragrc c                                              21

<210> SEQ ID NO 34
<211> LENGTH: 22
<212> TYPE: DNA
<213> ORGANISM: Artificial
<220> FEATURE:
<223> OTHER INFORMATION: profiling primer

<400> SEQUENCE: 34
ctttagcbyt saarktgtkk gg                                             22

<210> SEQ ID NO 35
<211> LENGTH: 26
<212> TYPE: DNA
<213> ORGANISM: Artificial
<220> FEATURE:
<223> OTHER INFORMATION: profiling primer

<400> SEQUENCE: 35
atgcatgayt tratwvaaga batggg                                         26

<210> SEQ ID NO 36
<211> LENGTH: 21
<212> TYPE: DNA
<213> ORGANISM: Artificial
<220> FEATURE:
<223> OTHER INFORMATION: profiling primer
<220> FEATURE:
<221> NAME/KEY: misc_feature
<222> LOCATION: (15)..(15)
<223> OTHER INFORMATION: n is a, c, g, or t

<400> SEQUENCE: 36
tatgctacrt cdagntggtg c                                              21
```

<210> SEQ ID NO 37
<211> LENGTH: 20
<212> TYPE: DNA
<213> ORGANISM: Artificial
<220> FEATURE:
<223> OTHER INFORMATION: profiling primer
<220> FEATURE:
<221> NAME/KEY: misc_feature
<222> LOCATION: (1)..(1)
<223> OTHER INFORMATION: n is a, c, g, or t

<400> SEQUENCE: 37
ntagtraaga yatggaatgc                                              20

<210> SEQ ID NO 38
<211> LENGTH: 21
<212> TYPE: DNA
<213> ORGANISM: Artificial
<220> FEATURE:
<223> OTHER INFORMATION: profiling primer

<400> SEQUENCE: 38
ygatggtgga accahcttgg g                                            21

<210> SEQ ID NO 39
<211> LENGTH: 23
<212> TYPE: DNA
<213> ORGANISM: Artificial
<220> FEATURE:
<223> OTHER INFORMATION: profiling primer

<400> SEQUENCE: 39
cagagtaaca tacarcaaat ccc                                          23

<210> SEQ ID NO 40
<211> LENGTH: 2592
<212> TYPE: DNA
<213> ORGANISM: Solanum edinense Berthault
<220> FEATURE:
<221> NAME/KEY: CDS
<222> LOCATION: (1)..(2592)

<400> SEQUENCE: 40

```
atg gct gaa att ctt ctt aca gca gtc atc aat aaa tct gta gaa ata    48
Met Ala Glu Ile Leu Leu Thr Ala Val Ile Asn Lys Ser Val Glu Ile
1               5                   10                  15 gct gca aat gta ctc ttt caa caa ggg agc cgc ttg aat ttt ttg aaa    96
Ala Ala Asn Val Leu Phe Gln Gln Gly Ser Arg Leu Asn Phe Leu Lys
            20                  25                  30 gag gac atc gat tgg ctc cag aga gta ctg aga cac att cga tca tat   144
Glu Asp Ile Asp Trp Leu Gln Arg Val Leu Arg His Ile Arg Ser Tyr
        35                  40                  45 gta gac gat gca aag gcc aag gaa gtt gga ggc gat tca agg gtc aaa   192
Val Asp Asp Ala Lys Ala Lys Glu Val Gly Gly Asp Ser Arg Val Lys
    50                  55                  60 aac tta tta aaa gat att caa gaa ttg gca ggt gat gtg gag gat ctc   240
Asn Leu Leu Lys Asp Ile Gln Glu Leu Ala Gly Asp Val Glu Asp Leu
65                  70                  75                  80 tta gat gag ttt ctt cca aaa atc caa caa tcc agt aag ttc aaa ggc   288
Leu Asp Glu Phe Leu Pro Lys Ile Gln Gln Ser Ser Lys Phe Lys Gly
                85                  90                  95 gca att tgt tgc ctt aag acg gtt tct ttt gcc gat gag ttt gct gtg   336
Ala Ile Cys Cys Leu Lys Thr Val Ser Phe Ala Asp Glu Phe Ala Val
            100                 105                 110
```

```
gag att gag aag ata aga aga agg gtt gct gac att gat agt tta agg      384
Glu Ile Glu Lys Ile Arg Arg Arg Val Ala Asp Ile Asp Ser Leu Arg
            115                 120                 125 aca act ttc aac atc aca gat aca agt aac aac aat aat gat tgc att      432
Thr Thr Phe Asn Ile Thr Asp Thr Ser Asn Asn Asn Asn Asp Cys Ile
    130                 135                 140 cca atg gaa cag aga aga aaa ttc ctt cat gct gat gaa aca gag gtc      480
Pro Met Glu Gln Arg Arg Lys Phe Leu His Ala Asp Glu Thr Glu Val
145                 150                 155                 160 atc ggt ttg gat gat gac ttc aac aag ctc caa gac aaa ttg ctt gtt      528
Ile Gly Leu Asp Asp Asp Phe Asn Lys Leu Gln Asp Lys Leu Leu Val
                165                 170                 175 caa gat ttg tgt aat gga gtt gtt tca ata gtt ggc atg cct ggt cta      576
Gln Asp Leu Cys Asn Gly Val Val Ser Ile Val Gly Met Pro Gly Leu
            180                 185                 190 gga aaa aca act ctt gcc aag aaa ctt tat agg cat gtc cgt cat caa      624
Gly Lys Thr Thr Leu Ala Lys Lys Leu Tyr Arg His Val Arg His Gln
    195                 200                 205 ttt gag tgt tct gca ctg gtc tac gtt tca caa cag cca aga gca gga      672
Phe Glu Cys Ser Ala Leu Val Tyr Val Ser Gln Gln Pro Arg Ala Gly
210                 215                 220 gaa atc tta ctt gac ata gcc aag caa gtt gga ctg acg gac gag gga      720
Glu Ile Leu Leu Asp Ile Ala Lys Gln Val Gly Leu Thr Asp Glu Gly
225                 230                 235                 240 agg aaa gaa cac ttg gag gac aat cta aga tca ctt ttg gaa aca aaa      768
Arg Lys Glu His Leu Glu Asp Asn Leu Arg Ser Leu Leu Glu Thr Lys
                245                 250                 255 agg tat gtt att ctc tta gat gac att tgg gat act aaa atc tgg gat      816
Arg Tyr Val Ile Leu Leu Asp Asp Ile Trp Asp Thr Lys Ile Trp Asp
            260                 265                 270 gct ctg aac cgt gtc ctt cgt cct gaa tgt gat tca aaa att ggc agt      864
Ala Leu Asn Arg Val Leu Arg Pro Glu Cys Asp Ser Lys Ile Gly Ser
    275                 280                 285 agg ata att atc act tct cga tat cat cat gta ggc aga tac ata gga      912
Arg Ile Ile Ile Thr Ser Arg Tyr His His Val Gly Arg Tyr Ile Gly
290                 295                 300 gag gat ttc tcg ctc cac gag ttg caa ccc tta gat tca gag aaa agt      960
Glu Asp Phe Ser Leu His Glu Leu Gln Pro Leu Asp Ser Glu Lys Ser
305                 310                 315                 320 ttt gaa ctc ttt acc aag aaa atc ttt att ttt gat aat aat aat aat     1008
Phe Glu Leu Phe Thr Lys Lys Ile Phe Ile Phe Asp Asn Asn Asn Asn
                325                 330                 335 tgg gct aat gct tca cct gtc ttg gta gat att ggt aaa agt ata gtt     1056
Trp Ala Asn Ala Ser Pro Val Leu Val Asp Ile Gly Lys Ser Ile Val
            340                 345                 350 cgg aga tgt gga ggt att cca tta gcc att gtg gtg acg gca ggc atg     1104
Arg Arg Cys Gly Gly Ile Pro Leu Ala Ile Val Val Thr Ala Gly Met
    355                 360                 365 tta agg gca aga gaa aga acg gaa cat gca tgg aat aga gtg ctt gag     1152
Leu Arg Ala Arg Glu Arg Thr Glu His Ala Trp Asn Arg Val Leu Glu
370                 375                 380 cgt ata ggt cat aat att cag gat gga tgt gct aag gca ttg gct ctg     1200
Arg Ile Gly His Asn Ile Gln Asp Gly Cys Ala Lys Ala Leu Ala Leu
385                 390                 395                 400 agt tac aat gat ttg ccc att gca tta agg cca tgt ttc ttg tac ttt     1248
Ser Tyr Asn Asp Leu Pro Ile Ala Leu Arg Pro Cys Phe Leu Tyr Phe
                405                 410                 415 ggt ctt tac ccc gag gac cat gaa att cgt gct ttt gat ttg aca aat     1296
Gly Leu Tyr Pro Glu Asp His Glu Ile Arg Ala Phe Asp Leu Thr Asn
            420                 425                 430
```

```
atg tgg att gct gag aag ctg ata gtt gta aat agt ggc aat agg cga      1344
Met Trp Ile Ala Glu Lys Leu Ile Val Val Asn Ser Gly Asn Arg Arg
        435                 440                 445 gag gct gaa agt ttg gcg gat gat gtc cta aat gat ttg gtt tca aga      1392
Glu Ala Glu Ser Leu Ala Asp Asp Val Leu Asn Asp Leu Val Ser Arg
450                 455                 460 aac ttg att caa gtt gcc aag agg aca tat gat gga gga att tca agt      1440
Asn Leu Ile Gln Val Ala Lys Arg Thr Tyr Asp Gly Gly Ile Ser Ser
465                 470                 475                 480 tgt cgc ata cat gac ttg tta cat agt ttg tgt gtt gac ttg gct aag      1488
Cys Arg Ile His Asp Leu Leu His Ser Leu Cys Val Asp Leu Ala Lys
                485                 490                 495 gaa agc aac ttc ttt cac acc gag cac aat gca ttt ggt gat ccc ggc      1536
Glu Ser Asn Phe Phe His Thr Glu His Asn Ala Phe Gly Asp Pro Gly
            500                 505                 510 aat gtt tct agg ctg cga agg att aca ttc tac tct gat aat aat gcc      1584
Asn Val Ser Arg Leu Arg Arg Ile Thr Phe Tyr Ser Asp Asn Asn Ala
        515                 520                 525 atg aat gag ttc ttc cgt tca aat cct aag ctt gag aag ctt cgt gca      1632
Met Asn Glu Phe Phe Arg Ser Asn Pro Lys Leu Glu Lys Leu Arg Ala
530                 535                 540 ctt ttc tgt ttc aca aaa gga gac tct tgc ata ttt tct cat ttg gct      1680
Leu Phe Cys Phe Thr Lys Gly Asp Ser Cys Ile Phe Ser His Leu Ala
545                 550                 555                 560 cat cat gac ttc aaa tta tta caa gtg ttg gtt gta gtc cag cct cga      1728
His His Asp Phe Lys Leu Leu Gln Val Leu Val Val Val Gln Pro Arg
                565                 570                 575 aaa aat tat gat ttc agc att agc caa atc aaa att ggg aac atg agt      1776
Lys Asn Tyr Asp Phe Ser Ile Ser Gln Ile Lys Ile Gly Asn Met Ser
            580                 585                 590 tgc tta cgc tat ctg cga ttc gag ggg gat att tat ggg gaa ctg cca      1824
Cys Leu Arg Tyr Leu Arg Phe Glu Gly Asp Ile Tyr Gly Glu Leu Pro
        595                 600                 605 aat tgt atg gtg aag ctc aaa cac tta gag acc cta gat att agt aaa      1872
Asn Cys Met Val Lys Leu Lys His Leu Glu Thr Leu Asp Ile Ser Lys
610                 615                 620 agc ttc att att aaa ctt cct act ggt gtt tgg aag act aca caa ttg      1920
Ser Phe Ile Ile Lys Leu Pro Thr Gly Val Trp Lys Thr Thr Gln Leu
625                 630                 635                 640 aga cat ctt cgt tct aat ggt tat aat cta gca cct tac agt tac ttt      1968
Arg His Leu Arg Ser Asn Gly Tyr Asn Leu Ala Pro Tyr Ser Tyr Phe
                645                 650                 655 tgt ata agc cca ttt ttt cca aac gtg cct cct aat aat gta caa act      2016
Cys Ile Ser Pro Phe Phe Pro Asn Val Pro Pro Asn Asn Val Gln Thr
            660                 665                 670 ttg atg tgg atg gat ggt gaa ttt ttt gaa ccg aga tgg ttg cac cga      2064
Leu Met Trp Met Asp Gly Glu Phe Phe Glu Pro Arg Trp Leu His Arg
        675                 680                 685 ttt atc aat tta aga aaa ctg ggt tta cag gaa gta tcc gat tct acc      2112
Phe Ile Asn Leu Arg Lys Leu Gly Leu Gln Glu Val Ser Asp Ser Thr
690                 695                 700 att aag aaa tta tca aca ttg agc cct gtg cca acg aca ctg gag gtt      2160
Ile Lys Lys Leu Ser Thr Leu Ser Pro Val Pro Thr Thr Leu Glu Val
705                 710                 715                 720 cta aag ctc agc tca ttt ttc agt gaa ttg aga gag caa ata aac ttg      2208
Leu Lys Leu Ser Ser Phe Phe Ser Glu Leu Arg Glu Gln Ile Asn Leu
                725                 730                 735 tcg tcg tat cca aat att gtt aag ttg cat ttg aac gga aga att ccc      2256
Ser Ser Tyr Pro Asn Ile Val Lys Leu His Leu Asn Gly Arg Ile Pro
            740                 745                 750
```

```
ttg aac gtc tct gaa tca ttc cct cca aat ctt gtc aag ctt act ctt      2304
Leu Asn Val Ser Glu Ser Phe Pro Pro Asn Leu Val Lys Leu Thr Leu
        755                 760                 765 tgc aac ttg atg gta gac ggt cat gta gtg gca gtg ctt aag aaa tta      2352
Cys Asn Leu Met Val Asp Gly His Val Val Ala Val Leu Lys Lys Leu
770                 775                 780 ccc aaa tta aag ata ctt aca ttg cat agg tgc aga cat gat gca gaa      2400
Pro Lys Leu Lys Ile Leu Thr Leu His Arg Cys Arg His Asp Ala Glu
785                 790                 795                 800 aaa atg gat ctc tct ggt gat ggt gat agc ttt ccg caa ctt gaa gtt      2448
Lys Met Asp Leu Ser Gly Asp Gly Asp Ser Phe Pro Gln Leu Glu Val
                805                 810                 815 ttg cat att aaa gat cca gtc tgc ttg tct gaa gta acg tgc acg gat      2496
Leu His Ile Lys Asp Pro Val Cys Leu Ser Glu Val Thr Cys Thr Asp
                820                 825                 830 gat gtc ggt atg cct aaa ttg aaa aag tta tta ctt ata gaa aga act      2544
Asp Val Gly Met Pro Lys Leu Lys Lys Leu Leu Leu Ile Glu Arg Thr
            835                 840                 845 gat tcc aac gtt agg ctc tcg gaa aga ctt gca aaa ctg aga gta tga      2592
Asp Ser Asn Val Arg Leu Ser Glu Arg Leu Ala Lys Leu Arg Val
850                 855                 860

<210> SEQ ID NO 41
<211> LENGTH: 863
<212> TYPE: PRT
<213> ORGANISM: Solanum edinense Berthault

<400> SEQUENCE: 41

Met Ala Glu Ile Leu Leu Thr Ala Val Ile Asn Lys Ser Val Glu Ile
1               5                   10                  15

Ala Ala Asn Val Leu Phe Gln Gln Gly Ser Arg Leu Asn Phe Leu Lys
            20                  25                  30

Glu Asp Ile Asp Trp Leu Gln Arg Val Leu Arg His Ile Arg Ser Tyr
        35                  40                  45

Val Asp Asp Ala Lys Ala Lys Glu Val Gly Gly Asp Ser Arg Val Lys
    50                  55                  60

Asn Leu Leu Lys Asp Ile Gln Glu Leu Ala Gly Asp Val Glu Asp Leu
65                  70                  75                  80

Leu Asp Glu Phe Leu Pro Lys Ile Gln Gln Ser Ser Lys Phe Lys Gly
                85                  90                  95

Ala Ile Cys Cys Leu Lys Thr Val Ser Phe Ala Asp Glu Phe Ala Val
            100                 105                 110

Glu Ile Glu Lys Ile Arg Arg Arg Val Ala Asp Ile Asp Ser Leu Arg
        115                 120                 125

Thr Thr Phe Asn Ile Thr Asp Thr Ser Asn Asn Asn Asp Cys Ile
    130                 135                 140

Pro Met Glu Gln Arg Arg Lys Phe Leu His Ala Asp Glu Thr Glu Val
145                 150                 155                 160

Ile Gly Leu Asp Asp Asp Phe Asn Lys Leu Gln Asp Lys Leu Leu Val
                165                 170                 175

Gln Asp Leu Cys Asn Gly Val Ser Ile Val Gly Met Pro Gly Leu
            180                 185                 190

Gly Lys Thr Thr Leu Ala Lys Lys Leu Tyr Arg His Val Arg His Gln
        195                 200                 205

Phe Glu Cys Ser Ala Leu Val Tyr Val Ser Gln Gln Pro Arg Ala Gly
    210                 215                 220
```

```
Glu Ile Leu Leu Asp Ile Ala Lys Gln Val Gly Leu Thr Asp Glu Gly
225                 230                 235                 240

Arg Lys Glu His Leu Glu Asp Asn Leu Arg Ser Leu Leu Glu Thr Lys
            245                 250                 255

Arg Tyr Val Ile Leu Leu Asp Asp Ile Trp Asp Thr Lys Ile Trp Asp
            260                 265                 270

Ala Leu Asn Arg Val Leu Arg Pro Glu Cys Asp Ser Lys Ile Gly Ser
            275                 280                 285

Arg Ile Ile Ile Thr Ser Arg Tyr His His Val Gly Arg Tyr Ile Gly
290                 295                 300

Glu Asp Phe Ser Leu His Glu Leu Gln Pro Leu Asp Ser Glu Lys Ser
305                 310                 315                 320

Phe Glu Leu Phe Thr Lys Lys Ile Phe Ile Phe Asp Asn Asn Asn Asn
                325                 330                 335

Trp Ala Asn Ala Ser Pro Val Leu Val Asp Ile Gly Lys Ser Ile Val
            340                 345                 350

Arg Arg Cys Gly Gly Ile Pro Leu Ala Ile Val Val Thr Ala Gly Met
            355                 360                 365

Leu Arg Ala Arg Glu Arg Thr Glu His Ala Trp Asn Arg Val Leu Glu
370                 375                 380

Arg Ile Gly His Asn Ile Gln Asp Gly Cys Ala Lys Ala Leu Ala Leu
385                 390                 395                 400

Ser Tyr Asn Asp Leu Pro Ile Ala Leu Arg Pro Cys Phe Leu Tyr Phe
                405                 410                 415

Gly Leu Tyr Pro Glu Asp His Glu Ile Arg Ala Phe Asp Leu Thr Asn
            420                 425                 430

Met Trp Ile Ala Glu Lys Leu Ile Val Val Asn Ser Gly Asn Arg Arg
            435                 440                 445

Glu Ala Glu Ser Leu Ala Asp Asp Val Leu Asn Asp Leu Val Ser Arg
450                 455                 460

Asn Leu Ile Gln Val Ala Lys Arg Thr Tyr Asp Gly Gly Ile Ser Ser
465                 470                 475                 480

Cys Arg Ile His Asp Leu Leu His Ser Leu Cys Val Asp Leu Ala Lys
                485                 490                 495

Glu Ser Asn Phe Phe His Thr Glu His Asn Ala Phe Gly Asp Pro Gly
            500                 505                 510

Asn Val Ser Arg Leu Arg Arg Ile Thr Phe Tyr Ser Asn Asn Ala
            515                 520                 525

Met Asn Glu Phe Phe Arg Ser Asn Pro Lys Leu Glu Lys Leu Arg Ala
530                 535                 540

Leu Phe Cys Phe Thr Lys Gly Asp Ser Cys Ile Phe Ser His Leu Ala
545                 550                 555                 560

His His Asp Phe Lys Leu Leu Gln Val Leu Val Val Gln Pro Arg
                565                 570                 575

Lys Asn Tyr Asp Phe Ser Ile Ser Gln Ile Lys Ile Gly Asn Met Ser
            580                 585                 590

Cys Leu Arg Tyr Leu Arg Phe Glu Gly Asp Ile Tyr Gly Glu Leu Pro
            595                 600                 605

Asn Cys Met Val Lys Leu Lys His Leu Glu Thr Leu Asp Ile Ser Lys
            610                 615                 620

Ser Phe Ile Ile Lys Leu Pro Thr Gly Val Trp Lys Thr Gln Leu
625                 630                 635                 640
```

```
Arg His Leu Arg Ser Asn Gly Tyr Asn Leu Ala Pro Tyr Ser Tyr Phe
                645                 650                 655

Cys Ile Ser Pro Phe Pro Asn Val Pro Asn Asn Val Gln Thr
            660                 665                 670

Leu Met Trp Met Asp Gly Glu Phe Phe Glu Pro Arg Trp Leu His Arg
        675                 680                 685

Phe Ile Asn Leu Arg Lys Leu Gly Leu Gln Glu Val Ser Asp Ser Thr
    690                 695                 700

Ile Lys Lys Leu Ser Thr Leu Ser Pro Val Pro Thr Thr Leu Glu Val
705                 710                 715                 720

Leu Lys Leu Ser Ser Phe Phe Ser Glu Leu Arg Glu Gln Ile Asn Leu
                725                 730                 735

Ser Ser Tyr Pro Asn Ile Val Lys Leu His Leu Asn Gly Arg Ile Pro
            740                 745                 750

Leu Asn Val Ser Glu Ser Phe Pro Pro Asn Leu Val Lys Leu Thr Leu
        755                 760                 765

Cys Asn Leu Met Val Asp Gly His Val Val Ala Val Leu Lys Lys Leu
    770                 775                 780

Pro Lys Leu Lys Ile Leu Thr Leu His Arg Cys Arg His Asp Ala Glu
785                 790                 795                 800

Lys Met Asp Leu Ser Gly Asp Gly Asp Ser Phe Pro Gln Leu Glu Val
                805                 810                 815

Leu His Ile Lys Asp Pro Val Cys Leu Ser Glu Val Thr Cys Thr Asp
            820                 825                 830

Asp Val Gly Met Pro Lys Leu Lys Lys Leu Leu Leu Ile Glu Arg Thr
        835                 840                 845

Asp Ser Asn Val Arg Leu Ser Glu Arg Leu Ala Lys Leu Arg Val
    850                 855                 860

<210> SEQ ID NO 42
<211> LENGTH: 891
<212> TYPE: PRT
<213> ORGANISM: Solanum venturii

<400> SEQUENCE: 42

Met Asn Tyr Cys Val Tyr Lys Thr Trp Ala Val Asp Ser Tyr Phe Pro
1               5                   10                  15

Phe Leu Ile Leu Thr Phe Arg Lys Lys Lys Phe Asn Glu Lys Leu Lys
            20                  25                  30

Glu Met Ala Glu Ile Leu Leu Thr Ala Val Ile Asn Lys Ser Ile Glu
        35                  40                  45

Ile Ala Gly Asn Val Leu Phe Gln Glu Gly Thr Arg Leu Tyr Trp Leu
    50                  55                  60

Lys Glu Asp Ile Asp Trp Leu Gln Arg Glu Met Arg His Ile Arg Ser
65                  70                  75                  80

Tyr Val Asp Asn Ala Lys Ala Lys Glu Val Gly Gly Asp Ser Arg Val
                85                  90                  95

Lys Asn Leu Leu Lys Asp Ile Gln Gln Leu Ala Gly Asp Val Glu Asp
            100                 105                 110

Leu Leu Asp Glu Phe Leu Pro Lys Ile Gln Gln Ser Asn Lys Phe Ile
        115                 120                 125

Cys Cys Leu Lys Thr Val Ser Phe Ala Asp Glu Phe Ala Met Glu Ile
    130                 135                 140

Glu Lys Ile Lys Arg Arg Val Ala Asp Ile Asp Arg Val Arg Thr Thr
145                 150                 155                 160
```

-continued

```
Tyr Ser Ile Thr Asp Thr Ser Asn Asn Asn Asp Asp Cys Ile Pro Leu
            165                 170                 175
Asp Arg Arg Leu Phe Leu His Ala Asp Glu Thr Glu Val Ile Gly
        180                 185                 190
Leu Glu Asp Asp Phe Asn Thr Leu Gln Ala Lys Leu Leu Asp His Asp
        195                 200                 205
Leu Pro Tyr Gly Val Val Ser Ile Val Gly Met Pro Gly Leu Gly Lys
        210                 215                 220
Thr Thr Leu Ala Lys Lys Leu Tyr Arg His Val Cys His Gln Phe Glu
225                 230                 235                 240
Cys Ser Gly Leu Val Tyr Val Ser Gln Gln Pro Arg Ala Gly Glu Ile
                245                 250                 255
Leu His Asp Ile Ala Lys Gln Val Gly Leu Thr Glu Glu Arg Lys
        260                 265                 270
Glu Asn Leu Glu Asn Asn Leu Arg Ser Leu Leu Lys Ile Lys Arg Tyr
        275                 280                 285
Val Ile Leu Leu Asp Asp Ile Trp Asp Val Glu Ile Trp Asp Asp Leu
        290                 295                 300
Lys Leu Val Leu Pro Glu Cys Asp Ser Lys Ile Gly Ser Arg Ile Ile
305                 310                 315                 320
Ile Thr Ser Arg Asn Ser Asn Val Gly Arg Tyr Ile Gly Gly Asp Phe
                325                 330                 335
Ser Ile His Val Leu Gln Pro Leu Asp Ser Glu Lys Ser Phe Glu Leu
            340                 345                 350
Phe Thr Lys Lys Ile Phe Asn Phe Val Asn Asp Asn Trp Ala Asn Ala
        355                 360                 365
Ser Pro Asp Leu Val Asn Ile Gly Arg Cys Ile Val Glu Arg Cys Gly
        370                 375                 380
Gly Ile Pro Leu Ala Ile Val Val Thr Ala Gly Met Leu Arg Ala Arg
385                 390                 395                 400
Gly Arg Thr Glu His Ala Trp Asn Arg Val Leu Glu Ser Met Ala His
                405                 410                 415
Lys Ile Gln Asp Gly Cys Gly Lys Val Leu Ala Leu Ser Tyr Asn Asp
            420                 425                 430
Leu Pro Ile Ala Leu Arg Pro Cys Phe Leu Tyr Phe Gly Leu Tyr Pro
        435                 440                 445
Glu Asp His Glu Ile Arg Ala Phe Asp Leu Thr Asn Met Trp Ile Ala
        450                 455                 460
Glu Lys Leu Ile Val Val Asn Thr Gly Asn Gly Arg Glu Ala Glu Ser
465                 470                 475                 480
Leu Ala Asp Asp Val Leu Asn Asp Leu Val Ser Arg Asn Leu Ile Gln
                485                 490                 495
Val Ala Lys Arg Thr Tyr Asp Gly Arg Ile Ser Ser Cys Arg Ile His
            500                 505                 510
Asp Leu Leu His Ser Leu Cys Val Asp Leu Ala Lys Glu Ser Asn Phe
        515                 520                 525
Phe His Thr Glu His Asn Ala Phe Gly Asp Pro Ser Asn Val Ala Arg
        530                 535                 540
Val Arg Arg Ile Thr Phe Tyr Ser Asp Asp Asn Ala Met Asn Glu Phe
545                 550                 555                 560
Phe His Leu Asn Pro Lys Pro Met Lys Leu Arg Ser Leu Phe Cys Phe
                565                 570                 575
```

```
Thr Lys Asp Arg Cys Ile Phe Ser Gln Met Ala His Leu Asn Phe Lys
            580                 585                 590

Leu Leu Gln Val Leu Val Val Met Ser Gln Lys Gly Tyr Gln His
        595                 600                 605

Val Thr Phe Pro Lys Lys Ile Gly Asn Met Ser Cys Leu Arg Tyr Val
    610                 615                 620

Arg Leu Glu Gly Ala Ile Arg Val Lys Leu Pro Asn Ser Ile Val Lys
625                 630                 635                 640

Leu Lys Cys Leu Glu Thr Leu Asp Ile Phe His Ser Ser Lys Leu
                645                 650                 655

Pro Phe Gly Val Trp Glu Ser Lys Ile Leu Arg His Leu Cys Tyr Thr
            660                 665                 670

Glu Glu Cys Tyr Cys Val Ser Phe Ala Ser Pro Phe Cys Arg Ile Met
        675                 680                 685

Pro Pro Asn Asn Leu Gln Thr Leu Met Trp Val Asp Asp Lys Phe Cys
    690                 695                 700

Glu Pro Arg Leu Leu His Arg Leu Ile Asn Leu Arg Thr Leu Cys Ile
705                 710                 715                 720

Met Asp Val Ser Gly Ser Thr Ile Lys Ile Leu Ser Ala Leu Ser Pro
                725                 730                 735

Val Pro Arg Ala Leu Glu Val Leu Lys Leu Arg Phe Phe Lys Asn Thr
            740                 745                 750

Ser Glu Gln Ile Asn Leu Ser Ser His Pro Asn Ile Val Glu Leu Gly
        755                 760                 765

Leu Val Gly Phe Ser Ala Met Leu Leu Asn Ile Glu Ala Phe Pro Pro
    770                 775                 780

Asn Leu Val Lys Leu Asn Leu Val Gly Leu Met Val Asp Gly His Leu
785                 790                 795                 800

Leu Ala Val Leu Lys Lys Leu Pro Lys Leu Arg Ile Leu Ile Leu Leu
                805                 810                 815

Trp Cys Arg His Asp Ala Glu Lys Met Asp Leu Ser Gly Asp Ser Phe
            820                 825                 830

Pro Gln Leu Glu Val Leu Tyr Ile Glu Asp Ala Gln Gly Leu Ser Glu
        835                 840                 845

Val Thr Cys Met Asp Asp Met Ser Met Pro Lys Leu Lys Lys Leu Phe
    850                 855                 860

Leu Val Gln Gly Pro Asn Ile Ser Pro Ile Ser Leu Arg Val Ser Glu
865                 870                 875                 880

Arg Leu Ala Lys Leu Arg Ile Ser Gln Val Leu
                885                 890

<210> SEQ ID NO 43
<211> LENGTH: 862
<212> TYPE: PRT
<213> ORGANISM: Solanum mochiquense

<400> SEQUENCE: 43

Met Ala Glu Ile Leu Leu Thr Ala Val Ile Asn Lys Ser Val Glu Ile
1               5                   10                  15

Ala Gly Asn Val Leu Phe Gln Glu Gly Thr Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Val Gly Gly Asp Ser Arg Val Lys
    50                  55                  60
```

```
Asn Leu Leu Lys Asp Ile Gln Gln Leu Ala Gly Asp Val Glu Asp Leu
 65                  70                  75                  80

Leu Asp Glu Phe Leu Pro Lys Ile Gln Gln Ser Ser Lys Phe Lys Gly
                 85                  90                  95

Ala Ile Cys Cys Leu Lys Thr Val Ser Phe Ala Asp Glu Phe Ala Met
            100                 105                 110

Glu Ile Glu Lys Ile Lys Arg Arg Val Val Asp Ile Asp Arg Val Arg
        115                 120                 125

Thr Thr Tyr Asn Ile Met Asp Thr Asn Asn Asn Asp Cys Ile Pro
130                 135                 140

Leu Asp Gln Arg Arg Leu Phe Leu His Val Asp Glu Thr Glu Val Ile
145                 150                 155                 160

Gly Leu Asp Asp Asp Phe Asn Thr Leu Gln Ala Lys Leu Leu Asp Gln
                165                 170                 175

Asp Leu Pro Tyr Gly Val Val Ser Ile Val Gly Met Pro Gly Leu Gly
            180                 185                 190

Lys Thr Thr Leu Ala Lys Lys Leu Tyr Arg His Val Arg His Lys Phe
        195                 200                 205

Glu Cys Ser Gly Leu Val Tyr Val Ser Gln Gln Pro Arg Ala Gly Glu
    210                 215                 220

Ile Leu Ile Asp Ile Ala Lys Gln Val Gly Leu Thr Glu Asp Glu Arg
225                 230                 235                 240

Lys Glu Asn Leu Glu Asn Asn Leu Arg Ser Leu Leu Lys Arg Lys Arg
                245                 250                 255

Tyr Val Ile Leu Leu Asp Asp Ile Trp Asp Val Glu Ile Trp Asp Asp
            260                 265                 270

Leu Lys Leu Val Leu Pro Glu Cys Asp Ser Lys Ile Gly Ser Arg Ile
        275                 280                 285

Ile Ile Thr Ser Arg Asn Ser Asn Val Gly Arg Tyr Ile Gly Gly Asp
    290                 295                 300

Phe Ser Ile His Val Leu Gln Pro Leu Asn Ser Glu Asn Ser Phe Glu
305                 310                 315                 320

Leu Phe Thr Lys Lys Ile Phe Ile Phe Asp Asn Asn Asn Asn Trp Thr
                325                 330                 335

Asn Ala Ser Pro Asn Leu Val Asp Ile Gly Arg Ser Ile Val Gly Arg
            340                 345                 350

Cys Gly Gly Ile Pro Leu Ala Ile Val Val Thr Ala Gly Met Leu Arg
        355                 360                 365

Ala Arg Glu Arg Thr Glu Arg Ala Trp Asn Arg Leu Leu Glu Ser Met
    370                 375                 380

Ser His Lys Val Gln Asp Gly Cys Ala Lys Val Leu Ala Leu Ser Tyr
385                 390                 395                 400

Asn Asp Leu Pro Ile Ala Leu Arg Pro Cys Phe Leu Tyr Phe Gly Leu
                405                 410                 415

Tyr Pro Glu Asp His Glu Ile Arg Ala Phe Asp Leu Thr Asn Met Trp
            420                 425                 430

Ile Ala Glu Lys Leu Ile Val Val Asn Ser Gly Asn Gly Arg Glu Ala
        435                 440                 445

Glu Ser Leu Ala Asp Asp Val Leu Asn Asp Leu Val Ser Arg Asn Met
    450                 455                 460

Ile Gln Val Ala Lys Arg Thr Tyr Asp Gly Arg Ile Ser Ser Cys Arg
465                 470                 475                 480
```

```
Ile His Asp Leu Leu His Ser Leu Cys Val Asp Leu Ala Lys Glu Ser
            485                 490                 495

Asn Phe Phe His Thr Glu His Asn Ala Leu Gly Asp Pro Gly Asn Val
        500                 505                 510

Ala Arg Leu Arg Arg Ile Thr Phe Tyr Ser Asp Asn Asn Ala Met Asn
        515                 520                 525

Glu Phe Phe Arg Ser Asn Pro Lys Leu Glu Lys Leu Arg Ala Leu Phe
        530                 535                 540

Cys Phe Thr Glu Asp Pro Cys Ile Phe Ser Gln Leu Ala His Leu Asp
545                 550                 555                 560

Phe Lys Leu Leu Gln Val Leu Val Val Ile Phe Val Asp Asp Ile
            565                 570                 575

Cys Gly Val Ser Ile Pro Asn Thr Phe Gly Asn Met Arg Cys Leu Arg
            580                 585                 590

Tyr Leu Arg Phe Gln Gly His Phe Tyr Gly Lys Leu Pro Asn Cys Met
            595                 600                 605

Val Lys Leu Lys Arg Leu Glu Thr Leu Asp Ile Gly Tyr Ser Leu Ile
            610                 615                 620

Lys Phe Pro Thr Gly Val Trp Lys Ser Thr Gln Leu Lys His Leu Arg
625                 630                 635                 640

Tyr Gly Gly Phe Asn Gln Ala Ser Asn Ser Cys Phe Ser Ile Ser Pro
                645                 650                 655

Phe Phe Pro Asn Leu Tyr Ser Leu Pro His Asn Asn Val Gln Thr Leu
                660                 665                 670

Met Trp Leu Asp Asp Lys Phe Phe Glu Ala Gly Leu Leu His Arg Leu
            675                 680                 685

Ile Asn Leu Arg Lys Leu Gly Ile Ala Gly Val Ser Asp Ser Thr Val
            690                 695                 700

Lys Ile Leu Ser Ala Leu Ser Pro Val Pro Thr Ala Leu Glu Val Leu
705                 710                 715                 720

Lys Leu Lys Ile Tyr Arg Asp Met Ser Glu Gln Ile Asn Leu Ser Ser
                725                 730                 735

Tyr Pro Asn Ile Val Lys Leu Arg Leu Asn Val Cys Gly Arg Met Arg
                740                 745                 750

Leu Asn Cys Glu Ala Phe Pro Pro Asn Leu Val Lys Leu Thr Leu Val
            755                 760                 765

Gly Asp Glu Val Asp Gly His Val Ala Glu Leu Lys Lys Leu Pro
            770                 775                 780

Lys Leu Arg Ile Leu Lys Met Phe Gly Cys Ser His Asn Glu Glu Lys
785                 790                 795                 800

Met Asp Leu Ser Gly Asp Gly Ser Phe Pro Gln Leu Glu Val Leu
                805                 810                 815

His Ile Asp Glu Pro Asp Gly Leu Ser Glu Val Thr Cys Arg Asp Asp
                820                 825                 830

Val Ser Met Pro Lys Leu Lys Lys Leu Leu Val Gln Arg Arg Pro
            835                 840                 845

Ser Pro Ile Ser Leu Ser Glu Arg Leu Ala Lys Leu Arg Ile
        850                 855                 860

<210> SEQ ID NO 44
<211> LENGTH: 856
<212> TYPE: PRT
<213> ORGANISM: Solanum mochiquense
```

<400> SEQUENCE: 44

```
Met Ala Glu Ile Leu Leu Thr Thr Val Ile Asn Lys Ser Val Gly Ile
1               5                   10                  15

Ala Ala Asn Val Leu Phe Gln Glu Gly Thr Arg Leu Tyr Trp Leu Lys
            20                  25                  30

Glu Asp Ile Asp Trp Leu His Arg Glu Met Arg His Ile Arg Ser Tyr
        35                  40                  45

Val Asp Asp Ala Lys Ala Lys Glu Val Gly Gly Asp Ser Arg Val Arg
    50                  55                  60

Asn Leu Leu Lys Asp Ile Gln Gln Leu Ala Gly Asp Val Glu Asp Leu
65                  70                  75                  80

Leu Asp Glu Phe Leu Pro Lys Ile Gln Gln Ser Asn Lys Phe Ile Cys
                85                  90                  95

Cys Leu Lys Thr Val Ser Phe Ala Asp Glu Phe Ala Met Glu Ile Glu
            100                 105                 110

Lys Ile Lys Arg Arg Val Ala Asp Ile Thr Arg Val Arg Thr Thr Tyr
        115                 120                 125

Asn Ile Thr Asp Thr Ser Asn Asn Asp Asp Cys Ile Pro Leu Asp
    130                 135                 140

Arg Arg Arg Leu Phe Leu His Ala Asp Glu Thr Glu Val Ile Gly Leu
145                 150                 155                 160

Glu Asp Asp Phe Asn Thr Leu Lys Ala Lys Leu Leu Asp Gln Asp Leu
                165                 170                 175

Pro Tyr Gly Val Val Ser Ile Val Gly Met Pro Gly Leu Gly Lys Thr
            180                 185                 190

Thr Leu Ala Lys Lys Leu Tyr Arg His Val Arg Asp Gln Phe Glu Ser
        195                 200                 205

Ser Gly Leu Val Tyr Val Ser Gln Gln Pro Arg Ala Gly Glu Ile Leu
    210                 215                 220

Arg Asp Ile Ala Lys Gln Val Gly Leu Pro Lys Glu Glu Arg Lys Glu
225                 230                 235                 240

Asn Leu Glu Gly Asn Leu Arg Ser Leu Leu Lys Thr Lys Arg Tyr Val
                245                 250                 255

Ile Leu Leu Asp Asp Ile Trp Asp Val Glu Ile Trp Asp Asp Leu Lys
            260                 265                 270

Leu Val Leu Pro Glu Cys Asp Ser Glu Ile Gly Ser Arg Ile Ile Ile
        275                 280                 285

Thr Ser Arg Asn Ser Asn Val Gly Arg Tyr Ile Gly Gly Asp Phe Ser
    290                 295                 300

Ile His Met Leu Gln Pro Leu Asp Ser Glu Asn Ser Phe Glu Leu Phe
305                 310                 315                 320

Thr Lys Lys Ile Phe Thr Phe Asp Asn Asn Asn Trp Ala Asn Ala
                325                 330                 335

Ser Pro Asp Leu Val Asp Ile Gly Arg Ser Ile Val Gly Arg Cys Gly
            340                 345                 350

Gly Ile Pro Leu Ala Ile Val Val Thr Ala Gly Met Leu Arg Ala Arg
        355                 360                 365

Glu Arg Thr Glu His Ala Trp Asn Arg Val Leu Glu Ser Met Gly His
    370                 375                 380

Lys Val Gln Asp Gly Cys Ala Lys Val Leu Ala Leu Ser Tyr Asn Asp
385                 390                 395                 400

Leu Pro Ile Ala Leu Arg Pro Cys Phe Leu Tyr Leu Gly Leu Phe Pro
                405                 410                 415
```

```
Glu Asp His Glu Ile Arg Ala Phe Asp Leu Thr Asn Met Trp Ile Ala
            420                 425                 430

Glu Lys Leu Ile Val Val Asn Ser Gly Asn Gly Arg Glu Ala Glu Ser
        435                 440                 445

Leu Ala Glu Asp Val Leu Asn Asp Phe Val Ser Arg Asn Leu Ile Gln
    450                 455                 460

Val Ser Gln Arg Lys Cys Asn Gly Arg Ile Ser Ser Tyr Arg Ile His
465                 470                 475                 480

Asp Leu Leu His Ser Leu Cys Val Glu Leu Gly Lys Glu Ser Asn Phe
                485                 490                 495

Phe His Thr Glu His Asn Ala Phe Gly Asp Pro Asp Asn Val Ala Arg
            500                 505                 510

Val Arg Arg Ile Thr Phe Tyr Ser Asp Asn Asn Ala Met Ser Lys Phe
        515                 520                 525

Phe Arg Ser Asn Pro Lys Pro Lys Lys Leu Arg Ala Leu Phe Cys Phe
    530                 535                 540

Thr Asn Leu Asp Ser Cys Ile Phe Ser His Leu Ala His His Asp Phe
545                 550                 555                 560

Lys Leu Leu Gln Val Leu Val Val Ile Ser Tyr Asn Trp Leu Ser
                565                 570                 575

Val Ser Ile Ser Asn Lys Phe Gly Lys Met Ser Cys Leu Arg Tyr Leu
            580                 585                 590

Arg Leu Glu Gly Pro Ile Val Gly Glu Leu Ser Asn Ser Ile Val Lys
        595                 600                 605

Leu Lys Arg Val Glu Thr Ile Asp Ile Ala Gly Asp Asn Ile Lys Ile
    610                 615                 620

Pro Cys Gly Val Trp Glu Ser Lys Gln Leu Arg His Leu Arg Asn Arg
625                 630                 635                 640

Glu Glu Arg Arg Tyr Phe Phe Ser Val Ser Pro Phe Cys Leu Asn Met
                645                 650                 655

Tyr Pro Leu Pro Pro Asn Asn Leu Gln Thr Leu Val Trp Met Asp Asp
            660                 665                 670

Lys Phe Phe Glu Pro Arg Leu Leu His Arg Leu Ile Asn Leu Arg Lys
        675                 680                 685

Leu Gly Ile Trp Gly Thr Ser Asp Ser Thr Ile Lys Ile Leu Ser Ala
    690                 695                 700

Leu Ser Pro Val Pro Thr Ala Leu Glu Val Leu Lys Leu Tyr Phe Leu
705                 710                 715                 720

Arg Asp Leu Ser Glu Gln Ile Asn Leu Ser Thr Tyr Pro Asn Ile Val
                725                 730                 735

Lys Leu Asn Leu Gln Gly Phe Val Arg Val Arg Leu Asn Ser Glu Ala
            740                 745                 750

Phe Pro Pro Asn Leu Val Lys Leu Ile Leu Asp Lys Ile Glu Val Glu
        755                 760                 765

Gly His Val Val Ala Val Leu Lys Lys Leu Pro Thr Leu Arg Ile Leu
    770                 775                 780

Lys Met Tyr Gly Cys Lys His Asn Glu Glu Lys Met Asp Leu Ser Gly
785                 790                 795                 800

Asp Gly Asp Gly Asp Ser Phe Pro Gln Leu Glu Val Leu His Ile Glu
                805                 810                 815

Arg Pro Phe Phe Leu Phe Glu Ile Thr Cys Thr Asp Asp Ser Met
            820                 825                 830
```

```
Pro Lys Leu Lys Lys Leu Leu Thr Thr Ser Asn Val Arg Leu Ser
    835                 840                 845

Glu Arg Leu Ala Lys Leu Arg Val
    850                 855

<210> SEQ ID NO 45
<211> LENGTH: 861
<212> TYPE: PRT
<213> ORGANISM: Solanum lycopersicum

<400> SEQUENCE: 45

Met Ala Glu Ile Leu Leu Thr Ser Val Ile Asn Lys Ser Val Glu Ile
1               5                   10                  15

Ala Gly Asn Leu Leu Ile Gln Glu Gly Lys Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Ala Gly Gly Asp Ser Arg Val Lys
    50                  55                  60

Asn Leu Leu Lys Asp Ile Gln Glu Leu Ala Gly Asp Val Glu Asp Leu
65                  70                  75                  80

Leu Asp Asp Phe Leu Pro Lys Ile Gln Gln Ser Asn Lys Phe Asn Tyr
                85                  90                  95

Cys Leu Lys Arg Ser Ser Phe Ala Asp Glu Phe Ala Met Glu Ile Glu
            100                 105                 110

Lys Ile Lys Arg Arg Val Val Asp Ile Asp Arg Ile Arg Lys Thr Tyr
        115                 120                 125

Asn Ile Ile Asp Thr Asp Asn Asn Asp Asp Cys Val Leu Leu Asp
    130                 135                 140

Arg Arg Arg Leu Phe Leu His Ala Asp Glu Thr Glu Ile Ile Gly Leu
145                 150                 155                 160

Asp Asp Asp Phe Asn Met Leu Gln Ala Lys Leu Leu Asn Gln Asp Leu
                165                 170                 175

His Tyr Gly Val Val Ser Ile Val Gly Met Pro Gly Leu Gly Lys Thr
            180                 185                 190

Thr Leu Ala Lys Lys Leu Tyr Arg Leu Ile Arg Asp Gln Phe Glu Cys
        195                 200                 205

Ser Gly Leu Val Tyr Val Ser Gln Gln Pro Arg Ala Ser Glu Ile Leu
    210                 215                 220

Leu Asp Ile Ala Lys Gln Ile Gly Leu Thr Glu Gln Lys Met Lys Glu
225                 230                 235                 240

Asn Leu Glu Asp Asn Leu Arg Ser Leu Leu Lys Ile Lys Arg Tyr Val
                245                 250                 255

Ile Leu Leu Asp Asp Ile Trp Asp Val Glu Ile Trp Asp Asp Leu Lys
            260                 265                 270

Leu Val Leu Pro Glu Cys Asp Ser Lys Val Gly Ser Arg Met Ile Ile
        275                 280                 285

Thr Ser Arg Asn Ser Asn Val Gly Arg Tyr Ile Gly Gly Glu Ser Ser
    290                 295                 300

Leu His Ala Leu Gln Pro Leu Glu Ser Glu Lys Ser Phe Glu Leu Phe
305                 310                 315                 320

Thr Lys Lys Ile Phe Asn Phe Asp Asp Asn Ser Trp Ala Asn Ala
                325                 330                 335

Ser Pro Asp Leu Val Asn Ile Gly Arg Asn Ile Val Gly Arg Cys Gly
            340                 345                 350
```

-continued

Gly Ile Pro Leu Ala Ile Val Val Thr Ala Gly Met Leu Arg Ala Arg
            355                 360                 365
Glu Arg Thr Glu His Ala Trp Asn Arg Val Leu Glu Ser Met Gly His
370                 375                 380
Lys Val Gln Asp Gly Cys Ala Lys Val Leu Ala Leu Ser Tyr Asn Asp
385                 390                 395                 400
Leu Pro Ile Ala Ser Arg Pro Cys Phe Leu Tyr Phe Gly Leu Tyr Pro
                405                 410                 415
Glu Asp His Glu Ile Arg Ala Phe Asp Leu Ile Asn Met Trp Ile Ala
            420                 425                 430
Glu Lys Phe Ile Val Val Asn Ser Gly Asn Arg Arg Glu Ala Glu Asp
        435                 440                 445
Leu Ala Glu Asp Val Leu Asn Asp Leu Val Ser Arg Asn Leu Ile Gln
    450                 455                 460
Leu Ala Lys Arg Thr Tyr Asn Gly Arg Ile Ser Ser Cys Arg Ile His
465                 470                 475                 480
Asp Leu Leu His Ser Leu Cys Val Asp Leu Ala Lys Glu Ser Asn Phe
                485                 490                 495
Phe His Thr Ala His Asp Ala Phe Gly Asp Pro Gly Asn Val Ala Arg
            500                 505                 510
Leu Arg Arg Ile Thr Phe Tyr Ser Asp Asn Val Met Ile Glu Phe Phe
        515                 520                 525
Arg Ser Asn Pro Lys Leu Glu Lys Leu Arg Val Leu Phe Cys Phe Ala
    530                 535                 540
Lys Asp Pro Ser Ile Phe Ser His Met Ala Tyr Phe Asp Phe Lys Leu
545                 550                 555                 560
Leu His Thr Leu Val Val Met Ser Gln Ser Phe Gln Ala Tyr Val
                565                 570                 575
Thr Ile Pro Ser Lys Phe Gly Asn Met Thr Cys Leu Arg Tyr Leu Arg
            580                 585                 590
Leu Glu Gly Asn Ile Cys Gly Lys Leu Pro Asn Ser Ile Val Lys Leu
        595                 600                 605
Thr Arg Leu Glu Thr Ile Asp Ile Asp Arg Arg Ser Leu Ile Gln Pro
    610                 615                 620
Pro Ser Gly Val Trp Glu Ser Lys His Leu Arg His Leu Cys Tyr Arg
625                 630                 635                 640
Asp Tyr Gly Gln Ala Cys Asn Ser Cys Phe Ser Ile Ser Ser Phe Tyr
                645                 650                 655
Pro Asn Ile Tyr Ser Leu His Pro Asn Asn Leu Gln Thr Leu Met Trp
            660                 665                 670
Ile Pro Asp Lys Phe Phe Glu Pro Arg Leu Leu His Arg Leu Ile Asn
        675                 680                 685
Leu Arg Lys Leu Gly Ile Leu Gly Val Ser Asn Ser Thr Val Lys Met
    690                 695                 700
Leu Ser Ile Phe Ser Pro Val Leu Lys Ala Leu Glu Val Leu Lys Leu
705                 710                 715                 720
Ser Phe Ser Ser Asp Pro Ser Glu Gln Ile Lys Leu Ser Tyr Pro
                725                 730                 735
His Ile Ala Lys Leu His Leu Asn Val Asn Arg Thr Met Ala Leu Asn
            740                 745                 750
Ser Gln Ser Phe Pro Pro Asn Leu Ile Lys Leu Thr Leu Ala Tyr Phe
        755                 760                 765

```
Ser Val Asp Arg Tyr Ile Leu Ala Val Leu Lys Thr Phe Pro Lys Leu
        770                 775                 780

Arg Lys Leu Lys Met Phe Ile Cys Lys Tyr Asn Glu Glu Lys Met Asp
785                 790                 795                 800

Leu Ser Gly Glu Ala Asn Gly Tyr Ser Phe Pro Gln Leu Glu Val Leu
                805                 810                 815

His Ile His Ser Pro Asn Gly Leu Ser Glu Val Thr Cys Thr Asp Asp
            820                 825                 830

Val Ser Met Pro Lys Leu Lys Lys Leu Leu Leu Thr Gly Phe His Cys
        835                 840                 845

Arg Ile Ser Leu Ser Glu Arg Leu Lys Lys Leu Ser Lys
    850                 855                 860

<210> SEQ ID NO 46
<211> LENGTH: 26272
<212> TYPE: DNA
<213> ORGANISM: Artificial
<220> FEATURE:
<223> OTHER INFORMATION: BAC clone
<220> FEATURE:
<221> NAME/KEY: misc_feature
<222> LOCATION: (195)..(3310)
<223> OTHER INFORMATION: mutator transposable element
<220> FEATURE:
<221> NAME/KEY: CDS
<222> LOCATION: (6140)..(8731)
<220> FEATURE:
<221> NAME/KEY: misc_feature
<222> LOCATION: (11924)..(13956)
<223> OTHER INFORMATION: partial Rpi-edn2 homologous gene
<220> FEATURE:
<221> NAME/KEY: CDS
<222> LOCATION: (15157)..(17745)

<400> SEQUENCE: 46
aaggggttcg cgttggccga ttcattaatg cagctggcac gacaggtttc ccgactggaa      60
agcgggcagt gagcgcaacg caattaatgt gagttagctc actcattagg cacccccaggc    120 tttacacttt atgcttccgg ctcgtatgtt gtgtggaatt gtgagcggat aacaatttca    180
cacaggaaac agctatgacc atgattacgc caagctattt aggtgagact atagaatact    240
caagcttgca tgcctgcagg tcgactctag aggatcttaa agaagctaaa agaattgtga    300 gttttttactc tattgttaga aaggttgcac ttaaagttga aaaaagtgac tctacaagat    360
tgagatactt gtgtgatatt ggttgtccat ttgagtgttt gatatctgaa gataggaaaa    420
atcagggatt caaaattaaa accttgaaca ccaaacactc atgtggtgaa atgcttttta    480
agaatagaag agccactcaa gaagctttag catactactt caagaaaaaa cttcagaata    540
atccaaagta cagtgtaaat gatatgagac aagatttgga tgataatttt aatttgaacg    600
ttagttattc caagatgaag agggttaaaa ggcttgtgtt agagaaattg gagggtagct    660
acattgatga attcaataag ttggagggct atgctcaaga attgagggac agcaaccctg    720
gtactgatgt tatcataaat atatctagag atgctttgga acaaggtaaa agaaaattct    780
taagaatgta tgtgtgcatt caagctttaa aaaatggctg gaaggaggt ttgaggcctt    840 ttatagggct agatgggact ttttttaaaag gaaaatgcaa gggaatcttg ttggttgcaa    900
tgggacaaga ttcagtgaaa cacttctatc cacttgcttg ggcagtggtg gacagagaga    960
catctagaac atggaaatgg tttattgagt tgctgagaaa ttctctagac ctggcaaatg   1020
gtgaaggagt aacattcatg tctgatatgc ataaggtagt tgtttctgat tttaataagt   1080
ttctgatttt cagttaaatt cttatacaaa taatacttta acttgttatg attttttattg   1140
```

-continued

```
ttacaggggc tactggatgc tgttagtcag gtgtttccta aagcacatca tagatggtgt    1200
gcaaggcaca tagaagctaa ttggagcaag gcttggaaag gtgtacagat gagaaagtta    1260
ctgtggtggt ctgcctggag cacctatgaa gaagaatttc atgatcaatt gaaagtcatg    1320
ggtgctgtgt ctaaacaagc tgcaaaggat ttggtatggt accctgcaca aaactggtgc    1380
agggcttatt ttgacacagt ctgcaaaaat cactcatgtg agaataattt taccgagtca    1440
ttcaacaaat ggattctaga agcaagggca aaacctataa tcaagatgtt agaaaatatt    1500
agaatcaagg tgagttgtta ctgtttatat tatcatcttt tatattatct taatctaact    1560
attaggttct atgtaggtta gattaatgtg ggataatact gaaaattaga gtttgggttg    1620
tttacagttt ggtgattttg agttttcggc tcacaaagtt gtaattttcc ttattctttt    1680
caaattctgc tgcttttgtt gtgaactatg gccttgtttt tctttatttg aatctcttgg    1740
gtatttacaa aacgaattta tcaggaactg aattttacat ttgagattaa ggccttaaag    1800
agcagtgctc aattctctgt aaatttattt tcattgatag atatagtgtt ttaatagaaa    1860
tagcagaata tagtttgatg tgactgttat attgatagga tatgttgatc ttactgttgt    1920
attgttatat agattatgaa taggttgcaa aaacttgaag aagaaggtaa aaattggaaa    1980
ggagatttta gtccatatgc catggagttg tataatgatt tcaatatcat tgcacaatgt    2040
tgtcaagttc aatctaatgg agaccaagga tatgaggtag ttgagggtga agataggcat    2100
gtggtgaatc ttaataggaa gaagtgtaca tgtaggacat gggacttgac tggtatacca    2160
tgtcctcatg ccattaaagc atatcttcat gacaaacaag aaccactgga tcagttgagt    2220
tggtggtatt ccagagaagc ttacatgttg gtatacatgc ataaaataca acctgttaga    2280
ggtgagaagt tctggaaagt tgatccttct catgctatgg agccaccaga aatacataaa    2340
ttggtaggca ggccaaaact taagagaaag agagaaaagg atgaggcaag gaaaagggaa    2400
ggggtgtggt tagcttcaag aaaaggacta aaaatgacat gtggacattg tagtgcaaca    2460
ggtcacaacc aaagaagatg tcctatggta tgtaattttc tttacttggt caatatttac    2520
actagttaat tcaacatcta actaattttg tcattttat agcttcaaag atcaaaacaa    2580
ccaacccaag atgtgccaat gtcagcaccc caagccagtc aagaagaatc tgatattgtc    2640
ttcatgccta ctcctggctt tattgcttct tcaagtcaac agagtatcca acctgctggt    2700
ccttcaaatt caaagaaaat tgaaaagaaa cctactggac cttcaaagtc aaagagaaaa    2760
atagttgctg atgaatctga ggatgagcaa catgttgcac cttcaagtgc agttgctgat    2820
gaggatagag gtgagcatga aagtgaagac gagcagacaa ttctaaggcc gaaggcaatt    2880
tctgaagcta ggactaggct tcaagctaaa aagatacaga ttcgaccaac tggtaccagg    2940
aggattggct tcaaaggaga tgacaatggt gtgagcattc caactaatct gccatactca    3000
ccaagaaaat tggcatggaa aggaaaagaa actatgactt caaatcagtt gacagctgaa    3060
aaggagatca gaattggcaa tttgaaggca agaaaggaa aaaatctac gacttcagat    3120 cagttgactg ttgaaaagga gaaaaaaatt ggcaaattga aggcaaaaag gggtgggaag    3180
aagtagttgc attatgaagt tggttttttg ttttccggtg ttatgtaatg gcatgatgaa    3240
acttaatatt ttgactttt tgatattact ctgtcttgaa caagtgtctg taagttttg    3300 tgggttcaaa atatatgaca atgccattac tacttatcta tgtagttgtt attttttgtt    3360
ttccagttac attatgtatg ttgctttatc tgggaagatg tcttgatggt aggcttaaca    3420
gatcttgtga gttgtgaatc cccagtgata tttcttttga acttgagtga gttgataatt    3480
tctagtgttg ggagtgtttc tttaattttta gttgtctact aagttgtaca gatgacaaaa    3540
```

```
tggctgagat catattatat tgttaacctg catttgtgta aaattgaaaa gcaatccata    3600
atttagatgc tgtaaaaatt tgcagattgc tgtaaaaatg cgcagattgc tgtaaaaata    3660
ctgtaaaaat ttgcagattg ctgtaaaaat ttacagattg ctgtaaaagt ttacagattg    3720
tagattgctg caaaaatttg cagattacag attgctgtaa aaatttacag attacagatt    3780
gctgtaaaaa tttacagatt acagattgct gtaaaaattt acagattgct gtaaaaatgc    3840
agattttgta atggtaaaa atgcagattg ctaacattaa caagattgct aacttttcca    3900
ttacaatcaa gagatcaaca agattgctaa caactttcaa caagcaaaac acaatggcat    3960
tacatcagtt gtaaccggta tattgctaac attacatcaa atactaacg actacaccac    4020 actactacaa cagagctaca ccaaactgct aacgactaca cactactaga acagagctac    4080
accaaactac taacgactac acactactag aacagagcta caccaaacta ctaacgacta    4140
cacactacta gaacagagct acaccaaact actaacgact acacactact agaacagagc    4200
tacaccaaac tactcacgac tacacattac aaacgatcca agaaaagaag ttcaaacata    4260
actacaatac actacatcaa cttggcagct acaaaaccaa caataatatc ccaaaagatc    4320
agaagcaagc ttatcaattg aaacccttc aacttccact tcagtttatt atcatccaag    4380
ttcttcaaat tagaacattc aatatgatgt tccaactcca agtttgaaac tttatcctcc    4440
aaatttgaat tttcaaaaaa agtcatatca ttcaagttag aatcaatgtt tggtttatga    4500
atttcaatgc cacctatttc ctttaggatc ttcttcaatc ggtttcttcc cttccgaatt    4560
gaatctaatt caatcttttg attgtgagtc atcaatgacg catgacttgg aagtttacta    4620
acgatccaat ccaataacca caagagaatg agcaaggacg acaacatttg aagaatcgac    4680
gttcaccatt ctcacgggtc atagcagtaa aatattttgc tatcaatcca cacttacatg    4740
tatgagactc aacttgttga gggagaagaa cagaagaaga tgtcaacatt gaacaacac     4800 aaaatttaac aaatctaatg aagaagatga ttttcaaaag agcttcaaga actaacagat    4860
gaaatttggg ggaaatgttt agggttttgt ttaaagaaat gggtaatggg tgttttattt    4920
ggatgggttg ggtattttga agatgggtcg ggtggatccg ggtggatagg gtggtttggg    4980
tcaaacaaat taggctttaa ttaattaaat ttccaatcaa ttacaacatg ccacgtaata    5040
aatgaaataa ttaaatatat tttctaagta gtctgttagt caaagggca aaataggtcc     5100 ctaaaggtta accccgaggg tattttgagg ccaaaaggta aacgaggggt attttgtac     5160 caattctgat actataaggg tattttagac ccttctccct tttttttttt aactttaatg    5220
cgacactttt tcatatttta tattttcctc aaattatatc ttttttttttc ttttccttgt   5280 tgtaagtcct ggtgaaataa cctcgtgata ccacaaggat ttgaagatta cactcacaac    5340
aaaataaaat atttttttga ttcaagctct aaaaatgaaa aaatactggt agaaagtatt    5400
tctttcttaa actagcatta cgtgatatga atttgaatta gtctaatcaa taaatttaga    5460
acaaaacatt ccttaccagg aaagtgaaga gattttgacc attccactag agtcattatg    5520
gtgatgtctc accaccaaat caaagtttaa taaaaatcga accgaataac cgaacgtcca    5580
ctcggaccaa ttttttttttt tttgagagga tcaaatcgca taaaagccta attttcatgt   5640
aacatacaaa ttgagtctca taatatccca aactcacagc catgaaccca aattgggtaa    5700
agttttgcaa gacattttag gaaatttaaa aatggcgtct ggatatttaa ttttttaaaa    5760
atatcgtgtg attgattaat tatactaaag atatttgctt agttacgtga cttttcaaaa    5820
aaagaaaaag aaaagtacat tatcaatcat cagccacaaa atattaagtc acagtttgtt    5880
tcttaaattc catatcgaat taaattgaat gacacttaaa ttggaacgaa tggtgcaatt    5940
```

-continued

```
tccttcgact attcaactag tatcttatcc acagcatgtg ttgatccttt tttctttcgt      6000
ttttcattta cttgacatta ttaggagact tggcagtgga ctccaactat tctaagctga      6060
cctttctttt cctttaccaa ttatcttctt ctttctaatt actcattctg atcagttttt      6120
tgtagctact gaaaaagaa atg gct gaa att ctt ctt aca gca gtc atc aat      6172
              Met Ala Glu Ile Leu Leu Thr Ala Val Ile Asn
                1               5                  10 aaa tct gta gaa ata gct gca aat gta ctc ttt caa caa ggg agc cgc      6220
Lys Ser Val Glu Ile Ala Ala Asn Val Leu Phe Gln Gln Gly Ser Arg
         15                  20                  25 ttg aat ttt ttg aaa gag gac atc gat tgg ctc cag aga gta ctg aga      6268
Leu Asn Phe Leu Lys Glu Asp Ile Asp Trp Leu Gln Arg Val Leu Arg
    30                  35                  40 cac att cga tca tat gta gac gat gca aag gcc aag gaa gtt gga ggc      6316
His Ile Arg Ser Tyr Val Asp Asp Ala Lys Ala Lys Glu Val Gly Gly
45                  50                  55 gat tca agg gtc aaa aac tta tta aaa gat att caa gaa ttg gca ggt      6364
Asp Ser Arg Val Lys Asn Leu Leu Lys Asp Ile Gln Glu Leu Ala Gly
60                  65                  70                  75 gat gtg gag gat ctc tta gat gag ttt ctt cca aaa atc caa caa tcc      6412
Asp Val Glu Asp Leu Leu Asp Glu Phe Leu Pro Lys Ile Gln Gln Ser
                80                  85                  90 aat aag ttc aaa ggc gca att tgt tgc ctt aag acg gtt tct ttt gcc      6460
Asn Lys Phe Lys Gly Ala Ile Cys Cys Leu Lys Thr Val Ser Phe Ala
        95                  100                 105 gat gag ttt gct gtg gag att gag aag ata aga aga agg gtt gct gac      6508
Asp Glu Phe Ala Val Glu Ile Glu Lys Ile Arg Arg Arg Val Ala Asp
            110                 115                 120 att gat agt tta agg aca act ttc aac atc aca gat aca agt aac aac      6556
Ile Asp Ser Leu Arg Thr Thr Phe Asn Ile Thr Asp Thr Ser Asn Asn
125                 130                 135 aat aat gat tgc att cca atg gaa cag aga aga aaa ttc ctt cat gct      6604
Asn Asn Asp Cys Ile Pro Met Glu Gln Arg Arg Lys Phe Leu His Ala
140                 145                 150                 155 gat gaa aca gag gtc atc ggt ttg gat gat gac ttc aac aag ctc caa      6652
Asp Glu Thr Glu Val Ile Gly Leu Asp Asp Asp Phe Asn Lys Leu Gln
                160                 165                 170 gac aaa ttg ctt gtt caa gat ttg tgt aat gga gtt gtt tca ata gtt      6700
Asp Lys Leu Leu Val Gln Asp Leu Cys Asn Gly Val Val Ser Ile Val
        175                 180                 185 ggc atg cct ggt cta gga aaa aca act ctt gcc aag aaa ctt tat agg      6748
Gly Met Pro Gly Leu Gly Lys Thr Thr Leu Ala Lys Lys Leu Tyr Arg
            190                 195                 200 cat gtc cgt cat caa ttt gag tgt tct gca ctg gtc tac gtt tca caa      6796
His Val Arg His Gln Phe Glu Cys Ser Ala Leu Val Tyr Val Ser Gln
205                 210                 215 cag cca aga gca gga gaa atc tta ctt gac ata gcc aag caa gtt gga      6844
Gln Pro Arg Ala Gly Glu Ile Leu Leu Asp Ile Ala Lys Gln Val Gly
220                 225                 230                 235 ctg acg gac gag gga agg aaa gaa cac ttg gag gac aat cta aga tca      6892
Leu Thr Asp Glu Gly Arg Lys Glu His Leu Glu Asp Asn Leu Arg Ser
                240                 245                 250 ctt ttg gaa aca aaa agg tat gtt att ctc tta gat gac att tgg gat      6940
Leu Leu Glu Thr Lys Arg Tyr Val Ile Leu Leu Asp Asp Ile Trp Asp
        255                 260                 265 act aaa atc tgg gat gct ctg aac cgt gtc ctt cgt cct gaa tgt gat      6988
Thr Lys Ile Trp Asp Ala Leu Asn Arg Val Leu Arg Pro Glu Cys Asp
            270                 275                 280
```

| | | | | | | | | | | | | | | | | |
|---|---|---|---|---|---|---|---|---|---|---|---|---|---|---|---|---|
| tca | aaa | att | ggc | agt | agg | ata | att | atc | act | tct | cga | tat | cat | cat | gta | 7036 |
| Ser | Lys | Ile | Gly | Ser | Arg | Ile | Ile | Ile | Thr | Ser | Arg | Tyr | His | His | Val | |
| | 285 | | | | 290 | | | | | 295 | | | | | | |

| | | | | | | | | | | | | | | | | |
|---|---|---|---|---|---|---|---|---|---|---|---|---|---|---|---|---|
| ggc | aga | tac | ata | gga | gag | gat | ttc | tcg | ctc | cac | gag | ttg | caa | ccc | tta | 7084 |
| Gly | Arg | Tyr | Ile | Gly | Glu | Asp | Phe | Ser | Leu | His | Glu | Leu | Gln | Pro | Leu | |
| 300 | | | | | 305 | | | | | 310 | | | | | 315 | |

| | | | | | | | | | | | | | | | | |
|---|---|---|---|---|---|---|---|---|---|---|---|---|---|---|---|---|
| gat | tca | gag | aaa | agt | ttt | gaa | ctc | ttt | acc | aag | aaa | atc | ttt | att | ttt | 7132 |
| Asp | Ser | Glu | Lys | Ser | Phe | Glu | Leu | Phe | Thr | Lys | Lys | Ile | Phe | Ile | Phe | |
| | | | | 320 | | | | | 325 | | | | | 330 | | |

| | | | | | | | | | | | | | | | | |
|---|---|---|---|---|---|---|---|---|---|---|---|---|---|---|---|---|
| gat | aat | aat | aat | aat | tgg | gct | aat | gct | tca | cct | gtc | ttg | gta | gat | att | 7180 |
| Asp | Asn | Asn | Asn | Asn | Trp | Ala | Asn | Ala | Ser | Pro | Val | Leu | Val | Asp | Ile | |
| | | | | 335 | | | | | 340 | | | | | 345 | | |

| | | | | | | | | | | | | | | | | |
|---|---|---|---|---|---|---|---|---|---|---|---|---|---|---|---|---|
| ggt | aaa | agt | ata | gtt | cgg | aga | tgt | gga | ggt | att | cca | tta | gcc | att | gtg | 7228 |
| Gly | Lys | Ser | Ile | Val | Arg | Arg | Cys | Gly | Gly | Ile | Pro | Leu | Ala | Ile | Val | |
| | | 350 | | | | | 355 | | | | | 360 | | | | |

| | | | | | | | | | | | | | | | | |
|---|---|---|---|---|---|---|---|---|---|---|---|---|---|---|---|---|
| gtg | acg | gca | ggc | atg | tta | agg | gca | aga | gaa | aga | acg | gaa | cat | gca | tgg | 7276 |
| Val | Thr | Ala | Gly | Met | Leu | Arg | Ala | Arg | Glu | Arg | Thr | Glu | His | Ala | Trp | |
| | 365 | | | | | 370 | | | | | 375 | | | | | |

| | | | | | | | | | | | | | | | | |
|---|---|---|---|---|---|---|---|---|---|---|---|---|---|---|---|---|
| aat | aga | gtg | ctt | gag | cgt | ata | ggt | cat | aat | att | cag | gat | gga | tgt | gct | 7324 |
| Asn | Arg | Val | Leu | Glu | Arg | Ile | Gly | His | Asn | Ile | Gln | Asp | Gly | Cys | Ala | |
| 380 | | | | | 385 | | | | | 390 | | | | | 395 | |

| | | | | | | | | | | | | | | | | |
|---|---|---|---|---|---|---|---|---|---|---|---|---|---|---|---|---|
| aag | gca | ttg | gct | ctg | agt | tac | aat | gat | ttg | ccc | att | gca | tta | agg | cca | 7372 |
| Lys | Ala | Leu | Ala | Leu | Ser | Tyr | Asn | Asp | Leu | Pro | Ile | Ala | Leu | Arg | Pro | |
| | | | | 400 | | | | | 405 | | | | | 410 | | |

| | | | | | | | | | | | | | | | | |
|---|---|---|---|---|---|---|---|---|---|---|---|---|---|---|---|---|
| tgt | ttc | ttg | tac | ttt | ggt | ctt | tac | ccc | gag | gac | cat | gaa | att | cgt | gct | 7420 |
| Cys | Phe | Leu | Tyr | Phe | Gly | Leu | Tyr | Pro | Glu | Asp | His | Glu | Ile | Arg | Ala | |
| | | | | 415 | | | | | 420 | | | | | 425 | | |

| | | | | | | | | | | | | | | | | |
|---|---|---|---|---|---|---|---|---|---|---|---|---|---|---|---|---|
| ttt | gat | ttg | aca | aat | atg | tgg | att | gct | gag | aag | ctg | ata | gtt | gta | aat | 7468 |
| Phe | Asp | Leu | Thr | Asn | Met | Trp | Ile | Ala | Glu | Lys | Leu | Ile | Val | Val | Asn | |
| | | 430 | | | | | 435 | | | | | 440 | | | | |

| | | | | | | | | | | | | | | | | |
|---|---|---|---|---|---|---|---|---|---|---|---|---|---|---|---|---|
| agt | ggc | aat | ggg | cga | gag | gct | gaa | agt | ttg | gcg | gat | gat | gtc | cta | aat | 7516 |
| Ser | Gly | Asn | Gly | Arg | Glu | Ala | Glu | Ser | Leu | Ala | Asp | Asp | Val | Leu | Asn | |
| | 445 | | | | | 450 | | | | | 455 | | | | | |

| | | | | | | | | | | | | | | | | |
|---|---|---|---|---|---|---|---|---|---|---|---|---|---|---|---|---|
| gat | ttg | gtt | tca | aga | aac | ttg | att | caa | gtt | gcc | aag | agg | aca | tat | gat | 7564 |
| Asp | Leu | Val | Ser | Arg | Asn | Leu | Ile | Gln | Val | Ala | Lys | Arg | Thr | Tyr | Asp | |
| 460 | | | | | 465 | | | | | 470 | | | | | 475 | |

| | | | | | | | | | | | | | | | | |
|---|---|---|---|---|---|---|---|---|---|---|---|---|---|---|---|---|
| gga | aga | att | tca | agt | tgt | cgc | ata | cat | gac | ttg | tta | cat | agt | ttg | tgt | 7612 |
| Gly | Arg | Ile | Ser | Ser | Cys | Arg | Ile | His | Asp | Leu | Leu | His | Ser | Leu | Cys | |
| | | | | 480 | | | | | 485 | | | | | 490 | | |

| | | | | | | | | | | | | | | | | |
|---|---|---|---|---|---|---|---|---|---|---|---|---|---|---|---|---|
| gtt | gac | ttg | gct | aag | gaa | agc | aac | ttc | ttt | cac | acc | gag | cac | aat | gca | 7660 |
| Val | Asp | Leu | Ala | Lys | Glu | Ser | Asn | Phe | Phe | His | Thr | Glu | His | Asn | Ala | |
| | | | | 495 | | | | | 500 | | | | | 505 | | |

| | | | | | | | | | | | | | | | | |
|---|---|---|---|---|---|---|---|---|---|---|---|---|---|---|---|---|
| ttt | ggt | gat | ccc | ggc | aat | gtt | tct | agg | ctg | cga | agg | att | aca | ttc | tac | 7708 |
| Phe | Gly | Asp | Pro | Gly | Asn | Val | Ser | Arg | Leu | Arg | Arg | Ile | Thr | Phe | Tyr | |
| | | 510 | | | | | 515 | | | | | 520 | | | | |

| | | | | | | | | | | | | | | | | |
|---|---|---|---|---|---|---|---|---|---|---|---|---|---|---|---|---|
| tct | gat | aat | aat | gcc | atg | aat | gag | ttc | ttc | cgt | tca | aat | cct | aag | ctt | 7756 |
| Ser | Asp | Asn | Asn | Ala | Met | Asn | Glu | Phe | Phe | Arg | Ser | Asn | Pro | Lys | Leu | |
| | 525 | | | | | 530 | | | | | 535 | | | | | |

| | | | | | | | | | | | | | | | | |
|---|---|---|---|---|---|---|---|---|---|---|---|---|---|---|---|---|
| gag | aag | ctt | cgt | gca | ctt | ttc | tgt | ttc | aca | aaa | gga | gac | tct | tgc | ata | 7804 |
| Glu | Lys | Leu | Arg | Ala | Leu | Phe | Cys | Phe | Thr | Lys | Gly | Asp | Ser | Cys | Ile | |
| 540 | | | | | 545 | | | | | 550 | | | | | 555 | |

| | | | | | | | | | | | | | | | | |
|---|---|---|---|---|---|---|---|---|---|---|---|---|---|---|---|---|
| ttt | tct | cat | ttg | gct | cat | cat | gac | ttc | aaa | tta | tta | caa | gtg | ttg | gtt | 7852 |
| Phe | Ser | His | Leu | Ala | His | His | Asp | Phe | Lys | Leu | Leu | Gln | Val | Leu | Val | |
| | | | | 560 | | | | | 565 | | | | | 570 | | |

| | | | | | | | | | | | | | | | | |
|---|---|---|---|---|---|---|---|---|---|---|---|---|---|---|---|---|
| gta | gtc | cag | cct | cga | aaa | aat | tat | gat | ttc | agc | att | agc | caa | atc | aaa | 7900 |
| Val | Val | Gln | Pro | Arg | Lys | Asn | Tyr | Asp | Phe | Ser | Ile | Ser | Gln | Ile | Lys | |
| | | | | 575 | | | | | 580 | | | | | 585 | | |

| | | | | | | | | | | | | | | | | |
|---|---|---|---|---|---|---|---|---|---|---|---|---|---|---|---|---|
| att | ggg | aac | atg | agt | tgc | tta | cgc | tat | ctg | cga | ttc | gag | ggg | gat | att | 7948 |
| Ile | Gly | Asn | Met | Ser | Cys | Leu | Arg | Tyr | Leu | Arg | Phe | Glu | Gly | Asp | Ile | |
| | | 590 | | | | | 595 | | | | | 600 | | | | |

| | | |
|---|---|---|
| tat ggg aaa ctg cca aat tgt atg gtg aag ctc aaa cac tta gag acc<br>Tyr Gly Lys Leu Pro Asn Cys Met Val Lys Leu Lys His Leu Glu Thr<br>605 610 615 | | 7996 |
| cta gat att agt aaa agc ttc att att aaa ctt cct act ggt gtt tgg<br>Leu Asp Ile Ser Lys Ser Phe Ile Ile Lys Leu Pro Thr Gly Val Trp<br>620 625 630 635 | | 8044 |
| aag act aca caa ttg aga cat ctt cgt tct aat ggt tat aat cta gca<br>Lys Thr Thr Gln Leu Arg His Leu Arg Ser Asn Gly Tyr Asn Leu Ala<br>640 645 650 | | 8092 |
| cct tac agt tac ttt tgt ata agc cca ttt ttt cca aac gtg cct cct<br>Pro Tyr Ser Tyr Phe Cys Ile Ser Pro Phe Phe Pro Asn Val Pro Pro<br>655 660 665 | | 8140 |
| aat aat gta caa act ttg atg tgg atg gat ggt gaa ttt ttt gaa ccg<br>Asn Asn Val Gln Thr Leu Met Trp Met Asp Gly Glu Phe Phe Glu Pro<br>670 675 680 | | 8188 |
| aga tgg ttg cac cga ttt atc aat tta aga aaa ctg ggt tta cag gaa<br>Arg Trp Leu His Arg Phe Ile Asn Leu Arg Lys Leu Gly Leu Gln Glu<br>685 690 695 | | 8236 |
| gta tcc gat tct acc att aag aaa tta tca aca ttg agc cct gtg cca<br>Val Ser Asp Ser Thr Ile Lys Lys Leu Ser Thr Leu Ser Pro Val Pro<br>700 705 710 715 | | 8284 |
| acg aca ctg gag gtt cta aag ctc agc tca ttt ttc agt gaa ttg aga<br>Thr Thr Leu Glu Val Leu Lys Leu Ser Ser Phe Phe Ser Glu Leu Arg<br>720 725 730 | | 8332 |
| gag caa ata aac ttg tcg tcg tat cca aat att gtt aag ttg cat ttg<br>Glu Gln Ile Asn Leu Ser Ser Tyr Pro Asn Ile Val Lys Leu His Leu<br>735 740 745 | | 8380 |
| aac gga aga att ccc ttg aac gtc tct gaa tca ttc cct cca aat ctt<br>Asn Gly Arg Ile Pro Leu Asn Val Ser Glu Ser Phe Pro Pro Asn Leu<br>750 755 760 | | 8428 |
| gtc aag ctt act ctt tgc aac ttg atg gta gac ggt cat gta gtg gca<br>Val Lys Leu Thr Leu Cys Asn Leu Met Val Asp Gly His Val Val Ala<br>765 770 775 | | 8476 |
| gtg ctt aag aaa tta ccc aaa tta aag ata ctt aca ttg cat agg tgc<br>Val Leu Lys Lys Leu Pro Lys Leu Lys Ile Leu Thr Leu His Arg Cys<br>780 785 790 795 | | 8524 |
| aga cat gat gca gaa aaa atg gat ctc tct ggt gat ggt gat agc ttt<br>Arg His Asp Ala Glu Lys Met Asp Leu Ser Gly Asp Gly Asp Ser Phe<br>800 805 810 | | 8572 |
| ccg caa ctt gaa gtt ttg cat att aaa gat cca gtc tgc ttg tct gaa<br>Pro Gln Leu Glu Val Leu His Ile Lys Asp Pro Val Cys Leu Ser Glu<br>815 820 825 | | 8620 |
| gta acg tgc acg gat gat gtc ggt atg cct aaa ttg aaa aag tta tta<br>Val Thr Cys Thr Asp Asp Val Gly Met Pro Lys Leu Lys Lys Leu Leu<br>830 835 840 | | 8668 |
| ctt ata gaa aga act gat tcc aac gtt agg ctc tcg gaa aga ctt gca<br>Leu Ile Glu Arg Thr Asp Ser Asn Val Arg Leu Ser Glu Arg Leu Ala<br>845 850 855 | | 8716 |
| aag ctg aga gta tga aaatcccaat gtgtcaacag gttagttatt tacttttaat<br>Lys Leu Arg Val<br>860 | | 8771 |
| atctcaaaat aagctcattt tttattaatt aattcatgaa ctaaatattt tatgtctaat | | 8831 |
| aaattgcaga tgcttttcag aatgattatg tctttgctgg agagcatctt ttgatgcctg | | 8891 |
| tttgtatttg taataaataa attaaatgtt tgattgcttc ttcaagttga tgtatttgtg | | 8951 |
| gcttctaatt tgtaaaataa atatatttat tcatctattt atggtcttat gtatatttac | | 9011 |
| ctttggaatt agcagtagct taattagttt cttttcttct tcaagaatca atgctcacaa | | 9071 |
| ttctagtttt aaacacgtta ctaaacttac attctaagta ttctaattaa cttagtcctt | | 9131 |

```
caattctaaa cttgaaactt ttagactcta gagcttcttt ccaaaatttt taatctatga      9191
tcattaaatt catcgcacgt cttgtcaatc aatattatgt catctaacat ccgaaaataa      9251
catacactgg cacttcactt tggatatatc gtgtcgattg gtccatcatt aagacaaaaa      9311
ggaacatgct aagggttgat tcctatgcaa ttccatccta atcgagaagt gttctgactc      9371
actcccacaa ttctaatcca aattttaatt ccatagataa tgtggtaaat caaattaaat      9431
tacaattaat aggccttttt tttctttta agaaacgtct ctcaatttat acaagaaata       9491
gctgtgtata acatactgac attttggtta taccaaagtt ctccttacat tttactcctt      9551
cctttccgaa atattctgat gactcgcttt ttgagagtca aattatatgg actttaatca      9611
atatcttaac atgtattgtt tttaggatca tattatgtta ttaaatttta attatatgag      9671
gggggattat catatatagt actattttat agttttaaa tatttaattt aactaatcaa       9731
atttaacttc aaatatgagt caaattataa acacaacaac acaattatca gggatgcaat      9791
ctaccactga gctaatagcc cgttgtgcga gcctcccact gggggccgct aatattgtta      9851
tatacctcta caaaggcaa ctatttgggg gtggttgaag taaatattgt agtgggatga       9911
cctaaaaaaa gtgcatatta cagttgtcta gttatatggt acactatata tagtattata     9971
ttatgtgcaa ttctggtaaa atatttaata ttgcacctct aaaattggta cgtatattta    10031
tttacacttt catcttttgc aatgaaggag atggcttaaa tatgggtaat ggataacatg    10091
caactggggt ttgcatatat ctgataaggt tgtagtagaa tggtaaataa ctaaatatcc    10151
atctattttt aatcaaagat tttggatttg agttctcttt tgtacgaaat tgtcttcgtt    10211
aaaaagcact tcacctctca atctgggact cctgacgcga aattggattt agtcagactt    10271
caatgagggt actagccacc gggtgagaaa caaaaaaaaa tgcatttact tgtcatgttt    10331
cgcaaaagtt aatttgatta attttcggag tcaggttgaa ttaaattaat tcaatatttt    10391
aaatttggat gttcaaaaat tatactatca atctttctca tattaatata atgaaaaata    10451
tattttaaaa tgtaaatcaa agtttatgtg gacaataaaa cggagtgtgt aatttattgc    10511
aaaatgaatc actcaactac ctcaatgtgg acaataaaac gccatagata acttgcaatg    10571
aatttctcca attacctaat ttaaagtctt gccacctatg tatatttttt ttctccatta    10631
attataagac ttattagctc tttaattact tagataacga ctactctttt attccatttt    10691
atatatggaa aaattgaatt tctatataag ataagtttat aaaatatttt tagctagaga    10751
actactcttg cagttcaaat taatgttagc ggttttagaa tctaaaattg ttttataaca    10811
gagatctcga gttcaatttt taagtgtaaa tttcgtttta attaatagga agagttctac    10871
ttcaaaatgg aattgtctcg cataaatcca gattattcga attctaaaat gagtatggta    10931
tatcacatgg aaaaataata tatatcttga aatataggat aataggagtg gataatttca    10991
tgtaaacctt cttaattttt cctagtaggg actagaaaat gagcaaaagt ggcatctcaa    11051
tcatgcaaaa agttaattaa aaaataaaat aaattaagag ccttgtgcac taaattctga    11111
ctagaacaga attataagat tttatagtac gtaatcttat tttatatttc tataaaaaaa    11171
tattttcata actcgaattt atattgatct tccgataaca cataatcaat taattagtac    11231
acagtacttc attccttaaa gttttttgtc atgatgaaag attttgaaag ttttgaattc    11291
tgtccaaatc ctgaggacaa aaacttctat atcacacagc agaaaaaaat aaaattaaag    11351
aaacaaaaat aaaataagaa caagagtgag tatgtatata gctatgcact cgttataatg    11411
atatttcatt atagcaaacct gatttttttc ataatcaatt tttcatgtta tatttactta    11471
taaccacagt gtcattcatt atagcagtag acttttttgta aaattactcc tctatgacaa    11531
```

```
ttatactcaa tattatataa taatattttg taaaaaatat attatatata aaataaaata  11591
ttcaaatatt tatgataatt atcattaaac taggcaaatt ttattaaatt tttaggtaat  11651
tatacaaatt ataagtaaaa ctctcaaact taagtaaaaa tttgggcgaa ttaagttatt  11711
atgacccatg gttttagcct atatgatcca acttatatca acctaataat atatgattgg  11771
gccatcattt attaactcag tctatttagt tttaatcagc tcaaatataa ttcaactcgc  11831
tcatttaaca ccgcagctat caatatatac acctatttag tataccatga gctacataaa  11891
tcattgctag tttataatct cacctcaaaa gcctatataa acatttcatt gagccatcat  11951
ttattaactc agtctattta gttttaatca gctcaaatat aatttaactc gctcatttct  12011
caccgctgtc agctaacaat atatacataa tacacctatt tagtatacca tataccatga  12071
gctatatata aatcattgct agtttattat ctcacctcaa aatcctatat aatccatcct  12131
ctacataatc aagaacatcc caaattgtct acaagctcct ctactcccac ttaggaaaaa  12191
aaaataatcc aaaaatggtg tcttcaaaat tagaagatgg tctaatttac aacataaaat  12251
tatcctcagt tggaccagct agagtaacag gacaagatgt tgtttatgag ccaagtaaca  12311
tggatttggc cgtgaaattg ctttatttttt tatagtaata attcagctga cttagtaaat  12371
attggtagaa gtatagttga gagatgcaga ggtataccac tagccattgc ggtgatagca  12431
ggcatgttaa gggcaaaaga aagaacagaa tatgcatgga gcagagtgct tcagagtttg  12491
ggtcataaaa ttcaggatgg atgtgctaag gtactggttc tgagttgcaa tgattttccc  12551
attgcactaa ggcaatgttt cttgtacttt ggcctttacc ctgaggtact ggctctgagt  12611
tacaatgaga gttcccattg ctaatgcttt tgatttgaca aatatgtgga ttgctgagaa  12671
gttgatagtt gtaaatagtg gtaatatgcg agaggctgaa gatttggtgg agggtgtcct  12731
taatgatttg gtttctagaa acttgattca agttgccaaa tagaaatatt cgcatacatg  12791
acttgttaca tagtttgtgt gtggacttgg ctgaggaaag taacttcttt cacactgagc  12851
acaatgcatt tggtaatctc cgcaatgttt ctagggtgcg aaggattaca ttctactctg  12911
ataataatgc catgaatgag ttctttcgtt caaatcctta tcctaagaag cttcgtggac  12971
ttctctgttt cacaaaagac cgttgcatat tttctgaatt ggctcatctt aacttcaaat  13031
tattgcaagt gctggttgta gtcatgtctc aagatggtta tgggggtttc actatgggaa  13091
acaaatttgg gaagatgagt tgctttatgc tatctgcgat tggaggggggt aattagcgga  13151 aaattgccaa ataatattgt gaagctcaaa tgtctagagg ccatagatat tggagtgggc  13211
gacattgaac ttccttgtag tgtttgggat tttaaacaat tgagacatgt tcattgtaga  13271
gaagaactta aggatttctt ttctataagc ccaaacatgt ggctcatgat aatctacaaa  13331
ctttgatgtg gatggatgat aaattttttg aggcgagatt gttgcaccaa ttgataaatt  13391
taagaaaact gggtataagt tcagcatctg attctaccat taagatatta tcagcattga  13451
gccctgtgcc aacagcgttg gaggttctga agctcaaatt ttgcaatgaa tcgagtgagc  13511 aaaataaactt gtcgtcgtat ccaaatattg ttaagatgca tttgaacgca gcaatgcgct  13571
tgaactgtga agcattccct ccacatctgg tcaagcttac tcttgtctac ttgacggtag  13631
acgatcatgt agtggcagtg cttaagaaat tacccaaatt acgaatactt aaaatggttg  13691
tctgcgaaca taaaaagaa gagatggatc tctctggtga tggctttccg caacttgaag  13751
ttttgcatat tcaaaatcca ctctggttgc ttgaaataat atgtacggat gatgtcaata  13811
tgcctaaact gaacaagcta ttacttgtag ataccaaatg cgagaggtca gtatgtctct  13871
ccgatcgtct cgcaaagctg agaatatgaa aatcccaagc ttatttttcta tttaattaat  13931
```

```
tcatgagcta aatattttat gtctaataaa ttgcagatgc atttcagaat gatttaactc      13991
ttcttctgat gcatctttgt atttgtaatt aaataaataa aatgtttgat tgctttcttg      14051
tgccttgtga tttgtaaaag atatatgaag tagtaagggg tagagataaa catttgatat      14111
atatgtacgg ctgaagttag tgaattatta ttggttgaca caataatcca atattaaaaa      14171
taaaattgaa ccaataaccc actattttt tttaataaa atcatttaaa aatcgttgac       14231
cctataaccc aagaggaata aatcaatagt atttttttcg attcaattta catcaaagg      14291 gacttagttt taaactaaac aatgaattta tgtatgctcc actatgatta tataaattaa      14351
cttttctaat gtcaattagg aaataaactt gcaacgcacg ttcctagaac tagtgtatat      14411
atatatatat atattctagt gggataatca tatactgctt caatctgctg acgactctaa      14471
aaattctttg ttcttgtttg aaaatgaaat atataataaa gatttaacaa ttgttttaat      14531
gaactgaaat ataatcggac gaaggagatt ccagaagctt cggtgtgaac tcatctttgc      14591
cattgaattt tacgcgtagt actgcctcaa ttgtctgacc ttcaacgtgg atccaagatt      14651
gttattaacg gtatcaatgg ttgtagtaaa aaaaattaat ttgaggttaa tagcacaaaa      14711
acacacaact tcaaggaact ttcgtaatac cttaaccact acactaaacc tttaacttgt      14771
gtccagagat gttaatactt gtatatatat ttatttaaat caaaatttga cctctatata      14831
cagtgtaatt ttccgacaaa ggggtatggg taagggcggc gcccctgcat tcttgaaaac      14891
gaaataccag ctaatatgat taagaaacga tgaattattg tatttaatat gaacagagta      14951
gttgcttctg tccatttgtt ctttcatttt catctacttg acattattat tattagtagt      15011
aattacaaga cttggccgtc gactccaaca cctaaagcaa atagtgcatc tttcttatcc      15071
ttttaccaaa aattgatcat ctttttctct tactttccct tgctaatcct cacatttaga      15131
aaacagaaat tcaaggaaaa aagag atg gct gaa att ctt ctc aca gca gtc         15183
                            Met Ala Glu Ile Leu Leu Thr Ala Val
                                865                 870 atc aat aaa tca ata gca ata gct gga aat gta ctc ttt caa gaa gga         15231
Ile Asn Lys Ser Ile Ala Ile Ala Gly Asn Val Leu Phe Gln Glu Gly
        875                 880                 885 atg cgt tta tat tgg ttg aaa gag gac ata gat tgg ctc cat aga gaa         15279
Met Arg Leu Tyr Trp Leu Lys Glu Asp Ile Asp Trp Leu His Arg Glu
    890                 895                 900 atg aga cac att cga tca tat gta gac gat gca aag gcc aag gaa gtt         15327
Met Arg His Ile Arg Ser Tyr Val Asp Asp Ala Lys Ala Lys Glu Val
905                 910                 915                 920 gga ggt gat tca aag gtc aaa aac tta tta aaa gat att caa caa ctg         15375
Gly Gly Asp Ser Lys Val Lys Asn Leu Leu Lys Asp Ile Gln Gln Leu
                925                 930                 935 gca ggt gat gtg gag gat ctc tta gat gag ttc ctt cca aaa att caa         15423
Ala Gly Asp Val Glu Asp Leu Leu Asp Glu Phe Leu Pro Lys Ile Gln
            940                 945                 950 caa tcc aat aag ttc aaa ggc gca att tgt tgc ctt aag aca gcc tgc         15471
Gln Ser Asn Lys Phe Lys Gly Ala Ile Cys Cys Leu Lys Thr Ala Cys
        955                 960                 965 atc cct tgt gcc aat gag ttt gct atg gag att gag agg ata aaa aga         15519
Ile Pro Cys Ala Asn Glu Phe Ala Met Glu Ile Glu Arg Ile Lys Arg
    970                 975                 980 agg gtt gcg gac att gac cgt gta agg aca act tac aac atc atg gat         15567
Arg Val Ala Asp Ile Asp Arg Val Arg Thr Thr Tyr Asn Ile Met Asp
985                 990                 995                 1000 aca aat aac aac aat gat tgc att cca ttg gac aag aga aga ttg             15612
Thr Asn Asn Asn Asn Asp Cys Ile Pro Leu Asp Lys Arg Arg Leu
                1005                1010                1015
```

-continued

| | |
|---|---|
| ttc ctt cat gct gat gaa aca gag gtc atc ggt ttg gat gat gac<br>Phe Leu His Ala Asp Glu Thr Glu Val Ile Gly Leu Asp Asp Asp<br>1020                        1025                      1030 | 15657 |
| ttc aat aag cta caa gcc aaa tta ctt gat cat gat ttg cct tat<br>Phe Asn Lys Leu Gln Ala Lys Leu Leu Asp His Asp Leu Pro Tyr<br>1035                        1040                      1045 | 15702 |
| gga gtt gtt tca ata gtt ggc atg ccc ggt ttg gga aaa aca act<br>Gly Val Val Ser Ile Val Gly Met Pro Gly Leu Gly Lys Thr Thr<br>1050                        1055                      1060 | 15747 |
| ctt gcc aag aaa ctt ttt agg cat gtc cgt cat caa ttt gag tgt<br>Leu Ala Lys Lys Leu Phe Arg His Val Arg His Gln Phe Glu Cys<br>1065                        1070                      1075 | 15792 |
| tct gga ctg gtc tat gtt tca caa cag cca agg gcg gga gaa atc<br>Ser Gly Leu Val Tyr Val Ser Gln Gln Pro Arg Ala Gly Glu Ile<br>1080                        1085                      1090 | 15837 |
| tta cat gac ata gcc aaa caa gtt gga ctg aca gaa gag gaa agg<br>Leu His Asp Ile Ala Lys Gln Val Gly Leu Thr Glu Glu Glu Arg<br>1095                        1100                      1105 | 15882 |
| aaa gaa aac ttg gag ggc aac cta cga tca ctc ttg aaa aca aaa<br>Lys Glu Asn Leu Glu Gly Asn Leu Arg Ser Leu Leu Lys Thr Lys<br>1110                        1115                      1120 | 15927 |
| agg tat gtt atc ctc cta gat gac att tgg ggt gtt gaa att tgg<br>Arg Tyr Val Ile Leu Leu Asp Asp Ile Trp Gly Val Glu Ile Trp<br>1125                        1130                      1135 | 15972 |
| gat gat ctg aaa cgt gtc ctt cct gaa tgt gat tca aaa gtt ggc<br>Asp Asp Leu Lys Arg Val Leu Pro Glu Cys Asp Ser Lys Val Gly<br>1140                        1145                      1150 | 16017 |
| agt agg ata att atc act tct cga aat aat aat gta ggc aga tac<br>Ser Arg Ile Ile Ile Thr Ser Arg Asn Asn Asn Val Gly Arg Tyr<br>1155                        1160                      1165 | 16062 |
| ata gga gag gat tcc tcg ctc cac gag ttg caa ccc tta gat tca<br>Ile Gly Glu Asp Ser Ser Leu His Glu Leu Gln Pro Leu Asp Ser<br>1170                        1175                      1180 | 16107 |
| gag aag agt ttt gaa ctc ttt acc aag aaa atc ttt act ttt gat<br>Glu Lys Ser Phe Glu Leu Phe Thr Lys Lys Ile Phe Thr Phe Asp<br>1185                        1190                      1195 | 16152 |
| aac aat aat aat tgg gcc aat gct tca cct aac ttg gta aat att<br>Asn Asn Asn Asn Trp Ala Asn Ala Ser Pro Asn Leu Val Asn Ile<br>1200                        1205                      1210 | 16197 |
| ggt aga agt ata gtt gag aga tgt gga ggt ata ccg tta gcc att<br>Gly Arg Ser Ile Val Glu Arg Cys Gly Gly Ile Pro Leu Ala Ile<br>1215                        1220                      1225 | 16242 |
| gtg gtg acc gca ggc atg tta agg gca aga gaa aga ata gaa cgt<br>Val Val Thr Ala Gly Met Leu Arg Ala Arg Glu Arg Ile Glu Arg<br>1230                        1235                      1240 | 16287 |
| gca tgg aac aga gta ctt gag agt atg ggt cat aaa att cag gat<br>Ala Trp Asn Arg Val Leu Glu Ser Met Gly His Lys Ile Gln Asp<br>1245                        1250                      1255 | 16332 |
| gga tgt gct aag gta ttg act ctg agt tac aat gat ttg ccc att<br>Gly Cys Ala Lys Val Leu Thr Leu Ser Tyr Asn Asp Leu Pro Ile<br>1260                        1265                      1270 | 16377 |
| gca tta agg ccg tgt ttc ttg tac ttt ggc ctt ttc cct gag gac<br>Ala Leu Arg Pro Cys Phe Leu Tyr Phe Gly Leu Phe Pro Glu Asp<br>1275                        1280                      1285 | 16422 |
| cat gaa att cgt gct ttt gat ttg aca aat atg tgg att gct gag<br>His Glu Ile Arg Ala Phe Asp Leu Thr Asn Met Trp Ile Ala Glu<br>1290                        1295                      1300 | 16467 |
| aag ctg ata gtt gta aat agt ggc aat ggg cga gag gct gaa agt<br>Lys Leu Ile Val Val Asn Ser Gly Asn Gly Arg Glu Ala Glu Ser<br>1305                        1310                      1315 | 16512 |

```
tta gcg gag gat att  cta aat gat ttg gtt  tct aga aac ttg att       16557
Leu Ala Glu Asp Ile  Leu Asn Asp Leu Val  Ser Arg Asn Leu Ile
            1320                  1325                  1330 caa gtt gcc aaa agg  aca tat gat gga aga  att tca agt tgt cgc       16602
Gln Val Ala Lys Arg  Thr Tyr Asp Gly Arg  Ile Ser Ser Cys Arg
            1335                  1340                  1345 ata cat gac ttg tta  cat agt ttg tgt gtt  gac ttg tct aag gaa       16647
Ile His Asp Leu Leu  His Ser Leu Cys Val  Asp Leu Ser Lys Glu
            1350                  1355                  1360 agt aat ttc ttt cac  act gag cac aat gca  ttt ggt gat ccc ggc       16692
Ser Asn Phe Phe His  Thr Glu His Asn Ala  Phe Gly Asp Pro Gly
            1365                  1370                  1375 aat gtt gct aag gtg  cga agg att aca ttc  tac tct aat aat aat       16737
Asn Val Ala Lys Val  Arg Arg Ile Thr Phe  Tyr Ser Asn Asn Asn
            1380                  1385                  1390 gcc atg aat gag ttc  ttc cgt tca aat cct  aag cct agg aag ctt       16782
Ala Met Asn Glu Phe  Phe Arg Ser Asn Pro  Lys Pro Arg Lys Leu
            1395                  1400                  1405 cgt gca ctt ttc tgt  ttc ata aat gac agt  tgc cta ttt tct cat       16827
Arg Ala Leu Phe Cys  Phe Ile Asn Asp Ser  Cys Leu Phe Ser His
            1410                  1415                  1420 atg gat cat ctt aat  ttc aaa tta ttg caa  gtg ttg gta gta gtc       16872
Met Asp His Leu Asn  Phe Lys Leu Leu Gln  Val Leu Val Val Val
            1425                  1430                  1435 ata tct aat aat gat  ata cgg agt gcc agg  aga atc cca aac acg       16917
Ile Ser Asn Asn Asp  Ile Arg Ser Ala Arg  Arg Ile Pro Asn Thr
            1440                  1445                  1450 ttt ggg aac atg agt  tgc tta cgc tat ctg  caa ttc gag ggg aat       16962
Phe Gly Asn Met Ser  Cys Leu Arg Tyr Leu  Gln Phe Glu Gly Asn
            1455                  1460                  1465 att tat ggg aaa ctg  cca aat tgt atg gtg  aag ctc aaa cat cta       17007
Ile Tyr Gly Lys Leu  Pro Asn Cys Met Val  Lys Leu Lys His Leu
            1470                  1475                  1480 gag acc cta gat att  ggt aaa agc ttc att  aaa ctt cct act ggt       17052
Glu Thr Leu Asp Ile  Gly Lys Ser Phe Ile  Lys Leu Pro Thr Gly
            1485                  1490                  1495 gtt tgg aag ttt aca  caa tta aga cat ctt  ctt tat aaa gat tat       17097
Val Trp Lys Phe Thr  Gln Leu Arg His Leu  Leu Tyr Lys Asp Tyr
            1500                  1505                  1510 agt cag gca tct aac  agt tgc ttt tct ata  agc cca tct gtt cca       17142
Ser Gln Ala Ser Asn  Ser Cys Phe Ser Ile  Ser Pro Ser Val Pro
            1515                  1520                  1525 aac gtg tac tca ttg  cct cct aat aat cta  caa act ttg atg tgg       17187
Asn Val Tyr Ser Leu  Pro Pro Asn Asn Leu  Gln Thr Leu Met Trp
            1530                  1535                  1540 atg aat gat aaa tgt  ttt gaa gca aga ttg  ttg cac cga ttg atc       17232
Met Asn Asp Lys Cys  Phe Glu Ala Arg Leu  Leu His Arg Leu Ile
            1545                  1550                  1555 aat tta aga aaa ctg  ggt ata gaa gaa gta  tct gat tct acg att       17277
Asn Leu Arg Lys Leu  Gly Ile Glu Glu Val  Ser Asp Ser Thr Ile
            1560                  1565                  1570 aag ata tta gca gca  tcg agc cct gtg caa  ccg gcg ctg gag att       17322
Lys Ile Leu Ala Ala  Ser Ser Pro Val Gln  Pro Ala Leu Glu Ile
            1575                  1580                  1585 ctg aag ctc gaa ttt  tcc agg gac atg agt  gag gat ata aac ttg       17367
Leu Lys Leu Glu Phe  Ser Arg Asp Met Ser  Glu Asp Ile Asn Leu
            1590                  1595                  1600 tcg tcc tat cca aat  att gtt aag ttg cat  ttg aac gga aga atg       17412
Ser Ser Tyr Pro Asn  Ile Val Lys Leu His  Leu Asn Gly Arg Met
            1605                  1610                  1615
```

```
ccc ttt aac ttt gta gca tca ttc cct cca aat ctt gtc aag ctt      17457
Pro Phe Asn Phe Val Ala Ser Phe Pro Pro Asn Leu Val Lys Leu
            1620                1625                1630 act ctt gtc gac ttt ggc gta gac agt cag gta gtg gca gtg ctt      17502
Thr Leu Val Asp Phe Gly Val Asp Ser Gln Val Val Ala Val Leu
            1635                1640                1645 aag aaa ttg ccc aaa ttg aag ata ctt aaa atg gtt tgc tgc gta      17547
Lys Lys Leu Pro Lys Leu Lys Ile Leu Lys Met Val Cys Cys Val
            1650                1655                1660 cat agt gaa gaa aag atg gat ctc tct ggt ggt gat agc ttt ccg      17592
His Ser Glu Glu Lys Met Asp Leu Ser Gly Gly Asp Ser Phe Pro
            1665                1670                1675 caa ctt gaa ttt ctg cat att aaa gaa tca tta tgc ttg ttt gaa      17637
Gln Leu Glu Phe Leu His Ile Lys Glu Ser Leu Cys Leu Phe Glu
            1680                1685                1690 ata acg tgc atg gat gat gtg agt atg cct aaa ttg aaa aag cta      17682
Ile Thr Cys Met Asp Asp Val Ser Met Pro Lys Leu Lys Lys Leu
            1695                1700                1705 tta ctt atg gat acc att ccc aac gtt agg ctc tcg gaa aga ctt      17727
Leu Leu Met Asp Thr Ile Pro Asn Val Arg Leu Ser Glu Arg Leu
            1710                1715                1720 gta aag ctg aga gta tga aaatcccaat gtgtcaacag gttagttatt         17775
Val Lys Leu Arg Val
            1725 tactttaat atctcaaaat aagatcatta tttatttatt aattaattca cgaactaaaa 17835 attttatgtc taataaattg cagatgcttt tcagaatgat taagtctttg gtggagacca 17895 tcttctgatg cctgtttgta ataaataaat taaatgtttg attgttttc  aagttgatgt 17955 atttgtggct tctaatttgt aaaatatatt tatttatcta tttattgtct tatgcatatt 18015 tacctcgaat tagcagtagc tttagttctc tttcttcttc aagaatcaat gctcacaatt 18075 ctagttttgt aaagtaatat atttaggaaa aatccttttg gtttgaatgg tattttactt 18135 atgtacttat tttatcttt  tgaacatttt tatcttttta actttaatac cttttaatta 18195 aaaaaaatag aaaaaagatc aatttatttt aaaataaaaa ggatattata attttttaaa 18255 atttctagcc aaattgtggc caatttttct agtcatttag cattactcat atatttattg 18315 tctttatgta tatctacctt gacacatgca catttcttta tgagatcgac cccaacctt  18375 gttgaattta ttattgctat gagtctacta tttacatttt attttaaagt gtagaattgg 18435 ccatgatcag agtataactc cagcattcaa taatttgaaa tataaaatac aaatatagtt 18495 taatcaattt tttatctatg tattttggtt ttatttatgt caaatacaag gtatgcatcc 18555 ttaaagatta aaaaatctac acatttcatc cccaaactat aaaatatttc aacataaaag 18615 ttttaaaatt catctaacaa ggtatcatga ggagctggcc ttcctaataa tgacttttgt 18675 ttgctaaaga atttcacaaa attaaaaatc actcacaatc tgtcacgccc cgagcctaca 18735 ccctggacgg gaccggcacc cgaagaccat ttctagcccc aagcgaaccc ttggcctggc 18795 tttcttaact cagtggaaac ctaacccaac agaataactc aatgctaatg caaggttaga 18855 aaacaactta acttataaaa tatggccata aaggcaactc gaatctcaaa atagaatatt 18915 tacatatata tatagatgag agactcaaaa ctaacggact gactgtctgt ctatgaagcc 18975 tctaaaatac tgagatggat gttgggacag accccgcaac atcctaataa aacaaaaaac 19035 taagaacaca aaataattga gtcctccgga atgcaaggag ctcaccact  gactctggag 19095 tgctcagctg gatcaacgac gtgcaggatg ctgatccggg gcacctgaat ctgcatcatc 19155 aaacgatgca ggccaactgg catcagtaca tggaaattac gagtatgcga gctggaaaac 19215
```

```
taagcaacaa aggctagaag gaaatctgga agaaactgaa tagcttacct ggctcaactc   19275
aactcaacct gactgacttc tttcaatata aggcaattta aaacaagtgc gatataaaga   19335
aagactgttt aaaacatgct ataaactctg tgtgtataca aggatacaat aagcctgaaa   19395
tgtatataga aatacaatga actgatgtat ataaaaatac aataatctct gtgtatgaaa   19455
atacaataat tgctgtggga gtttctctaa ccgacaacca tcacataaga gctatagtga   19515
tgatacagcg atcgacctca cgctgccaga gcatcttata cctggccaaa ggtacaagac   19575
ctgaactgcc taatggatcc actagtttaa tctgaaaagg atttatctaa aaagtatgat   19635 cctttctac ccatggtggc taacatggtt ctatggggc tgtgggttct ttgaacgctc     19695
ccccaattcg gtgctcgata ctactcccaa aaatgtactg gctcttatgt ttttaaaaca   19755
tatttcttcc tgctgatatg agataattac tcaaaaacta gcccgaaggc tcttttggaa   19815
atctcagttt ccaaccttgt ttaaatgtaa aaacatttct ttaaaacttc tttgggaata   19875
catagttccc taataacttt gagaaaagaa ctcaactttaa aactctttac tttacttgaa   19935
ctcttagctt gatgtgaaac tcttaacttt tgacttgact tgaaactcaa tacttaactt   19995
ggaacttgag ccttagaatg aagttaaaac gttcaatgaa gactcttaga aaaccttaaa   20055
gacttgcttt gacttactta cttctaagct tgacttcact tgacttggaa actaacttca   20115
cttgaattgg aaactaactt cacttgactt gtagttttac ttgactttta gaagtaccttt  20175 ggagtgttgg aaacaactag gaaatatagg tataatacct aggaacatgt atgaaaaaaa   20235
tggtgaatga aagggaagga ttggtgtcct tggcactagg agaggtgcga cagcccagcc   20295 ccttttttccc caaaaaatcc gactttttcc ccttgtttct ttccaattct aaaccctctc   20355
aacctcaagg tttcagcagc aacacataga atcataaaga tccttattat acaatagatt   20415
caactcaaaa atcacagcca gaaatctgta ctaaaccagc aagaacttca acacaacacc   20475
actacaactt caacaaccaa taaatctttt cttggaatta aaaatgagtt ggtgtgtggg   20535
ggtatgaacc aaccaatact aaggatcatc aatctctcaa catacaatag atcacaactc   20595
aaatacacag cccaatcctg tcccacaacc aacaataact tcaacaacac aactaacaac   20655
atcaacaaca actaacaact tcaacaacaa atccaatctt ttctcaaacc ataaacatga   20715
gcttggtgag tgggggaaag gatcaaccca cacaaagaac tcacatacct tgatagggat   20775
cacccccgac gaaaatccac aatgatcttg acgaatcttg ttgatctcct ctttcttctc   20835
ttcttcttct ccttcttctc ttcttcttct cttcttcacc ctcaagaacc ctaactcttt   20895
ctctttcaaa atgggacaaa atgatccaaa gatcagccta atacaacaat ataagctcaa   20955
aagaaatgat ttgtgaaaag actaaaatgc ccttaaattt ccggacggac tccttgccaa   21015
ctgccccaac tttcaagggg cataactcgc tcatacgaac tcggaatcga gtaaactcgg   21075
tggcgttgga aatatcattc cacaagcttc gaaaccataa ttggaaatac tcctaactca   21135
tcctgatcta ggagttacga ctgctcaaag ttggccaaaa actcactgat ttccacactt   21195
agccaaattt ccagattttt gaacttagcc aaattttcca gattctggac tgccaaattt   21255
ccagatttta aattttttcca aaaatgacta tttccaaatt tcaagcttct tcaaagccac   21315
ttcaaattgt cggatgttac acaatcaaag ttagaattct agctatgtat atgataaagt   21375
cttataattt agctaaaatc atatgtttat gttaaaaatt cattgaatat atatatattt   21435
aaataattaa ttcaaaatca taaattattt tttttataaa aaatttaaa gctcatgaac   21495 tcaaaatttt aaatttggat ctgctcacta ttgcatcca attttggccc tccccgataa   21555
taattaattg ccgagcttct taactttcaa acgatttaga ataattagct ttataaaatt   21615
```

-continued

```
taaaatagtt tcgaggtttt taaataattt caatcgattt tcataagcat tttgaataag    21675
caatatattt catataatca tatatgtagt tagtacatct tataagtatt taaaaatcat    21735
acaaaaagat ttatacgttg ttaaaataaa tatttattta acttagtttc attcggaact    21795
atagttttaa aattttgaat caattagtgg gtttttaaaa ttaattggtt tattaattaa    21855
gttaactatt ttatttcaat aagaataaga agctcactaa ttaatcacac taattcgttt    21915
tatttaaatt ttaatcaaat ttgtcaatcg agctcaattt agttaaactc caattccaat    21975
cggccacaat tgaactcaaa aggccatatc ttaatttgga atatagcatt tttatttatg    22035
aaattagcca tttgcctttc aacttttcaa attccttaaa agaccatttt tgggcttgct    22095
tcaatttcca gcataaccca acaactcttc agcccactct ctctattcta attcccttc     22155
ctcttatttc cagcgaccca atccaacccc cgagccggcc caactccttt ccaatcctaa    22215
agaaacttac acggcgtctt catcagcaac ctccagatgt caacaacaca gcagtccaaa    22275
cgcctcaaca tcacagcgag cacacagaga aattcacggc gatacacggc cagaccaaga    22335
gtcaacattg tgagcagtat gttgtgttct tcttgtcctt atcctcgacg tcccttcag    22395
cttatacgaa tcgcagcggg cagcacacac gcgttttctc cccttcctc ttccggaatg    22455
gggtgaaatt tcagaaaaaa tgttagtctc cctaaaaggg tgaaagaatt ggaagttttg    22515
aaatcgaaaa tgggcctcga attgagattc gtccgttttc cctcccaatt cgtgaaccct    22575
aatctccttc tatttattcc ttttttcttt cagtatttgg gggggatttt tgtgagaaaa    22635
gtggggagat ttttagtgga aaaaaattta acttaaggca gcaaaattat ctaaaatacc    22695
atacaaaata tacttcaagg aaaaacagag gagatactct tgttttagtg cttaggtttg    22755
acattattgc ccagacttct cggctactgt ttgtgctcaa gttttcgtgg tgaaggttgt    22815
catttcactc gtttggtctc tgtttcgctg cctgaaaaag gtgagaatat cgcatttatt    22875
tcgcttatag cttttcctc ttctcaacct ttgtgtatct acttcggtct ctctagtagt    22935
tgttttcatt aagatgtctt tgtgtcattt tcgaagtgat ctagtgctta cttgaatatg    22995
cttttctctg tttgtagtct gcttaagtcc ttggttgttg ttctcgtttt aagctcagcc    23055
tatttatttg ttgatcactc tgactttgtt ttgtctccag cggttttgga taatttttc     23115
ttgtttttgt tatatgcgct gaaaatgtcg atgacactat tctgtcactc ctttgtatat    23175
tcttaggcct agattcgaaa ttcatgctaa tgtagatagg cgtatatta ttcgcttttc     23235
acaatcgttt tatgttttag atgattttgc tatgaggccc atatattgct tcttctatag    23295
ttcttgttct atcaatggta ttatgttttg cttactagaa tgctatctga aaagaatgct    23355
aaaacgtgtt cccctctctt ccccgtctta atgaagtgta aagatgttga agctcctttc    23415
ccgttcgtat ttgtgggttc ttatcttact ttattaatac tgtctttggt gcatgtgaag    23475
cttgtaattt aattttagta ccgtatgagc catttgccat tttgcttaat cttatgagag    23535
cataaggtgt ttatcctcat ttaattatta ggagttcact gattactaag gatgagaaga    23595
ttgtttatgt gcatttatgc tgtaataatg agctaaatat ttgttaactg tgggctgttc    23655
tagcatttta gtagtcccctt aacttcacat gtttcatttt ggagtttagt catattaatt   23715
tatgtaataa gaagcatgct ttgacccctct tatttttgt tacttgctgt cactagtatg    23775
ataaatgcc atattgatta gtttatgtta tgattgaatg tgatatctct gtcagttgat     23835
gtaactcggc atgtgacttt gatatggcgc taccatgtga cttagttta ctaaataata     23895
tgtcgtgcgg atactcattc tcggtaaaaa tgcagtaaat cttattaatt agtcaatgac    23955
```

```
accattttgt tttgtatctt agattttaac attagcttac acccaattga tgccttattt    24015
aattattgtt tataataatt ctaatttctt atcattcttt tttgttgcat gtgaaatctg    24075
tccgggacct acggaccta tccttgcatt tttctttggg ccatggaggc ataattctat     24135
ttctatccga gtctaacggc cattaaaagt cgacgaacag gtcccgaagt tgaaaggagc    24195
aaccgattga aaaatttgaa aagattgggc caaaggccca ctcttaattc ataatagttg    24255
tatttcgtta cttctgggcc taagccctgt tgacacctaa ttttgaccct ctccgataat    24315
aattagtttt tgagcttctt aattttaaa cgatttagaa taattagctt tataaaatgc     24375
aaatagtttt aaggttatct taaagtaatt tcagtcggtt tttatagtat ttcgaatgat    24435
aaatatattt cgtataatta tatgcataat tagtatattt tataaatgtt tgaaaaccat    24495
gtcaaaagat ttttactttg ttaaaaataa atattttatt tatttagtta tagtttgaat    24555
tgtggtttta gttttggatt aataagttta taggtaaatc gattagttta tggttaaatt    24615
aattatttta ttttgttaag attaaagagc tcataagtta attatgttaa tttgtcttat    24675
ttaaattgct agccgaactt atcccaatta attcaatttg gctacatctc tagtccccga    24735
ttggctatga tttaagtcat atggcaaaag cttaagttaa ttctcaccaa tttaatttca    24795
tccttgaccc atcttaaatg aacaaacttt ggacttgcat ttgcattttt aacaaacttc    24855
cagcctatac tttattccta tcacaccaaa gacccaaccc catacgtata gccaaataag    24915
gcccaaaatc catcagcctt gttcatcaca aatatcagaa ataagttcag cccattatta    24975
ggttttcatc cttattctat cattaagact cacaacatct cttccttttc ctttcttagg    25035
caaagttcca atttgttttc atcccaattc agattggttt caccattttc agctaagttt    25095
ttcctctctc ccttgcacat ttaaagctcc ttattgaaaa gctgaatttt tcttttttt     25155
tgttgaccaa aattcgctgc aactatggag aaaaaggacg attttgttga tctctctctg    25215
tcacattttg gactgatctc aacgtgcttt tttttttcaa aaactcaaac aattttccat    25275
tctccaattc ccgcttaaaa aggttttggc tataaaggtt cagaaaaaat cttcagtagg    25335
gggaaagaaa ttttttttg agttagaaag aatatagaga attagctagt attagaaagg    25395
aagaaataca ctcaaatcat atagttccta aaatcacaga aagacttcct gttcttgctt    25455
gcttcctctt tgttcgttgg agttcttgga ttcacattct agtggtagtg aagtcacttc    25515
cttgctcgct ctggcctcag tttcgctgct ccaaagaagg taatgctctc tcctttgtaa    25575
tgttttcctt atcgtttttt tttgtttcca gcgtgacatc tatagatatg ctttgtttgg    25635
tttgctagta cttgtcgttg agttcgggat ggtttgctat aatatgactt ctttaagcaa    25695
tttcaatata aatggattca tatgtcccga gtttatttct ttgtctctgt cgcgtatgtt    25755
gattttggac gtccgaacct atatttcttt attttcaatg gcttaagacg ttagaatggg    25815
cgctcatttt gttaacgttg atggtatgag ctatttttc ttaaaatgaa agatgatttc     25875
tcaaactgtc taaaatggaa attggatgtt atattacgta ctgtttgaga tccccgggta    25935
ccgagctcga attcgcccta tagtgagtcg tattacaatt cactggccgt cgttttacaa    25995
cgtcgtgact gggaaaaccc tggcgttacc caacttaatc gccttgcagc acatccccct    26055
ttcgccagct ggcgtaatag cgaagaggcc cgcaccgatc gcccttccca acagttgcgc    26115
agctgaatgg cgaatggcgc ctgatgcggt attttctcct tacgcatctg tgtggtattt    26175
cacaccgcat atggtgcact ctcagtacaa tctgctctga tgccgcatag ttaagccagc    26235
cccgacaccc gccaacaccc gctgacgcga acccctt                             26272
```

```
<210> SEQ ID NO 47
<211> LENGTH: 863
<212> TYPE: PRT
<213> ORGANISM: Artificial
<220> FEATURE:
<223> OTHER INFORMATION: Synthetic Construct

<400> SEQUENCE: 47
```

| | | | | | | | | | | | | | | | |
|---|---|---|---|---|---|---|---|---|---|---|---|---|---|---|---|
| Met | Ala | Glu | Ile | Leu | Thr | Ala | Val | Ile | Asn | Lys | Ser | Val | Glu | Ile | |
| 1 | | | | 5 | | | | | 10 | | | | | 15 | |
| Ala | Ala | Asn | Val | Leu | Phe | Gln | Gln | Gly | Ser | Arg | Leu | Asn | Phe | Leu | Lys |
| | | | 20 | | | | | 25 | | | | | 30 | | |
| Glu | Asp | Ile | Asp | Trp | Leu | Gln | Arg | Val | Leu | Arg | His | Ile | Arg | Ser | Tyr |
| | | | 35 | | | | | 40 | | | | | 45 | | |
| Val | Asp | Asp | Ala | Lys | Ala | Lys | Glu | Val | Gly | Gly | Asp | Ser | Arg | Val | Lys |
| | 50 | | | | | 55 | | | | | 60 | | | | |
| Asn | Leu | Leu | Lys | Asp | Ile | Gln | Glu | Leu | Ala | Gly | Asp | Val | Glu | Asp | Leu |
| 65 | | | | | 70 | | | | | 75 | | | | | 80 |
| Leu | Asp | Glu | Phe | Leu | Pro | Lys | Ile | Gln | Gln | Ser | Asn | Lys | Phe | Lys | Gly |
| | | | | 85 | | | | | 90 | | | | | 95 | |
| Ala | Ile | Cys | Cys | Leu | Lys | Thr | Val | Ser | Phe | Ala | Asp | Glu | Phe | Ala | Val |
| | | | 100 | | | | | 105 | | | | | 110 | | |
| Glu | Ile | Glu | Lys | Ile | Arg | Arg | Val | Ala | Asp | Ile | Asp | Ser | Leu | Arg | |
| | | 115 | | | | | 120 | | | | | 125 | | | |
| Thr | Thr | Phe | Asn | Ile | Thr | Asp | Thr | Ser | Asn | Asn | Asn | Asp | Cys | Ile | |
| | | 130 | | | | | 135 | | | | | 140 | | | |
| Pro | Met | Glu | Gln | Arg | Arg | Lys | Phe | Leu | His | Ala | Asp | Glu | Thr | Glu | Val |
| 145 | | | | | 150 | | | | | 155 | | | | | 160 |
| Ile | Gly | Leu | Asp | Asp | Asp | Phe | Asn | Lys | Leu | Gln | Asp | Lys | Leu | Leu | Val |
| | | | | 165 | | | | | 170 | | | | | 175 | |
| Gln | Asp | Leu | Cys | Asn | Gly | Val | Val | Ser | Ile | Val | Gly | Met | Pro | Gly | Leu |
| | | | 180 | | | | | 185 | | | | | 190 | | |
| Gly | Lys | Thr | Thr | Leu | Ala | Lys | Lys | Leu | Tyr | Arg | His | Val | Arg | His | Gln |
| | | 195 | | | | | 200 | | | | | 205 | | | |
| Phe | Glu | Cys | Ser | Ala | Leu | Val | Tyr | Val | Ser | Gln | Pro | Arg | Ala | Gly | |
| | 210 | | | | | 215 | | | | | 220 | | | | |
| Glu | Ile | Leu | Leu | Asp | Ile | Ala | Lys | Gln | Val | Gly | Leu | Thr | Asp | Glu | Gly |
| 225 | | | | | 230 | | | | | 235 | | | | | 240 |
| Arg | Lys | Glu | His | Leu | Glu | Asp | Asn | Leu | Arg | Ser | Leu | Leu | Glu | Thr | Lys |
| | | | | 245 | | | | | 250 | | | | | 255 | |
| Arg | Tyr | Val | Ile | Leu | Leu | Asp | Asp | Ile | Trp | Asp | Thr | Lys | Ile | Trp | Asp |
| | | | 260 | | | | | 265 | | | | | 270 | | |
| Ala | Leu | Asn | Arg | Val | Leu | Arg | Pro | Glu | Cys | Asp | Ser | Lys | Ile | Gly | Ser |
| | | 275 | | | | | 280 | | | | | 285 | | | |
| Arg | Ile | Ile | Ile | Thr | Ser | Arg | Tyr | His | His | Val | Gly | Arg | Tyr | Ile | Gly |
| | 290 | | | | | 295 | | | | | 300 | | | | |
| Glu | Asp | Phe | Ser | Leu | His | Glu | Leu | Gln | Pro | Leu | Asp | Ser | Glu | Lys | Ser |
| 305 | | | | | 310 | | | | | 315 | | | | | 320 |
| Phe | Glu | Leu | Phe | Thr | Lys | Lys | Ile | Phe | Ile | Phe | Asp | Asn | Asn | Asn | Asn |
| | | | | 325 | | | | | 330 | | | | | 335 | |
| Trp | Ala | Asn | Ala | Ser | Pro | Val | Leu | Val | Asp | Ile | Gly | Lys | Ser | Ile | Val |
| | | | 340 | | | | | 345 | | | | | 350 | | |
| Arg | Arg | Cys | Gly | Gly | Ile | Pro | Leu | Ala | Ile | Val | Val | Thr | Ala | Gly | Met |
| | | 355 | | | | | 360 | | | | | 365 | | | |

-continued

```
Leu Arg Ala Arg Glu Arg Thr Glu His Ala Trp Asn Arg Val Leu Glu
370                 375                 380
Arg Ile Gly His Asn Ile Gln Asp Gly Cys Ala Lys Ala Leu Ala Leu
385                 390                 395                 400
Ser Tyr Asn Asp Leu Pro Ile Ala Leu Arg Pro Cys Phe Leu Tyr Phe
                405                 410                 415
Gly Leu Tyr Pro Glu Asp His Glu Ile Arg Ala Phe Asp Leu Thr Asn
                420                 425                 430
Met Trp Ile Ala Glu Lys Leu Ile Val Val Asn Ser Gly Asn Gly Arg
            435                 440                 445
Glu Ala Glu Ser Leu Ala Asp Asp Val Leu Asn Asp Leu Val Ser Arg
450                 455                 460
Asn Leu Ile Gln Val Ala Lys Arg Thr Tyr Asp Gly Arg Ile Ser Ser
465                 470                 475                 480
Cys Arg Ile His Asp Leu Leu His Ser Leu Cys Val Asp Leu Ala Lys
                485                 490                 495
Glu Ser Asn Phe Phe His Thr Glu His Asn Ala Phe Gly Asp Pro Gly
                500                 505                 510
Asn Val Ser Arg Leu Arg Arg Ile Thr Phe Tyr Ser Asp Asn Asn Ala
            515                 520                 525
Met Asn Glu Phe Phe Arg Ser Asn Pro Lys Leu Glu Lys Leu Arg Ala
530                 535                 540
Leu Phe Cys Phe Thr Lys Gly Asp Ser Cys Ile Phe Ser His Leu Ala
545                 550                 555                 560
His His Asp Phe Lys Leu Leu Gln Val Leu Val Val Gln Pro Arg
                565                 570                 575
Lys Asn Tyr Asp Phe Ser Ile Ser Gln Ile Lys Ile Gly Asn Met Ser
                580                 585                 590
Cys Leu Arg Tyr Leu Arg Phe Glu Gly Asp Ile Tyr Gly Lys Leu Pro
            595                 600                 605
Asn Cys Met Val Lys Leu Lys His Leu Glu Thr Leu Asp Ile Ser Lys
            610                 615                 620
Ser Phe Ile Ile Lys Leu Pro Thr Gly Val Trp Lys Thr Thr Gln Leu
625                 630                 635                 640
Arg His Leu Arg Ser Asn Gly Tyr Asn Leu Ala Pro Tyr Ser Tyr Phe
                645                 650                 655
Cys Ile Ser Pro Phe Phe Pro Asn Val Pro Asn Asn Val Gln Thr
                660                 665                 670
Leu Met Trp Met Asp Gly Glu Phe Phe Glu Pro Arg Trp Leu His Arg
            675                 680                 685
Phe Ile Asn Leu Arg Lys Leu Gly Leu Gln Glu Val Ser Asp Ser Thr
            690                 695                 700
Ile Lys Lys Leu Ser Thr Leu Ser Pro Val Pro Thr Thr Leu Glu Val
705                 710                 715                 720
Leu Lys Leu Ser Ser Phe Phe Ser Glu Leu Arg Glu Gln Ile Asn Leu
                725                 730                 735
Ser Ser Tyr Pro Asn Ile Val Lys Leu His Leu Asn Gly Arg Ile Pro
                740                 745                 750
Leu Asn Val Ser Glu Ser Phe Pro Pro Asn Leu Val Lys Leu Thr Leu
            755                 760                 765
Cys Asn Leu Met Val Asp Gly His Val Val Ala Val Leu Lys Lys Leu
770                 775                 780
```

```
Pro Lys Leu Lys Ile Leu Thr Leu His Arg Cys Arg His Asp Ala Glu
785                 790                 795                 800

Lys Met Asp Leu Ser Gly Asp Gly Asp Ser Phe Pro Gln Leu Glu Val
                805                 810                 815

Leu His Ile Lys Asp Pro Val Cys Leu Ser Glu Val Thr Cys Thr Asp
            820                 825                 830

Asp Val Gly Met Pro Lys Leu Lys Lys Leu Leu Leu Ile Glu Arg Thr
        835                 840                 845

Asp Ser Asn Val Arg Leu Ser Glu Arg Leu Ala Lys Leu Arg Val
    850                 855                 860

<210> SEQ ID NO 48
<211> LENGTH: 862
<212> TYPE: PRT
<213> ORGANISM: Artificial
<220> FEATURE:
<223> OTHER INFORMATION: Synthetic Construct

<400> SEQUENCE: 48

Met Ala Glu Ile Leu Leu Thr Ala Val Ile Asn Lys Ser Ile Ala Ile
1               5                   10                  15

Ala Gly Asn Val Leu Phe Gln Glu Gly Met Arg Leu Tyr Trp Leu Lys
            20                  25                  30

Glu Asp Ile Asp Trp Leu His Arg Glu Met Arg His Ile Arg Ser Tyr
        35                  40                  45

Val Asp Asp Ala Lys Ala Lys Glu Val Gly Gly Asp Ser Lys Val Lys
    50                  55                  60

Asn Leu Leu Lys Asp Ile Gln Gln Leu Ala Gly Asp Val Glu Asp Leu
65                  70                  75                  80

Leu Asp Glu Phe Leu Pro Lys Ile Gln Gln Ser Asn Lys Phe Lys Gly
                85                  90                  95

Ala Ile Cys Cys Leu Lys Thr Ala Cys Ile Pro Cys Ala Asn Glu Phe
            100                 105                 110

Ala Met Glu Ile Glu Arg Ile Lys Arg Arg Val Ala Asp Ile Asp Arg
        115                 120                 125

Val Arg Thr Thr Tyr Asn Ile Met Asp Thr Asn Asn Asn Asn Asp Cys
    130                 135                 140

Ile Pro Leu Asp Lys Arg Arg Leu Phe Leu His Ala Asp Glu Thr Glu
145                 150                 155                 160

Val Ile Gly Leu Asp Asp Asp Phe Asn Lys Leu Gln Ala Lys Leu Leu
                165                 170                 175

Asp His Asp Leu Pro Tyr Gly Val Val Ser Ile Val Gly Met Pro Gly
            180                 185                 190

Leu Gly Lys Thr Thr Leu Ala Lys Lys Leu Phe Arg His Val Arg His
        195                 200                 205

Gln Phe Glu Cys Ser Gly Leu Val Tyr Val Ser Gln Gln Pro Arg Ala
    210                 215                 220

Gly Glu Ile Leu His Asp Ile Ala Lys Gln Val Gly Leu Thr Glu Glu
225                 230                 235                 240

Glu Arg Lys Glu Asn Leu Glu Gly Asn Leu Arg Ser Leu Leu Lys Thr
                245                 250                 255

Lys Arg Tyr Val Ile Leu Leu Asp Asp Ile Trp Gly Val Glu Ile Trp
            260                 265                 270

Asp Asp Leu Lys Arg Val Leu Pro Glu Cys Asp Ser Lys Val Gly Ser
        275                 280                 285
```

```
Arg Ile Ile Thr Ser Arg Asn Asn Asn Val Gly Arg Tyr Ile Gly
    290                 295                 300

Glu Asp Ser Ser Leu His Glu Leu Gln Pro Leu Asp Ser Glu Lys Ser
305                 310                 315                 320

Phe Glu Leu Phe Thr Lys Lys Ile Phe Thr Phe Asp Asn Asn Asn Asn
                325                 330                 335

Trp Ala Asn Ala Ser Pro Asn Leu Val Asn Ile Gly Arg Ser Ile Val
            340                 345                 350

Glu Arg Cys Gly Gly Ile Pro Leu Ala Ile Val Val Thr Ala Gly Met
        355                 360                 365

Leu Arg Ala Arg Glu Arg Ile Glu Arg Ala Trp Asn Arg Val Leu Glu
    370                 375                 380

Ser Met Gly His Lys Ile Gln Asp Gly Cys Ala Lys Val Leu Thr Leu
385                 390                 395                 400

Ser Tyr Asn Asp Leu Pro Ile Ala Leu Arg Pro Cys Phe Leu Tyr Phe
                405                 410                 415

Gly Leu Phe Pro Glu Asp His Glu Ile Arg Ala Phe Asp Leu Thr Asn
            420                 425                 430

Met Trp Ile Ala Glu Lys Leu Ile Val Val Asn Ser Gly Asn Gly Arg
        435                 440                 445

Glu Ala Glu Ser Leu Ala Glu Asp Ile Leu Asn Asp Leu Val Ser Arg
    450                 455                 460

Asn Leu Ile Gln Val Ala Lys Arg Thr Tyr Asp Gly Arg Ile Ser Ser
465                 470                 475                 480

Cys Arg Ile His Asp Leu Leu His Ser Leu Cys Val Asp Leu Ser Lys
                485                 490                 495

Glu Ser Asn Phe Phe His Thr Glu His Asn Ala Phe Gly Asp Pro Gly
            500                 505                 510

Asn Val Ala Lys Val Arg Arg Ile Thr Phe Tyr Ser Asn Asn Asn Ala
        515                 520                 525

Met Asn Glu Phe Phe Arg Ser Asn Pro Lys Pro Arg Lys Leu Arg Ala
    530                 535                 540

Leu Phe Cys Phe Ile Asn Asp Ser Cys Leu Phe Ser His Met Asp His
545                 550                 555                 560

Leu Asn Phe Lys Leu Leu Gln Val Leu Val Val Ile Ser Asn Asn
                565                 570                 575

Asp Ile Arg Ser Ala Arg Arg Ile Pro Asn Thr Phe Gly Asn Met Ser
            580                 585                 590

Cys Leu Arg Tyr Leu Gln Phe Glu Gly Asn Ile Tyr Gly Lys Leu Pro
        595                 600                 605

Asn Cys Met Val Lys Leu Lys His Leu Glu Thr Leu Asp Ile Gly Lys
    610                 615                 620

Ser Phe Ile Lys Leu Pro Thr Gly Val Trp Lys Phe Thr Gln Leu Arg
625                 630                 635                 640

His Leu Leu Tyr Lys Asp Tyr Ser Gln Ala Ser Asn Ser Cys Phe Ser
                645                 650                 655

Ile Ser Pro Ser Val Pro Asn Val Tyr Ser Leu Pro Asn Asn Leu
            660                 665                 670

Gln Thr Leu Met Trp Met Asn Asp Lys Cys Phe Glu Ala Arg Leu Leu
        675                 680                 685

His Arg Leu Ile Asn Leu Arg Lys Leu Gly Ile Glu Glu Val Ser Asp
    690                 695                 700
```

-continued

```
Ser Thr Ile Lys Ile Leu Ala Ala Ser Ser Pro Val Gln Pro Ala Leu
705                 710                 715                 720

Glu Ile Leu Lys Leu Glu Phe Ser Arg Asp Met Ser Glu Asp Ile Asn
                725                 730                 735

Leu Ser Ser Tyr Pro Asn Ile Val Lys Leu His Leu Asn Gly Arg Met
            740                 745                 750

Pro Phe Asn Phe Val Ala Ser Phe Pro Pro Asn Leu Val Lys Leu Thr
        755                 760                 765

Leu Val Asp Phe Gly Val Asp Ser Gln Val Val Ala Val Leu Lys Lys
    770                 775                 780

Leu Pro Lys Leu Lys Ile Leu Lys Met Val Cys Cys Val His Ser Glu
785                 790                 795                 800

Glu Lys Met Asp Leu Ser Gly Gly Asp Ser Phe Pro Gln Leu Glu Phe
                805                 810                 815

Leu His Ile Lys Glu Ser Leu Cys Leu Phe Glu Ile Thr Cys Met Asp
            820                 825                 830

Asp Val Ser Met Pro Lys Leu Lys Lys Leu Leu Leu Met Asp Thr Ile
        835                 840                 845

Pro Asn Val Arg Leu Ser Glu Arg Leu Val Lys Leu Arg Val
    850                 855                 860
```